(12) United States Patent
Davis

(10) Patent No.: US 11,305,027 B2
(45) Date of Patent: Apr. 19, 2022

(54) UV STERILIZATION SYSTEM AND DEVICE AND RELATED METHODS

(71) Applicant: SEAL SHIELD, LLC, Jacksonville, FL (US)

(72) Inventor: Christian Davis, Jacksonville, FL (US)

(73) Assignee: Seal Shield, LLC, Jacksonville, FL (US)

( * ) Notice: Subject to any disclaimer, the term of this patent is extended or adjusted under 35 U.S.C. 154(b) by 79 days.

(21) Appl. No.: 16/846,550

(22) Filed: Apr. 13, 2020

(65) Prior Publication Data
US 2020/0289688 A1 Sep. 17, 2020

Related U.S. Application Data

(62) Division of application No. 15/898,930, filed on Feb. 19, 2018, now Pat. No. 11,058,783.

(60) Provisional application No. 62/460,516, filed on Feb. 17, 2017, provisional application No. 62/460,347, filed on Feb. 17, 2017.

(51) Int. Cl.
*A61L 2/10* (2006.01)
*G06K 7/10* (2006.01)
*A61L 2/24* (2006.01)

(52) U.S. Cl.
CPC ...... *A61L 2/10* (2013.01); *A61L 2/24* (2013.01); *G06K 7/10366* (2013.01); *A61L 2202/11* (2013.01); *A61L 2202/122* (2013.01); *A61L 2202/14* (2013.01)

(58) Field of Classification Search
CPC .......... A61L 2/10; A61L 2/24; A61L 2202/11; A61L 2202/122; A61L 2202/14; G06K 7/10366
See application file for complete search history.

(56) References Cited

U.S. PATENT DOCUMENTS

| | | | |
|---|---|---|---|
| 5,714,933 | A | 2/1998 | Le Van Suu |
| 7,019,639 | B2 | 3/2006 | Stilp |
| 7,084,756 | B2 | 8/2006 | Stilp |
| 7,495,544 | B2 | 2/2009 | Stilp |
| 7,941,096 | B2 | 5/2011 | Perkins et al. |
| 8,107,925 | B2 | 1/2012 | Natsuno et al. |

(Continued)

FOREIGN PATENT DOCUMENTS

| | | |
|---|---|---|
| WO | WO2013/148755 | 10/2013 |
| WO | WO2015/035132 | 3/2015 |
| WO | WO2016/170511 | 10/2016 |

*Primary Examiner* — Sean E Conley
*Assistant Examiner* — Brendan A Hensel
(74) *Attorney, Agent, or Firm* — Allen, Dyer, Doppelt + Gilchrist, PA

(57) ABSTRACT

A method is for operating a UV sterilization device including a housing defining a cavity, and having a door configured to permit access to the cavity, and trays carried within the cavity. Each tray is configured to receive a mobile wireless communications device. The UV sterilization device may include UV CBAs carried within the cavity respectively adjacent the trays, each UV CBA having LED UV sources configured to irradiate the mobile wireless communications device with UV radiation. The UV sterilization device may include a controller, and the method may include operating the controller to selectively power one of the UV CBAs for disinfecting the mobile wireless communications device.

20 Claims, 75 Drawing Sheets

(56) References Cited

U.S. PATENT DOCUMENTS

| | | | |
|---|---|---|---|
| 8,296,493 B1* | 10/2012 | Engelhardt | A61L 2/20 710/303 |
| 8,606,981 B2 | 12/2013 | Engelhardt et al. | |
| 2003/0072676 A1* | 4/2003 | Fletcher-Haynes | A61M 1/3621 422/23 |
| 2004/0212494 A1 | 10/2004 | Stilp | |
| 2004/0215750 A1 | 10/2004 | Stilp | |
| 2005/0079871 A1 | 4/2005 | Kirk et al. | |
| 2006/0055536 A1 | 3/2006 | Jackson | |
| 2006/0055537 A1 | 3/2006 | Jackson | |
| 2006/0066450 A1 | 3/2006 | Jackson | |
| 2006/0145842 A1 | 7/2006 | Stilp | |
| 2006/0229027 A1 | 10/2006 | Wang et al. | |
| 2008/0094215 A1 | 4/2008 | Amador et al. | |
| 2008/0224066 A1* | 9/2008 | Nolen | A23L 3/28 250/436 |
| 2008/0240724 A1 | 10/2008 | Aguren | |
| 2009/0249444 A1 | 10/2009 | Macauley | |
| 2010/0036511 A1 | 2/2010 | Dongare | |
| 2010/0071038 A1 | 3/2010 | Flynn et al. | |
| 2010/0082988 A1 | 4/2010 | Huebner et al. | |
| 2010/0266445 A1* | 10/2010 | Campagna | A61L 2/10 422/23 |
| 2010/0315225 A1 | 12/2010 | Teague | |
| 2011/0086614 A1 | 4/2011 | Brisebois et al. | |
| 2012/0001751 A1 | 1/2012 | Baker et al. | |
| 2012/0074334 A1 | 3/2012 | Milligan | |
| 2013/0256560 A1 | 10/2013 | Yerby | |
| 2014/0354161 A1 | 12/2014 | Aggarwal et al. | |
| 2015/0086420 A1* | 3/2015 | Trapani | A61L 2/202 422/24 |
| 2015/0118107 A1* | 4/2015 | Sunkara | A61L 2/24 422/24 |
| 2015/0306263 A1* | 10/2015 | Yanke | A61L 2/10 422/24 |
| 2018/0185529 A1* | 7/2018 | Shur | A61L 2/0047 |

* cited by examiner

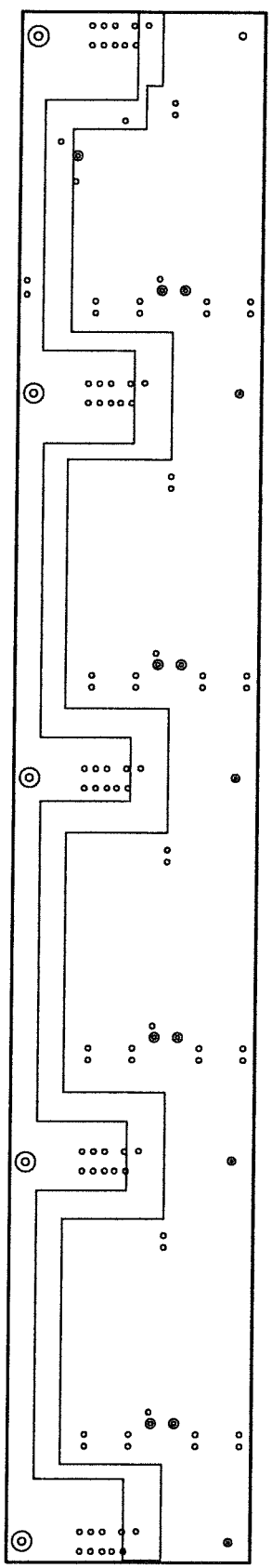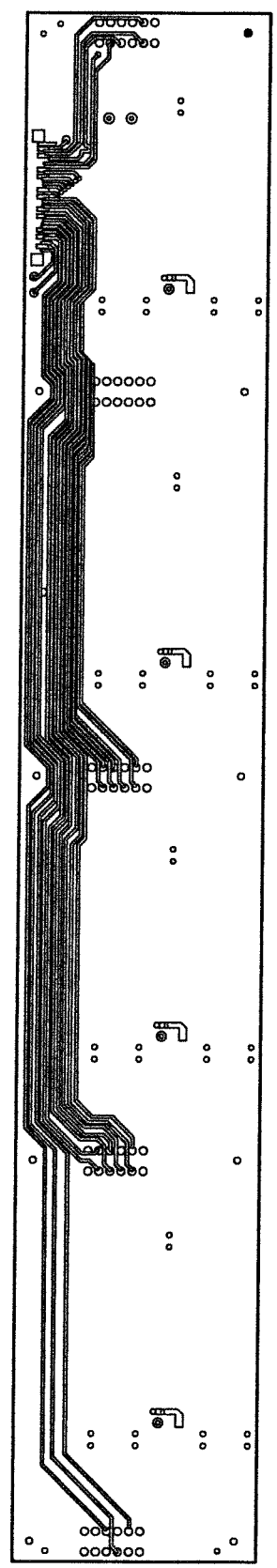
FIG. 28C
FIG. 28D

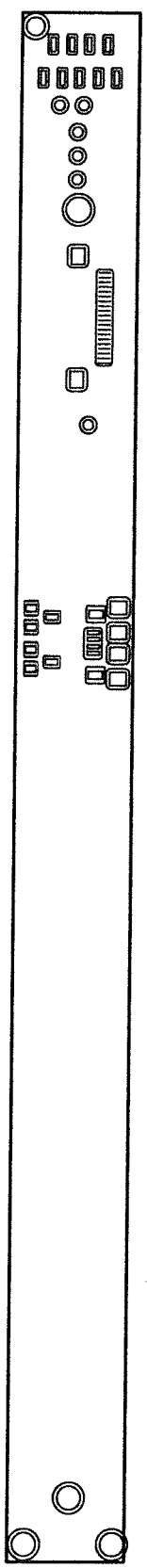
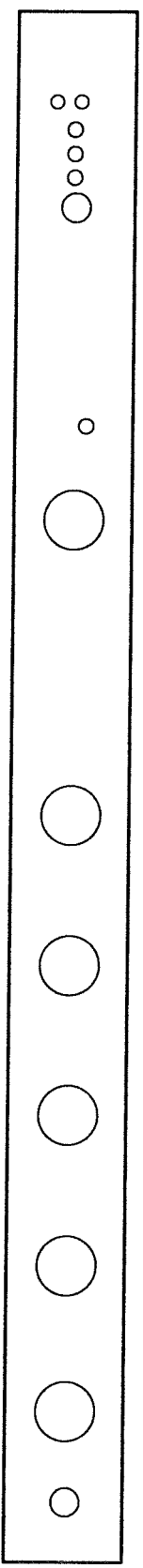
FIG. 29E  FIG. 29F

UV STERILIZATION SYSTEM AND DEVICE AND RELATED METHODS

RELATED APPLICATION

This application is a divisional of application Ser. No. 15/898,930 filed Feb. 19, 2018 which claims priority to Application No. 62/460,516 filed Feb. 17, 2017, and Application No. 62/460,347 filed Feb. 17, 2017, the entire subject matter of these applications is incorporated herein by reference in its entirety.

TECHNICAL FIELD

The present disclosure relates to the field of medical devices, and, more particularly, to sterilization device and related methods.

BACKGROUND

Health care facilities, such as hospitals, are under increasing financial pressure due to the global economic downturn. The determination of the federal and state payers to reduce health care payments, and the trend of private insurers to move their insured to high deductible plans. Also, government payment strategies now include reductions in payments for failures to achieve certain outcome and quality targets, a move that private insurers are sure to follow.

Infection controls is an increasingly important aspect of quality at health care facilities. Several approaches to maintaining the sterile field and sterilizing anything that comes in to contact with patient have been disclosed. For example, health care facilities have instituted rigorous hand washing and sterilization procedures, such as requiring hand sanitizer and hand washing before and after interacting with a patient.

As mobile device technology has permeated every aspect of society, in most health care facilities, many personnel carry one or more mobile devices. For example, a user may carry a typical voice communications handset for voice calls, and a tablet/laptop computing device for accessing patient records wirelessly. Of course, since these devices go everywhere the user goes, they accumulate biological contaminants and must be sterilized from time to time.

SUMMARY

Generally, a method for operating a UV sterilization device may include a housing defining a cavity therein, and having a door configured to permit access to the cavity, and a plurality of trays carried within the cavity, each tray configured to receive at least one mobile wireless communications device. The UV sterilization device may include a plurality of UV CBAs carried within the cavity respectively adjacent the plurality of trays, each UV CBA comprising a plurality of LED UV sources configured to irradiate the at least one mobile wireless communications device with UV radiation. The UV sterilization device may include a controller, and the method may include operating the controller to selectively power at least one of the plurality of UV CBAs for disinfecting the at least one mobile wireless communications device.

More specifically, each tray may comprise a material transparent to UV radiation. For example, the material may comprise quartz. The at least one mobile wireless communications device may include a radio frequency (RF) identification (ID) tag. Each UV sterilization device may further comprise an RF transmitter coupled to a controller and configured to energize the RFID tag, and the method may further comprise operating the controller to identify the at least one mobile wireless communications device based upon an RF signal from the RFID tag.

The method may also include operating each UV sterilization device to selectively power the at least one of the plurality of UV CBAs when the at least one mobile wireless communications device is detected on a respective tray. The method may comprise operating each UV sterilization device to unlock the door based upon a code received from a keypad. The method also may comprise operating each UV sterilization device to communicate with a wireless base station. The method may include operating each UV sterilization device to create positive air pressure in the cavity when the door is open.

Another aspect is directed to a method for operating a UV sterilization system comprising a server comprising a processor and memory coupled thereto, and a plurality of UV sterilization devices. Each UV sterilization device may include a housing defining a cavity therein, and having a door configured to permit access to the cavity, a plurality of trays carried within the cavity, each tray configured to receive at least one mobile wireless communications device, and a plurality of UV CBAs carried within the cavity respectively adjacent the plurality of trays. Each UV CBA may comprise a plurality of LED UV sources configured to irradiate the at least one mobile wireless communications device with UV radiation. Each UV sterilization device may comprise a transceiver configured to communicate with the server, and a controller. The method may include operating the controller to selectively power at least one of the plurality of UV CBAs for disinfecting the at least one mobile wireless communications device, and send at least one status message to the server. The method may include operating server to provide a web interface portal for accessing respective status information for the plurality of UV sterilization devices.

BRIEF DESCRIPTION OF THE DRAWINGS

FIGS. 28A-28M are images of circuit board layers for the backplane CBA in the UV sterilization device of FIGS. 6-7.

FIGS. 29A-29I are images of circuit board layers for the display in the UV sterilization device of FIGS. 6-7.

DETAILED DESCRIPTION

Figure 1:
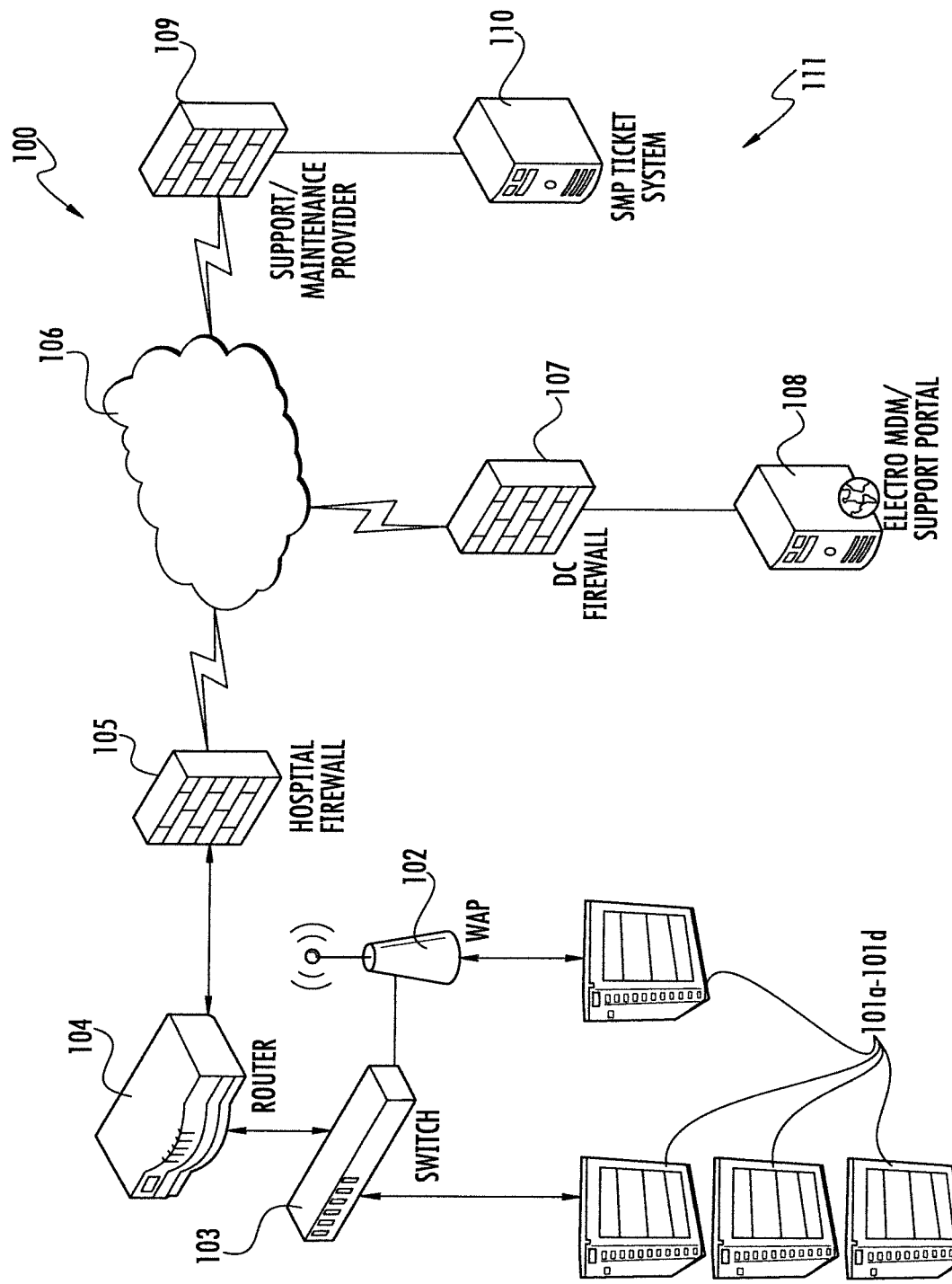
FIGS. 1-3 are schematic diagrams of varying embodiments of the UV sterilization system, according to the present disclosure.

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout, and base 100 reference numerals are used to indicate similar elements in alternative embodiments.

Referring initially to FIGS. 1 and 6-20B, a UV sterilization system 100 according to the present disclosure is now described. The UV sterilization system 100 illustratively includes a server 111 comprising a processor and memory coupled thereto, and a plurality of UV sterilization devices 101*a*-101*d*.

In this illustrated embodiment, the server 111 illustratively includes a support/maintenance provider 109 coupled to the Internet 105, a ticket system 110 coupled to the support/maintenance provider, a support portal 108, a firewall 107 coupled between the Internet and the support portal, a hospital firewall 106 coupled to the Internet, a router 104 coupled to the hospital firewall, a switch 103 coupled to the router, a wireless base station 102 coupled to the switch, and the plurality of UV sterilization devices 101*a*-101*d* coupled to one or more of the switch or the wireless base station. In other embodiments, the server 111 may be coupled to a local area network, serving only local clients.

Each UV sterilization device 101*a*-101*d* illustratively includes a housing 120 defining a cavity therein, and having a door 121 configured to permit access to the cavity. Each UV sterilization device 101*a*-101*d* illustratively includes a plurality of trays 131*a*-131*d* carried within the cavity, each tray configured to receive at least one mobile wireless communications device.

Each UV sterilization device 101*a*-101*d* illustratively includes a plurality of UV CBAs 125*a*-125*d* carried within the cavity respectively adjacent the plurality of trays 131*a*-131*d*. Each UV CBA 125*a*-125*d* illustratively includes a plurality of LED UV sources 135*a*-135l, 139*a*-139*e* configured to irradiate the at least one mobile wireless communications device with UV radiation. Each of the plurality of trays 131*a*-131*d* comprises a plurality of device bays for receiving devices of varying sizes and configurations (e.g. cell phones, tablets, laptops). As will be appreciated, the UV irradiation eliminates microbial contamination on the at least one mobile wireless communications device, i.e. effecting a disinfection or sanitizing process.

Each UV sterilization device 101*a*-101*d* illustratively includes a transceiver (e.g. WiFi, Bluetooth, ZigBee, cellular) 153 configured to communicate with the server 111, and a controller 144 configured to selectively power at least one of the plurality of UV CBAs 125*a*-125*d* for disinfecting the at least one mobile wireless communications device, and send at least one status message to the server. The server 111 is configured to contact respective users via e-mail or short message service (SMS) messages when needed. Advantageously, the UV sterilization device 101*a*-101*d* is more power efficient since unused trays 131*a*-131*d* are not irradiated.

Each tray 131*a*-131*d* comprises a material transparent to UV radiation. For example, the material comprises quartz. Indeed, since the plurality of LED UV sources 135*a*-135l have a narrow emission spectrum, the material need only be transparent to the emission spectrum and not the entire UV band. Helpfully, since there are no UV shadows on the device, this permits for 360 degree irradiation of the at least one mobile wireless communications device.

The server 111 is be configured to provide a web interface portal for accessing respective status information for the plurality of UV sterilization devices 101a-101d. The at least one mobile wireless communications device includes an RFID tag. The UV sterilization device 101a-101d illustratively includes an RF transmitter (e.g. an ultra high frequency (UHF) transmitter) 115 coupled to the controller 144 and configured to energize the RFID tag. The controller 144 is configured to identify the at least one mobile wireless communications device based upon an RF signal from the RFID tag. The controller 144 is configured to selectively power the at least one of the plurality of UV CBAs 125a-125d when the at least one mobile wireless communications device is detected on a respective tray. In these embodiments, each mobile wireless communications device would have a passive RFID tag, for example, an adhesive backed RFID tag.

Advantageously, the RF transmitter 115 is configured to operate in a closed loop system, and segregates device bays in each tray 131a-13d into an RF zone to solve for device orientation and placement. In fact, some embodiments may include a plurality of RF transmitters, which are activated in sequence based upon the detected placement and number of mobile wireless communications devices within the cavity. In these embodiments, the plurality of RF transmitters may operate with circular polarization.

Also, this identification feature permits the UV sterilization device 101a-101d to maintain an accurate real-time inventory of the mobile wireless communications devices within the plurality of trays 131a-13d. This may aid in providing for reduction of device theft and loss. Further, the disinfection status and frequency of each mobile wireless communications device is monitored and reported back to the server 111.

The UV sterilization device 101a-101d may further comprise a keypad carried on an external surface of the housing 120 and coupled to the controller 144. The controller 144 is configured to unlock the door 121 based upon a code received from the keypad. Since each user has a unique code to open the door 121, the UV sterilization device 101a-101d can keep track of which user opened the door and verify the proper device was removed. Indeed, if the wrong device is removed, the UV sterilization device 101a-101d may cause the server 111 to send a notification to the user.

In other embodiments, the UV sterilization device 101a-101d may further comprise a near field communications (NFC) device configured to communicate with the mobile wireless communications device. Helpfully, the NFC device would be accessible from the exterior of the UV sterilization device 101a-101d and permit the user to tap the mobile wireless communications device for access. In other words, the UV sterilization device 101a-101d may identify the mobile wireless device and open the door 121 when the NFC device detects an authorized device.

The UV sterilization device 101a-101d may further comprise a charging port (e.g. universal serial bus) carried within the cavity and configured to charge the at least one mobile wireless communications device. Also, in the cavity, the housing 120 comprises a plurality of cable management devices for reducing potential UV shadow of charging cables.

Helpfully, the UV sterilization device 101a-101d use of LED UV light sources creates less waste infrared (IR), i.e. heat, energy, keeping the at least one mobile wireless communications device at a lower temperature during the disinfection process. In prior approaches that used incandescent UV sources, the at least one mobile wireless communications device would be heated with waste IR energy, making simultaneous charging undesirable or impossible.

The housing 120 comprises opposing front and back sides, the front side defining the door 121. The UV sterilization device 101a-101d may further comprise a backplane CBA 130 carried by the back side and configured to receive and power the plurality of UV CBAs 125a-125d. In fact, the plurality of UV CBAs 125a-125d are readily removable and coupled to the backplane CBA via a slot connection. In the illustrated embodiment, each UV CBAs 125a-125d illustratively includes a circuit board 134, 137 comprising a connector tab 136, 138 to be received by respective slots in the backplane CBA 130, and a carrying housing 141 coupled to the circuit board. The carrying housing 141 illustratively includes side edges to be received by the slots within the sides of the cavity of the housing 120.

The UV sterilization device 101a-101d illustratively includes a positive air pressure source 126 (e.g. an electrical fan) carried by the housing and configured to create positive air pressure in the cavity when the door 121 is open. Helpfully, this causes an outflow of air when the door 121 is open and prevents particulate contaminants from entering the cavity, which can cause UV micro-shadowing during the disinfection process. In some embodiments, the positive air pressure source 126 illustratively includes an air filter (e.g. HEPA filter) to filter incoming air, preventing unintended ingestion of particulate matter from the positive air pressure source. In some embodiments, the housing 120 comprises a plurality of adjustable feet on a bottom exterior surface.

The UV sterilization device 101a-101d may further comprise a sensor (e.g. Hall effect sensor) coupled to the controller 144 and configured to detect a state of the door 121. Accordingly, when the door 121 is opened, the controller sends a status update to the server 111. The UV sterilization device 101a-101d illustratively includes a latch 133, and an electromechanical solenoid 132 cooperating therewith and coupled to the controller 144. The electromechanical solenoid 132 is configured secured the door 121. In embodiments where the UV sterilization device 101a-101d has a keypad for coded entry, the controller 144 would include a user identifier in the status message, and would activate the solenoid 132 to open the door 121. In these embodiments, the door 121 is biased to open outward with a spring, for example. In some embodiments, the controller 144 may activate a sound indicator to alert a user to when the door 121 is open for a period greater than a set timeout period. In some embodiments, the door 121 may be totally automated and motorized to open and close.

The UV sterilization device 101a-101d may further comprise a data communications bus coupled to the controller 144, and a plurality of wired data ports (e.g. Ethernet) 129 coupled to the data communications bus. The UV sterilization device 101a-101d illustratively includes a display 122 coupled to the controller 144 and configured to present operational indicators to the user. In some embodiments, the keypad may be integrated with the display 122. The UV sterilization device 101a-101d illustratively includes a pair of handles 123a-123b on sides of the housing 120 and configured to permit easy handling. The UV sterilization device 101a-101d illustratively includes a plurality of indicators 124a-124b for indicating a charging status for the at least one mobile wireless communications device. As shown, the door 121 illustratively includes a plurality of light conduits coupled to internal indicator LEDs.

The UV sterilization device 101a-101d illustratively includes a wired port 129 (e.g. universal serial bus (USB) B type) configured to permit access to the controller 144 for firmware updates and maintenance, a power connector 128 configured to receive a power cord, and a power switch 127 configured to power toggle the device. The UV sterilization device 101a-101d illustratively includes a light louver 140 configured to permit air to flow out of cavity, but prevent UV radiation from leaking out. The UV sterilization device 101a-101d illustratively includes a plurality of wall mount openings 143a-143d configured to anchor the housing 120 to a wall.

Figure 27:
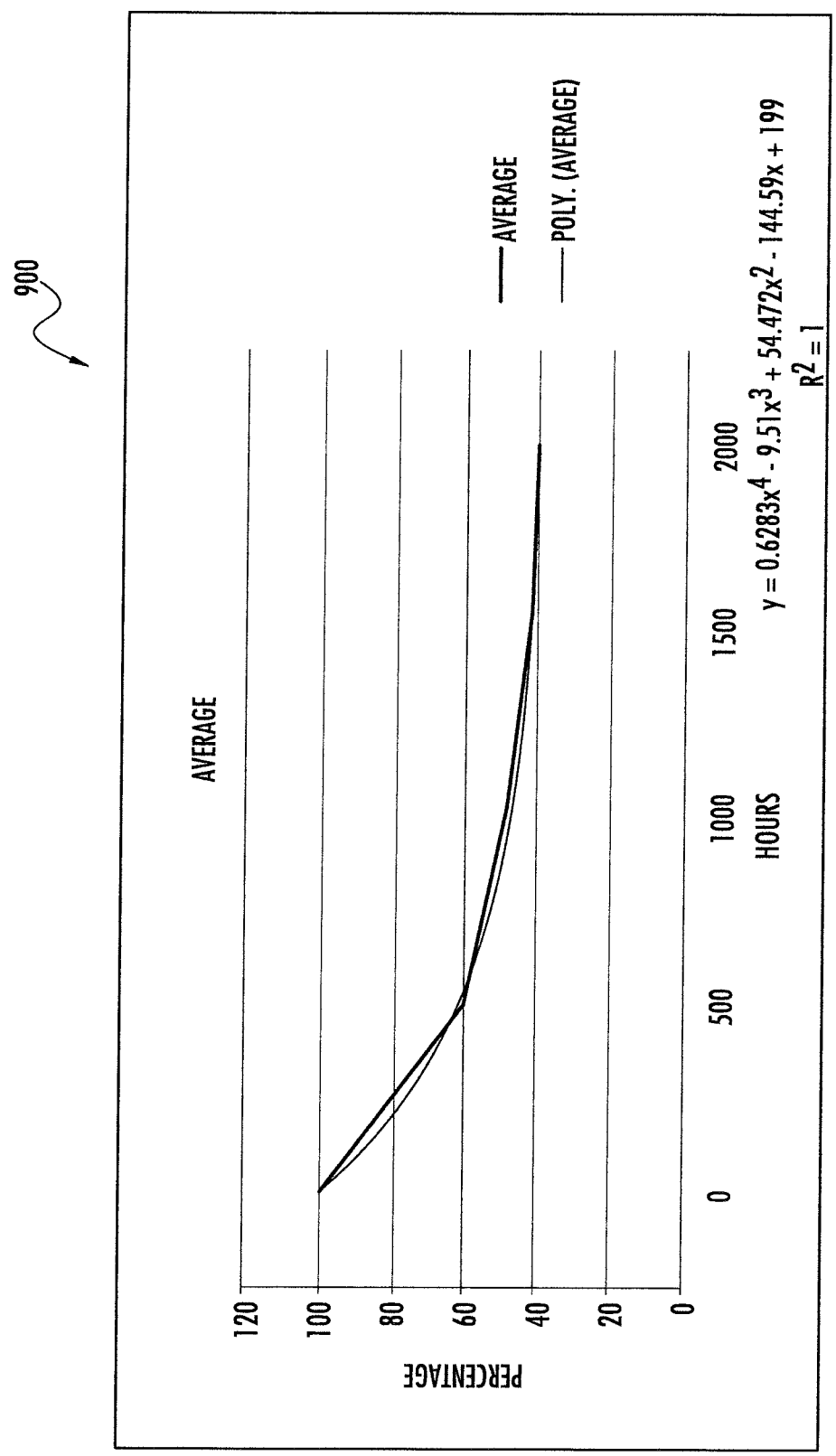
FIG. 27 is a diagram showing UV LED aging in an embodiment of the UV sterilization device, according to the present disclosure.
Figure 28A:
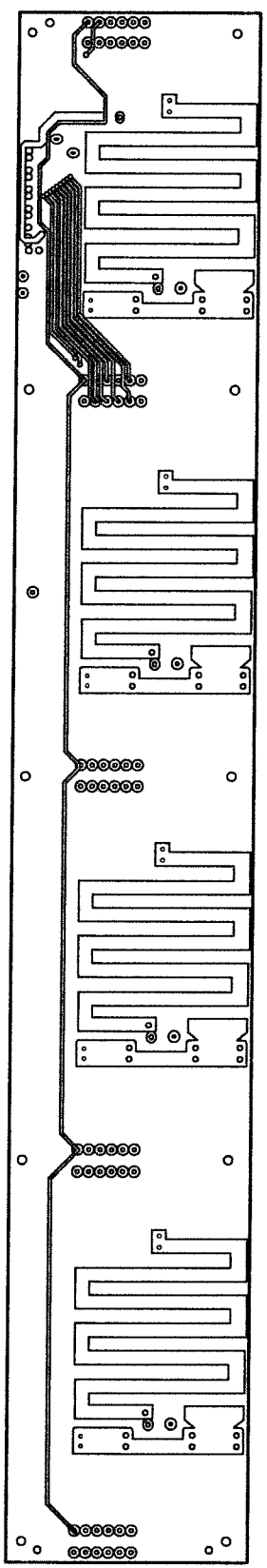
Figure 28B:
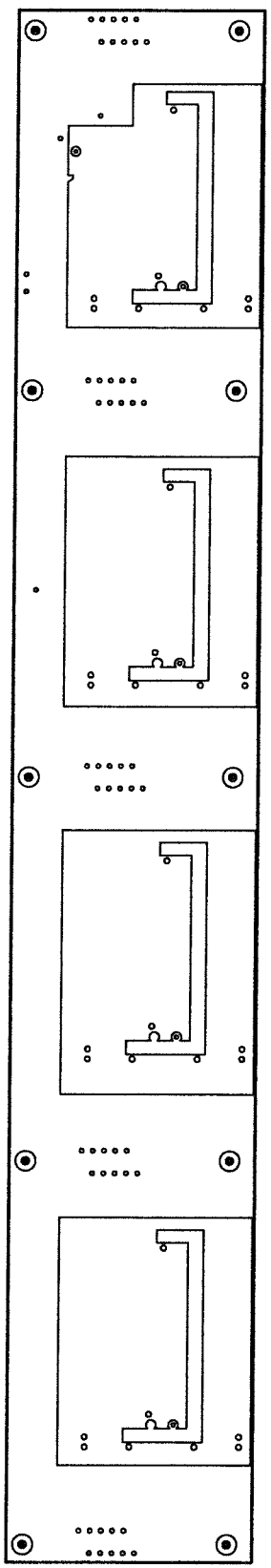
Figure 28E:
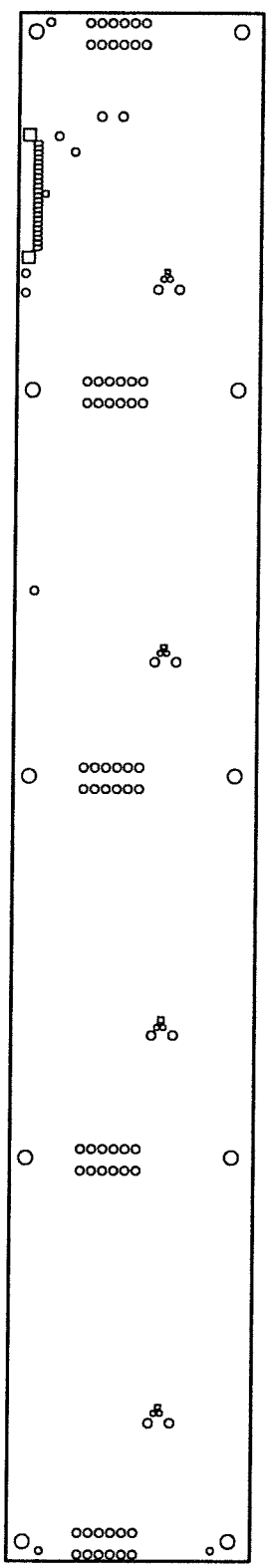
Figure 28F:
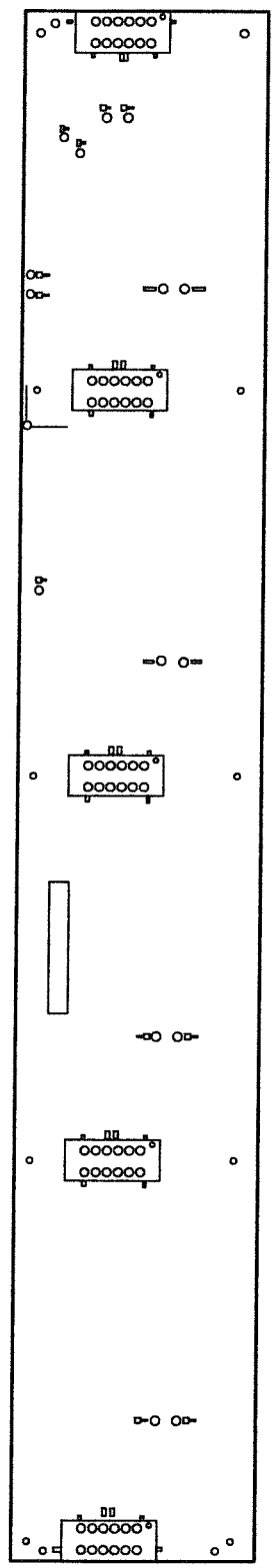
Figure 28G:
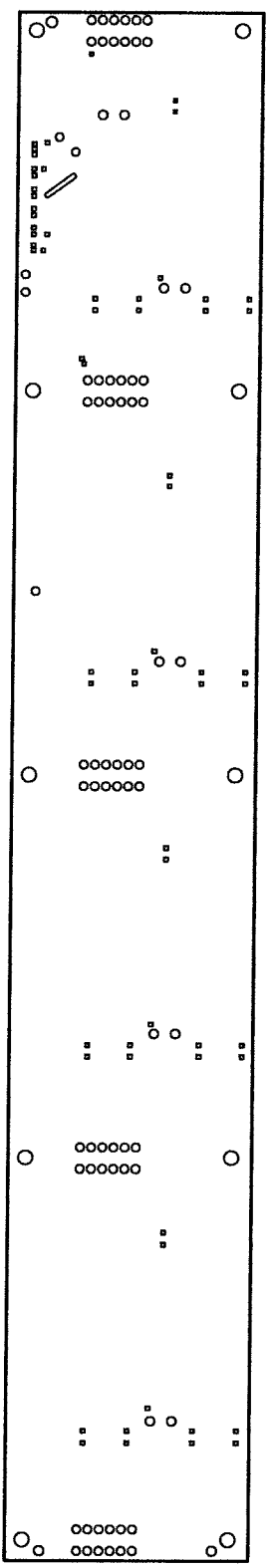
Figure 28H:
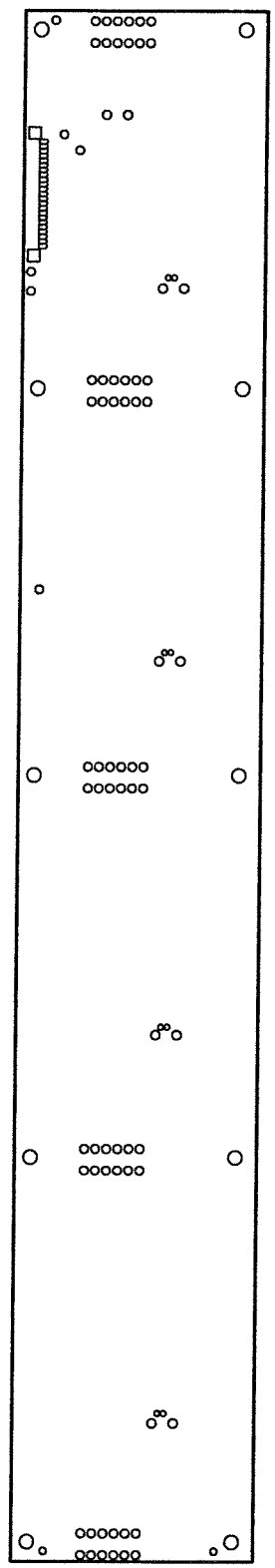
Figure 28I:
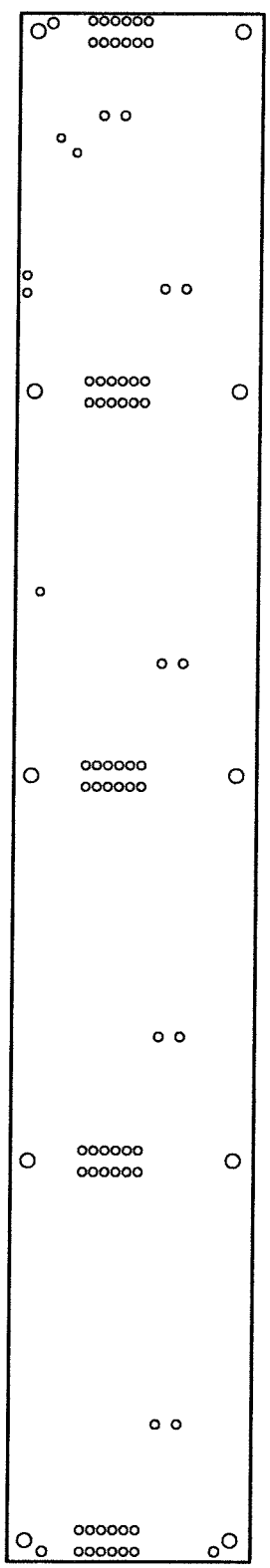
Figure 28J:
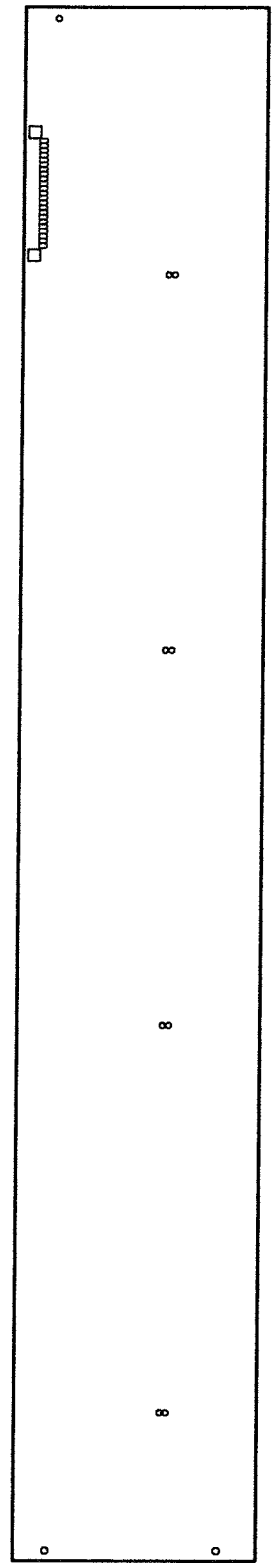
Figure 28K:
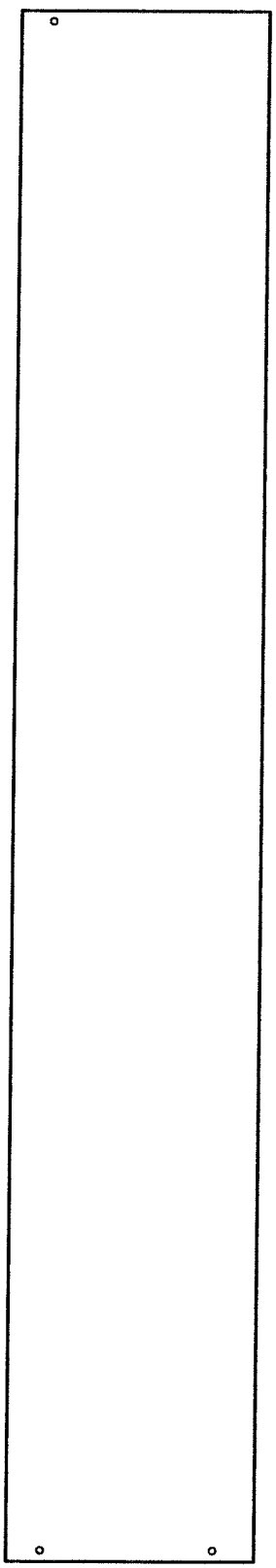
Figure 28L:
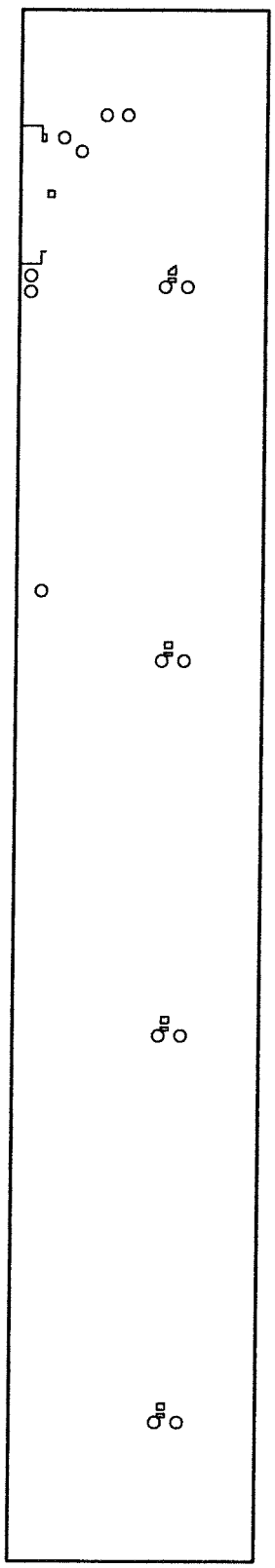
Figure 28M:
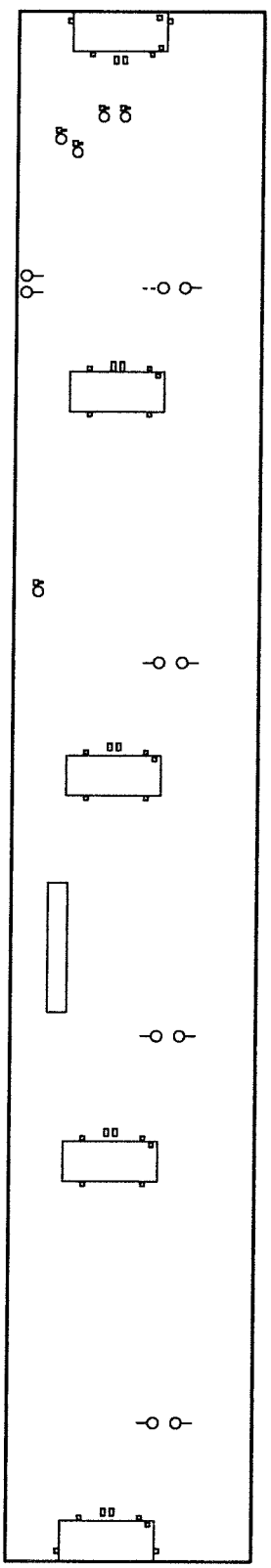
Figure 29A:
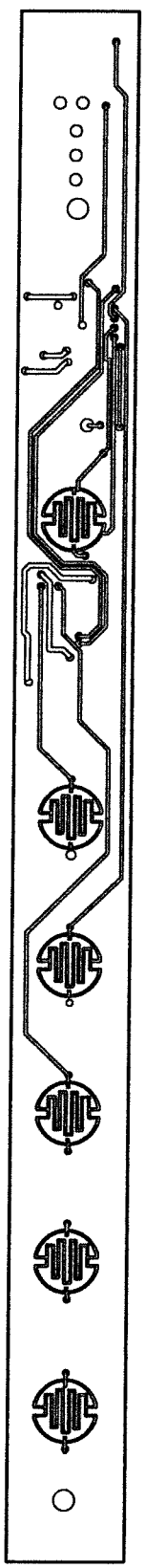
Figure 29B:
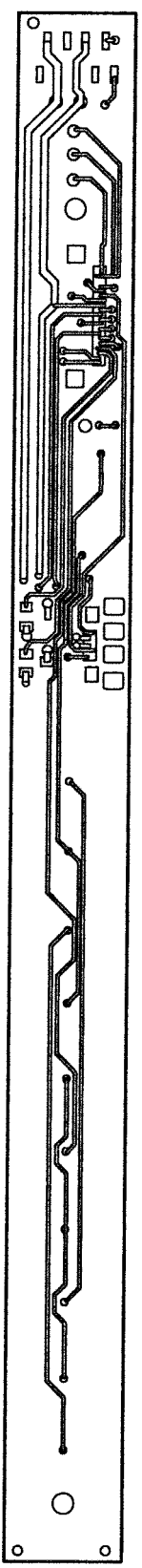
Figure 29C:
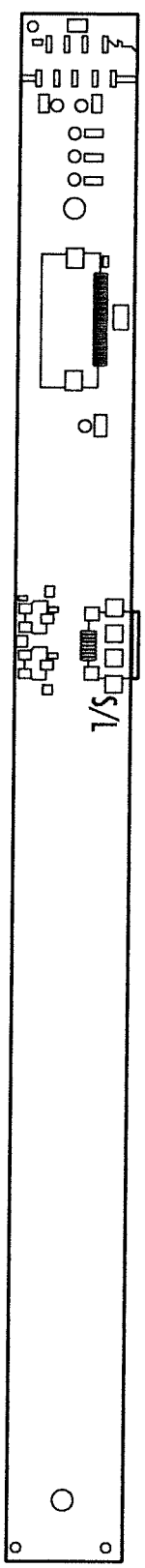
Figure 29D:
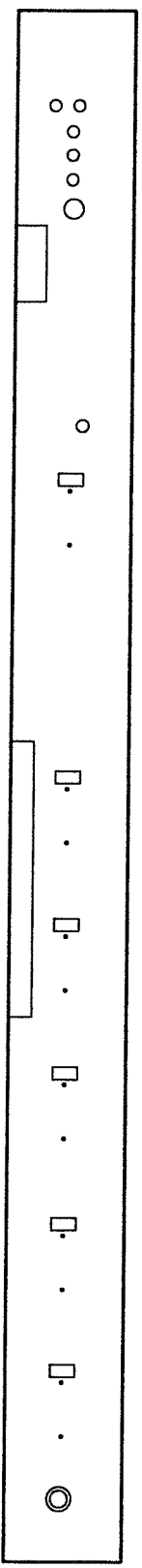
Figure 29G:
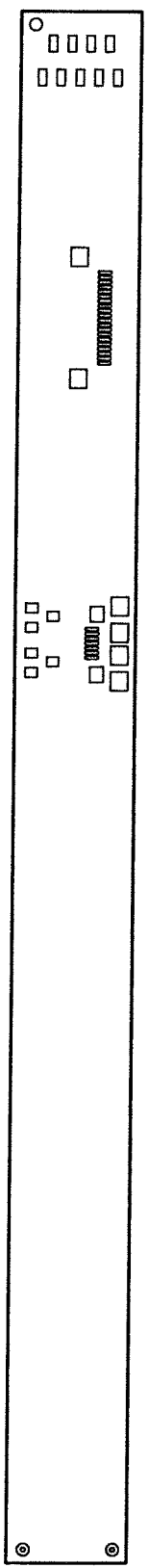
Figure 29H:
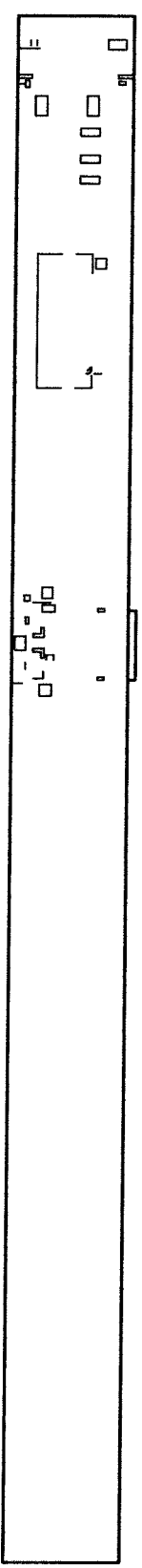
Figure 29I:
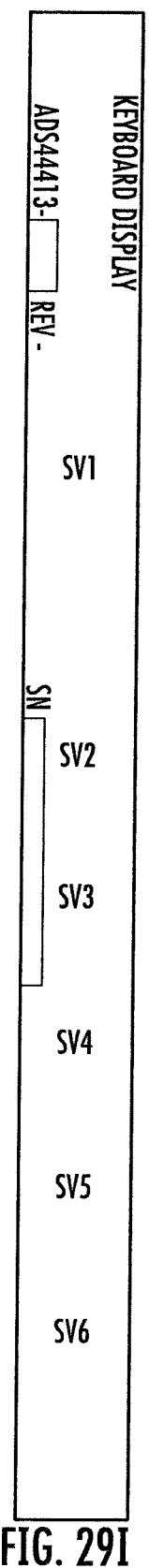

The UV sterilization device 101a-101d illustratively includes an LED driver circuit configured to drive the UV LEDs with a stepped waveform, which provides for a constant operation current and a narrow emission spectrum. This also provides for a long lifespan for the UV LEDs, on the order of 5,000 hours. Moreover, the controller 144 is configured to monitor the wear on the UV LEDs and alert the server 11 when replacement is needed. In particular, the wear on the UV LEDs is based upon a known degradation curve, as show in diagram 900 (FIG. 27).

Another aspect is directed to a method for operating a UV sterilization device 101a-101d including a housing 120 defining a cavity therein, and having a door 121 configured to permit access to the cavity, and a plurality of trays 131a-131d carried within the cavity, each tray configured to receive at least one mobile wireless communications device. The UV sterilization device 101a-101d may include a plurality of UV CBAs 125a-125d carried within the cavity respectively adjacent the plurality of trays, each UV CBA comprising a plurality of LED UV sources 135a-135l configured to irradiate the at least one mobile wireless communications device with UV radiation. The UV sterilization device 101a-101d may include a controller 144, and the method may include operating the controller to selectively power at least one of the plurality of UV CBAs 125a-125d for disinfecting the at least one mobile wireless communications device.

Another aspect is directed to a method for operating a UV sterilization system 100 comprising a server 111 comprising a processor and memory coupled thereto, and a plurality of UV sterilization devices 101a-101d. Each UV sterilization device 101a-101d may include a housing 120 defining a cavity therein, and having a door 121 configured to permit access to the cavity, a plurality of trays 131a-131d carried within the cavity, each tray configured to receive at least one mobile wireless communications device, and a plurality of UV CBAs 125a-125d carried within the cavity respectively adjacent the plurality of trays. Each UV CBA 125a-125d may comprise a plurality of LED UV sources 135a-135l configured to irradiate the at least one mobile wireless communications device with UV radiation. Each UV sterilization device 101a-101d may comprise a transceiver 153 configured to communicate with the server 111. The method may include operating a controller 144 to selectively power at least one of the plurality of UV CBAs 125a-125d for disinfecting the at least one mobile wireless communications device, and send at least one status message to the server 111. The method may include operating the server 111 to provide a web interface portal for accessing respective status information for the plurality of UV sterilization devices 101a-101d.

Advantageously, controller 144 is configured with a custom firmware. This is advantageous in the healthcare facility application for the following reasons. Since prior approaches may leverage existing operating systems (OSs) to cut costs and provide built-in functionality, they are rarely updated once put into use as medical devices, which can lead to critical unpatched vulnerabilities. This may cause security risks to local networks in healthcare facilities.

The custom firmware of the controller 144 addresses this issue, yet includes a Transmission Control Protocol/Internet Protocol (TCP/IP) stack to communicate on typical networks. In particular, the controller is configured to perform one-time handshakes with the server 111, the switch 103, and/or the wireless base station 102. The controller is configured to provide for media access control address (MAC address) authentication, so that the handshake occurs only with proper devices.

Also, the UV sterilization device 101a-101d illustratively includes a plurality of image sensors configured to detect a number and location of mobile wireless communications devices placed in the cavity. Advantageously, the controller 144 then activates needed antennas of the RF transmitter 115 to activate the respective RFID tag on the device. For example, the plurality of image sensors may each comprise an RGB color sensor, or a proximity sensor.

Figure 2:
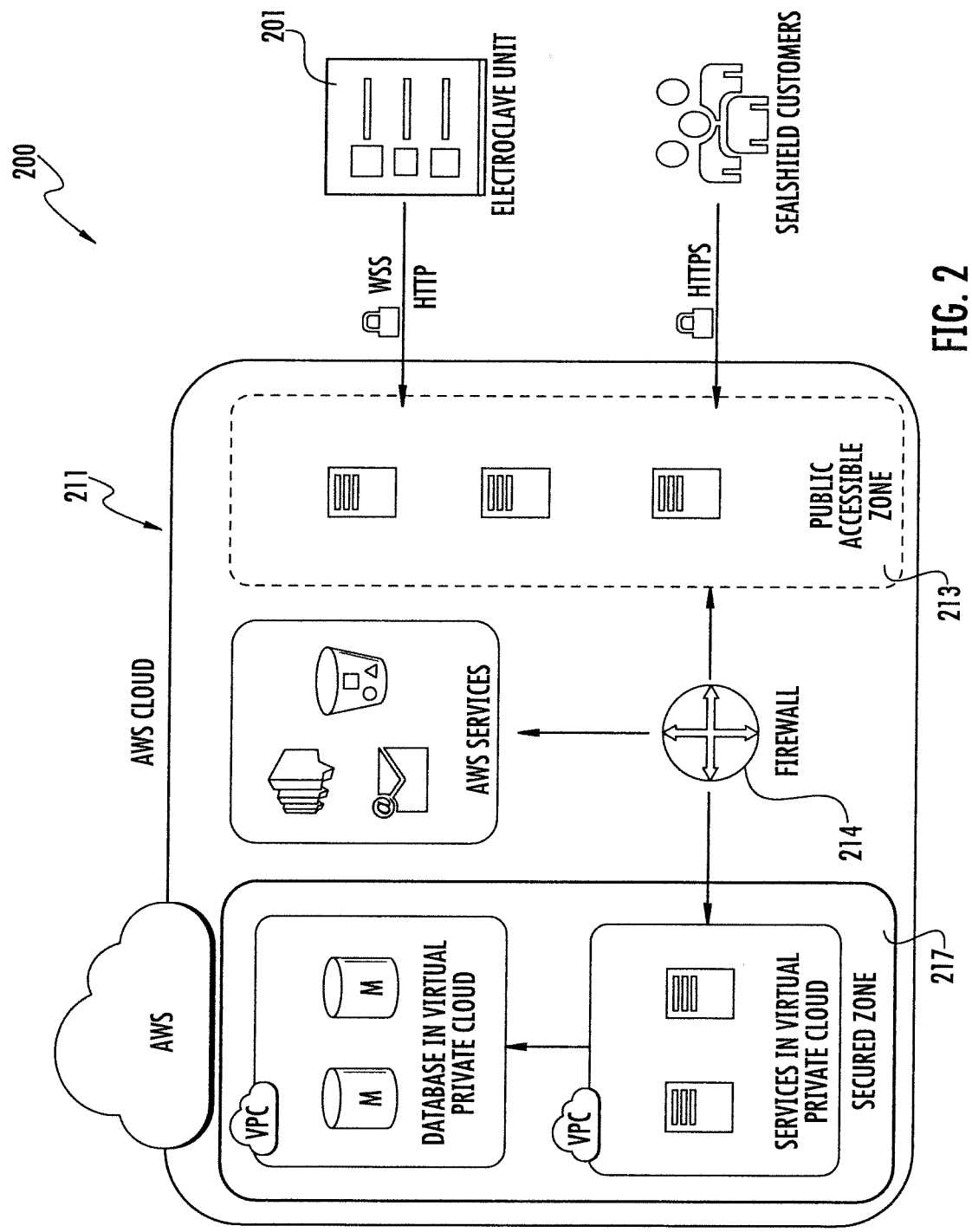

Referring now additionally to FIG. 2, another embodiment of the UV sterilization system 100 is now described. In this embodiment of the UV sterilization system 200, those elements already discussed above with respect to FIG. 1 are incremented by 100 and most require no further discussion herein. This embodiment differs from the previous embodiment in that this UV sterilization system 200 illustratively includes the server 211 as a cloud based service provided by Amazon Web Services. The server 211 illustratively includes a public accessible zone 212 providing the web interface, a secured zone 212, and a firewall 214.

Figure 3:
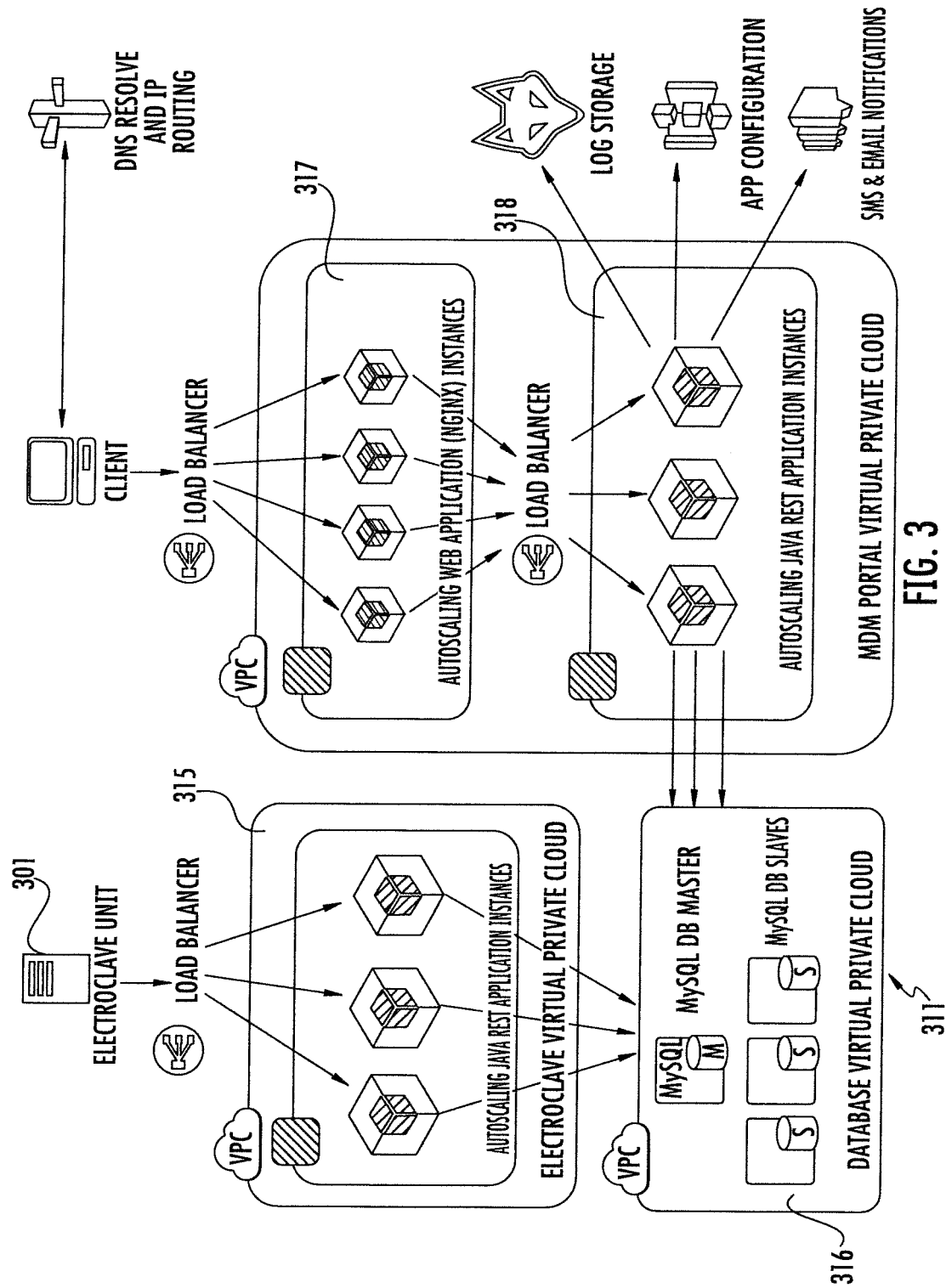
Figure 4:
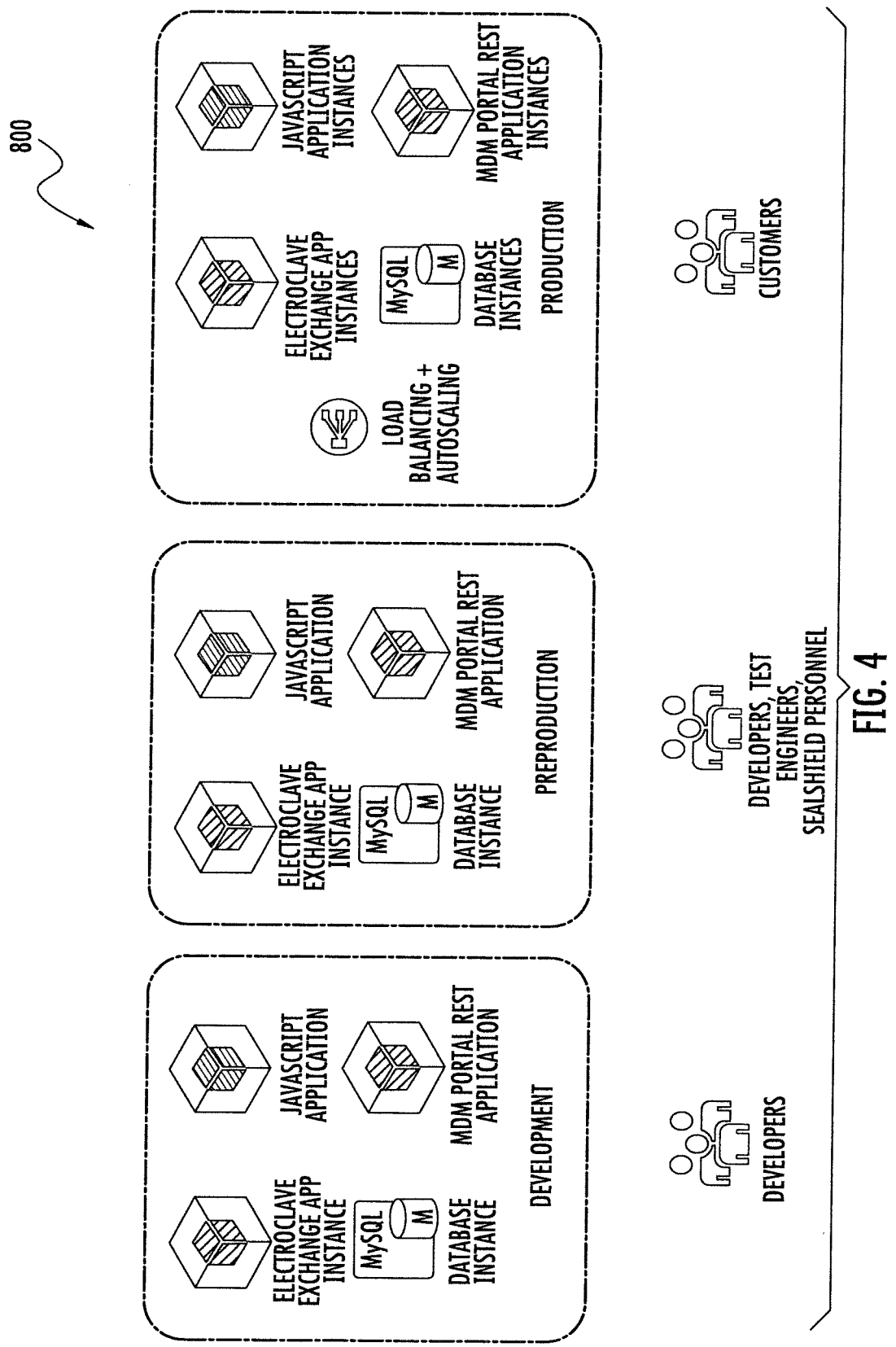
FIGS. 4-5 are diagrams of illustrating structure of the UV sterilization system, according to the present disclosure.
Figure 5:
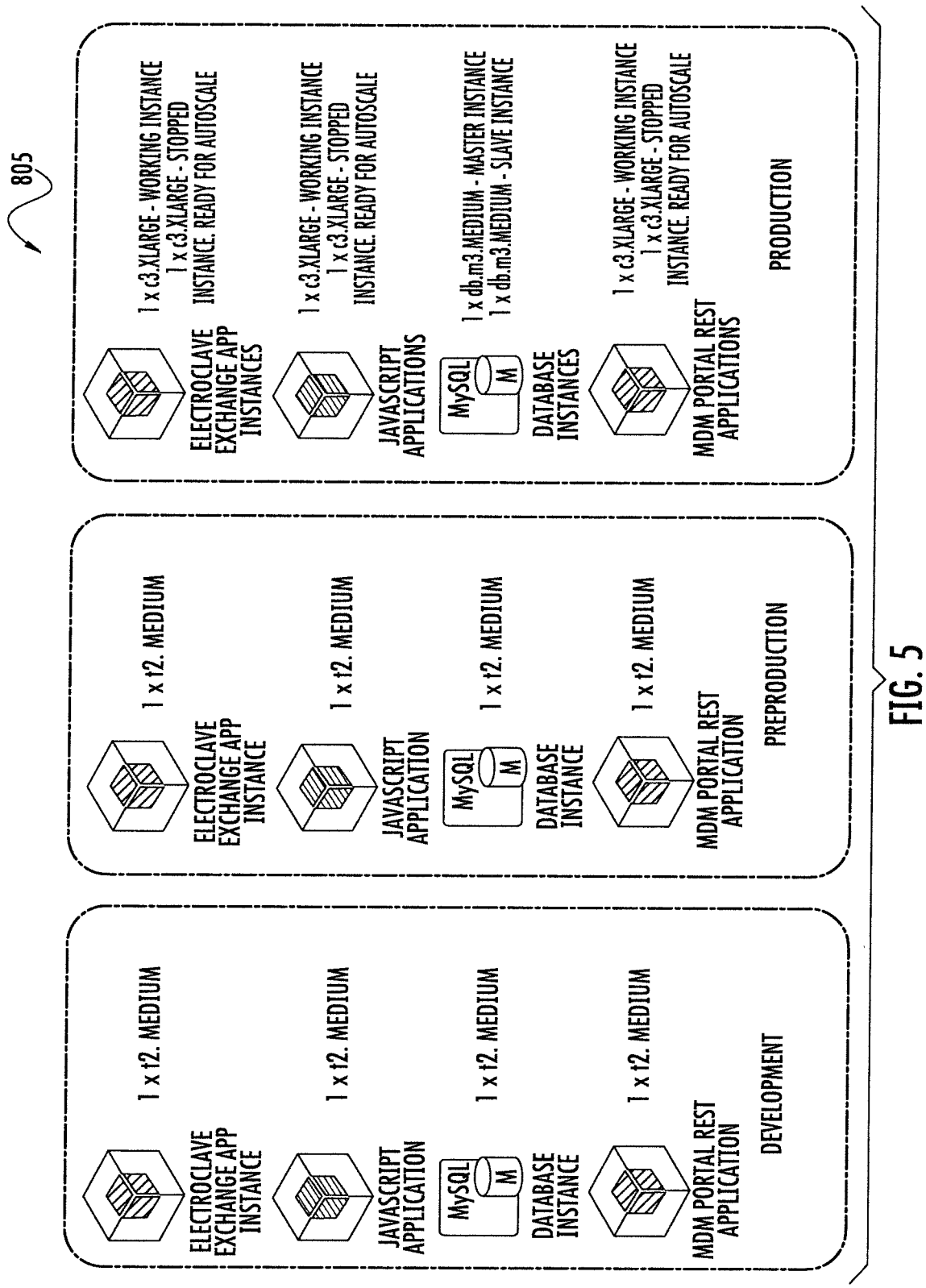
Figure 6:
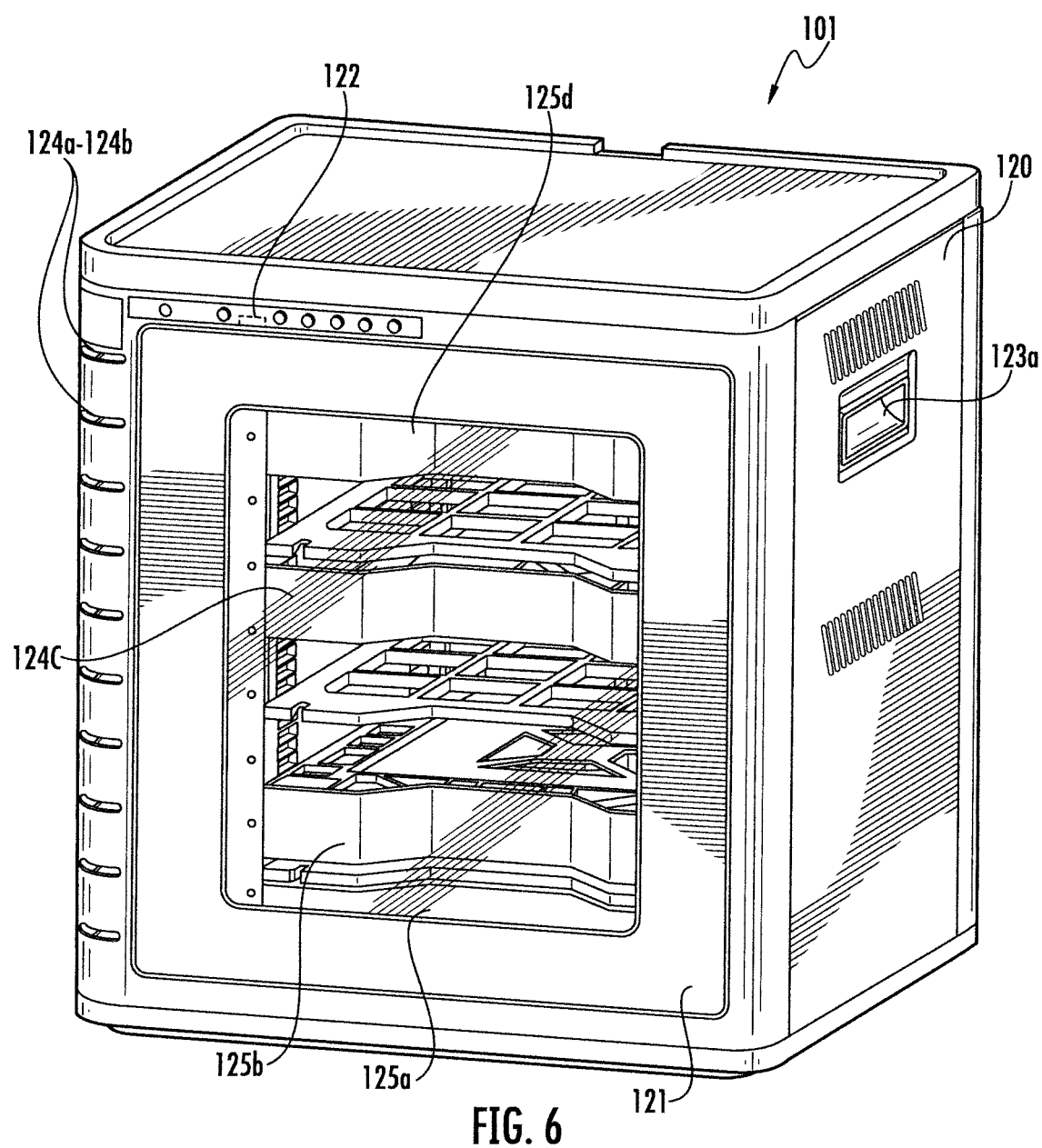
FIGS. 6 and 7 are perspective front and back views of a UV sterilization device, according to the present disclosure.
Figure 7:
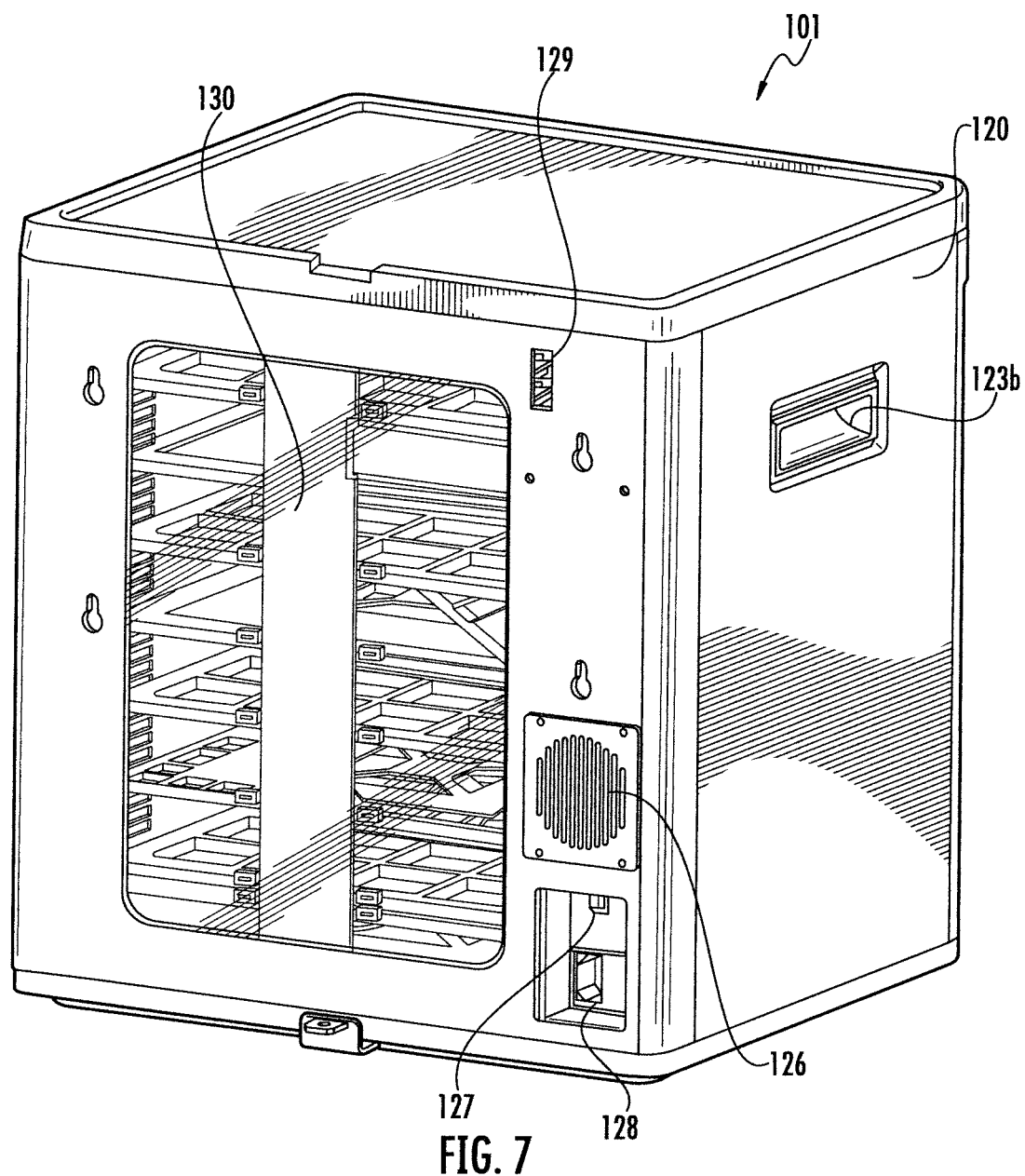
Figure 8:
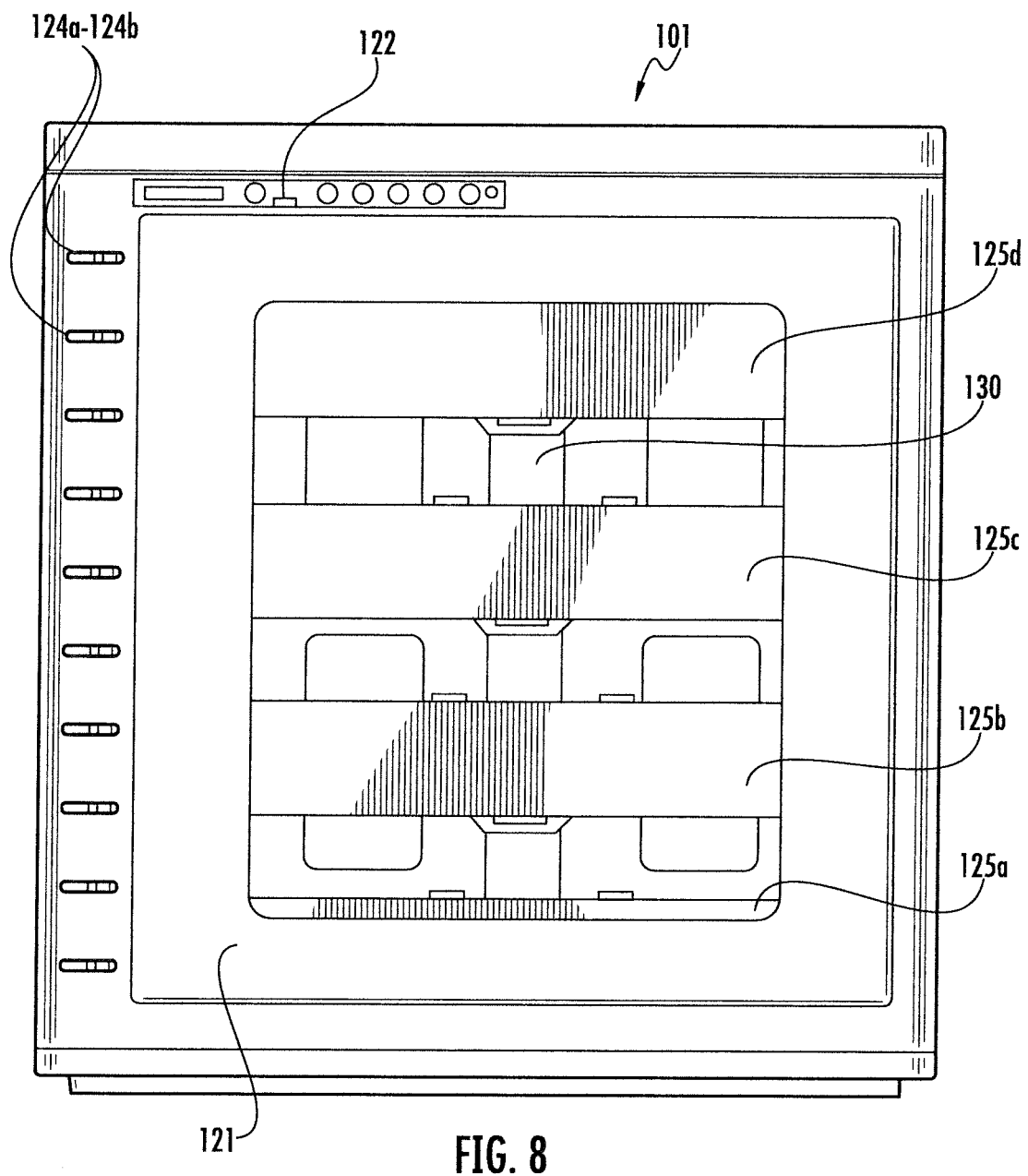
FIG. 8 is a front elevational view of the UV sterilization device of FIGS. 6-7.
Figure 9:
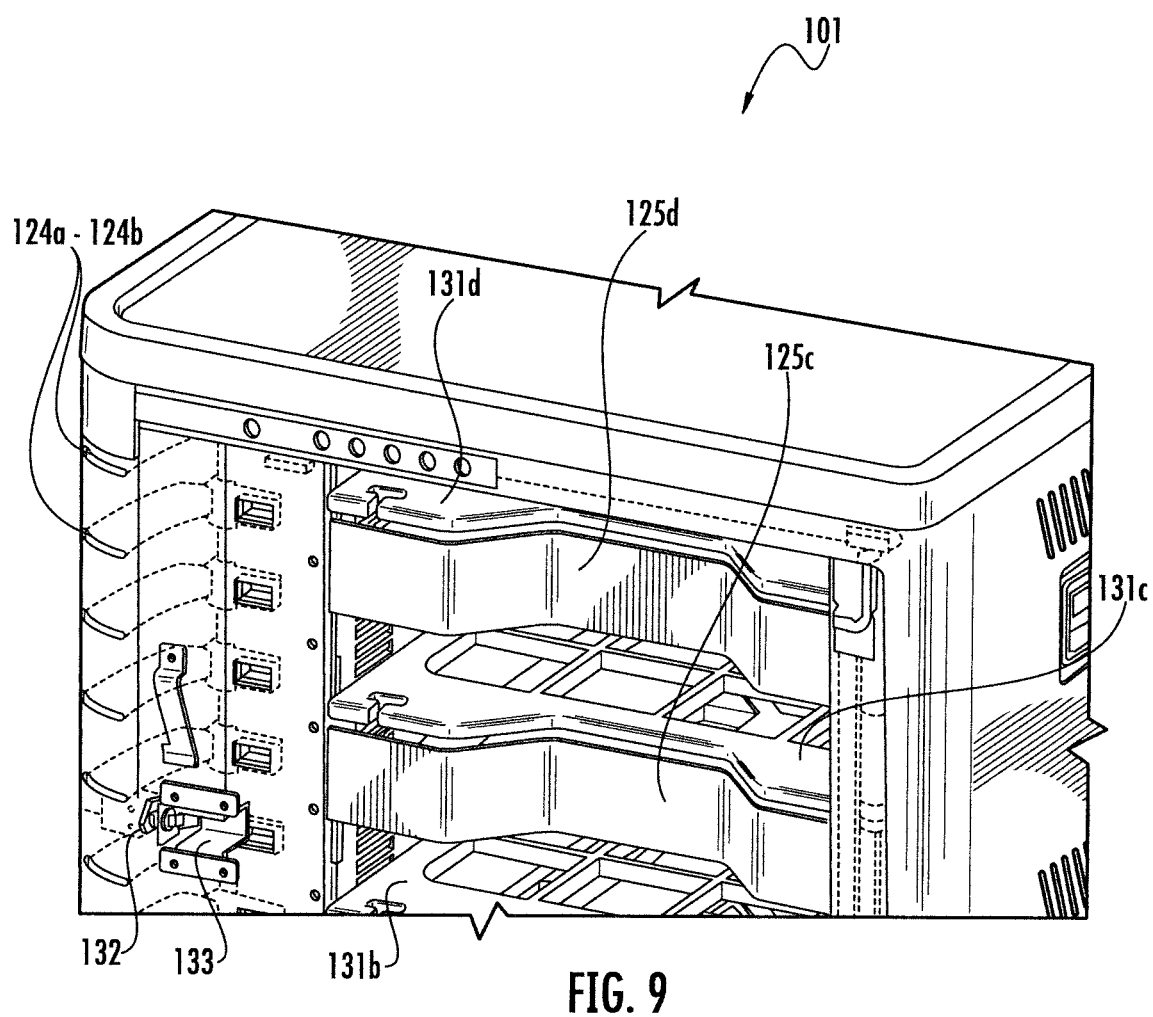
FIG. 9 is a partial front perspective view of the UV sterilization device of FIGS. 6-7 with the door removed.
Figure 10:
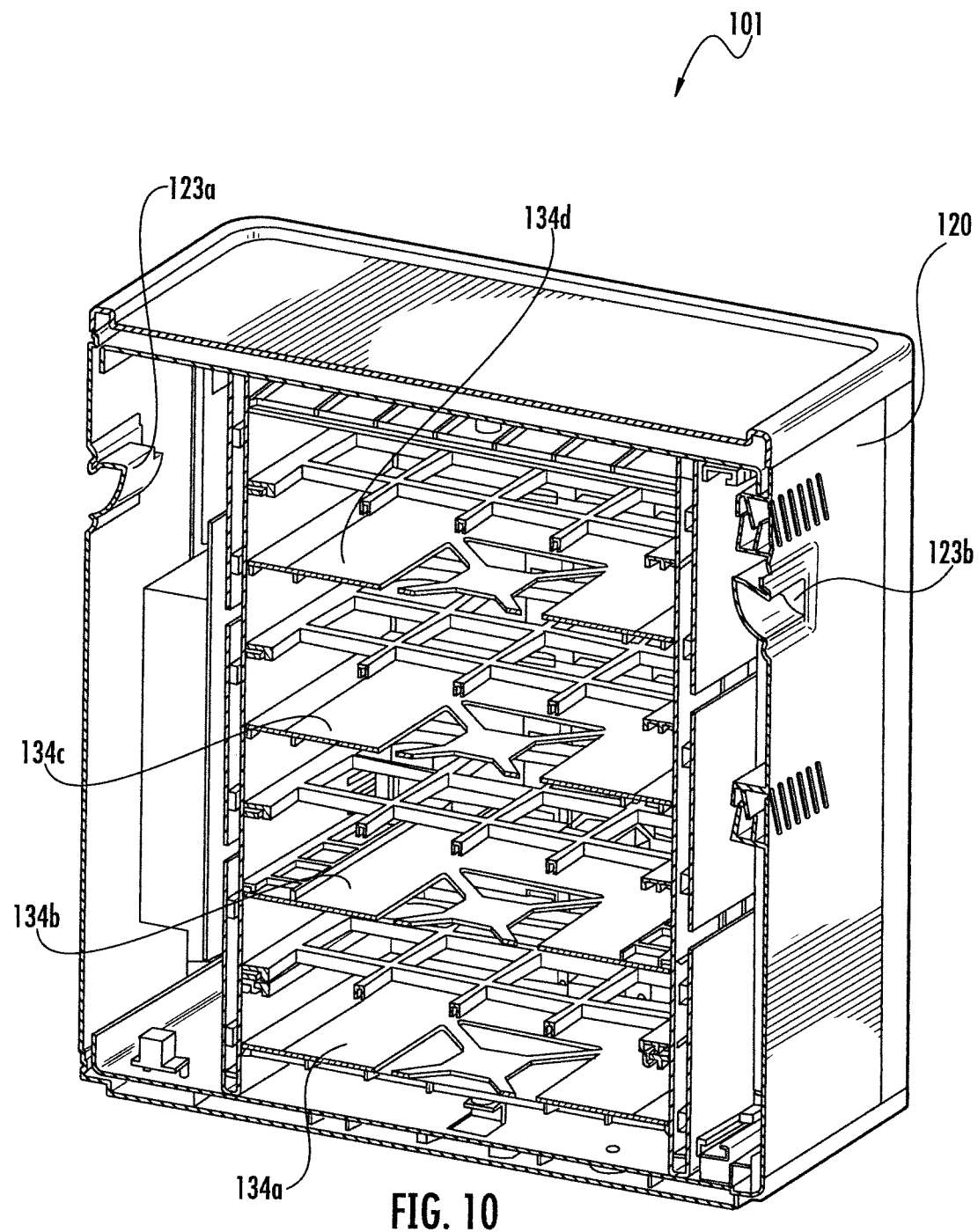
FIG. 10 is a section view of the UV sterilization device of FIGS. 6-7.
Figure 11:
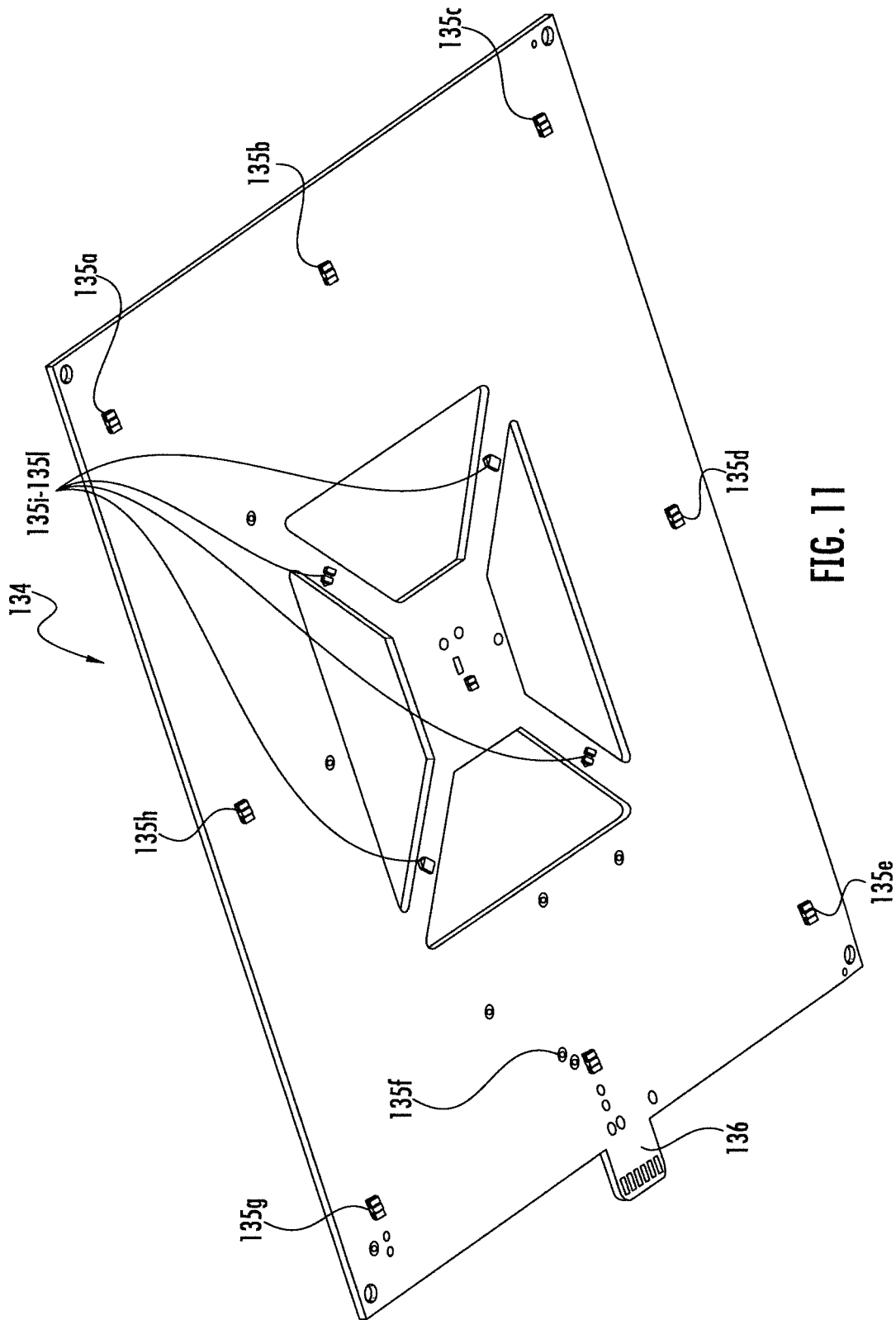
FIGS. 11-13 are perspective and top plan elevational views of UB circuit boards from the UV sterilization device of FIGS. 6-7.
Figure 12:
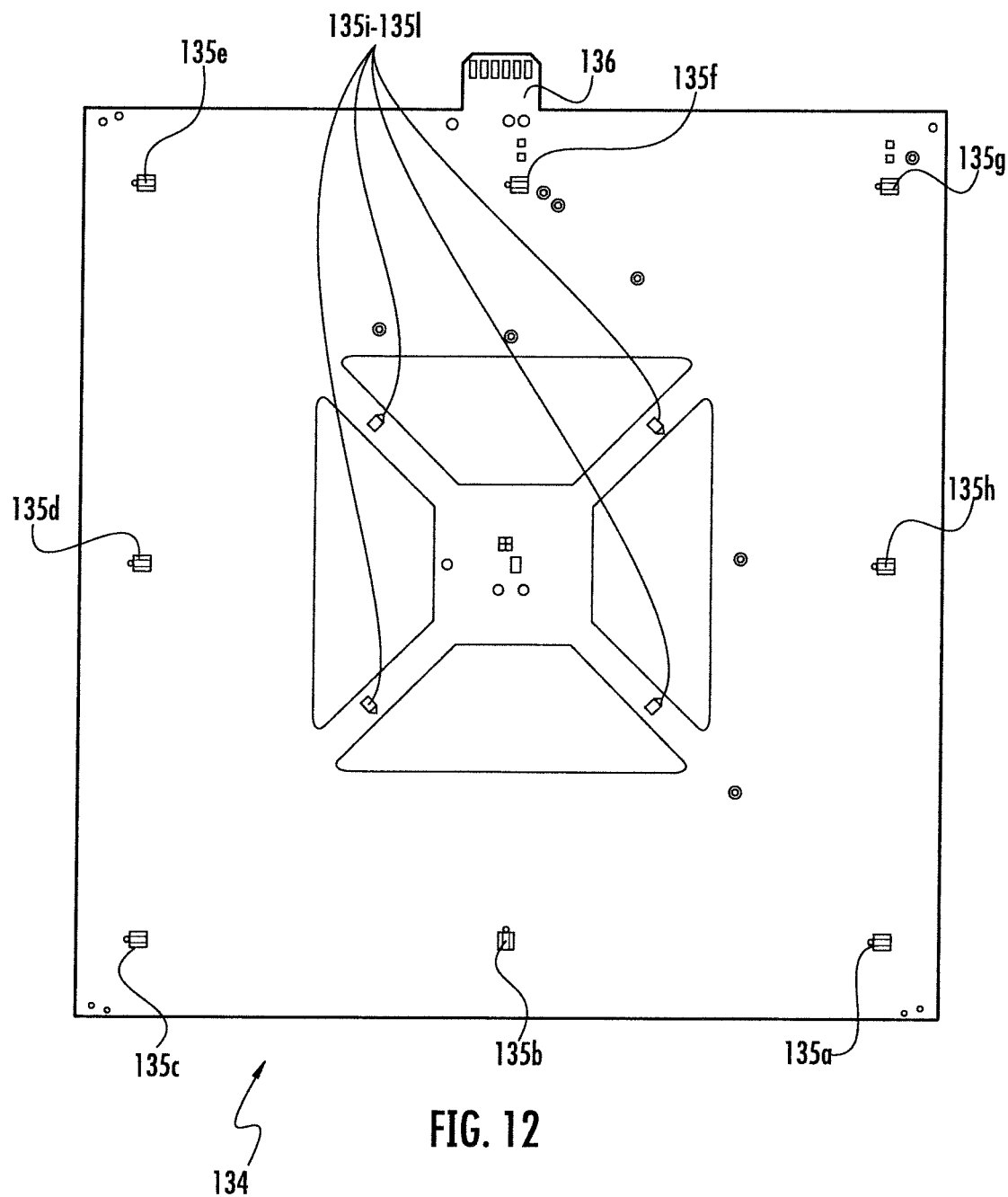
Figure 13:
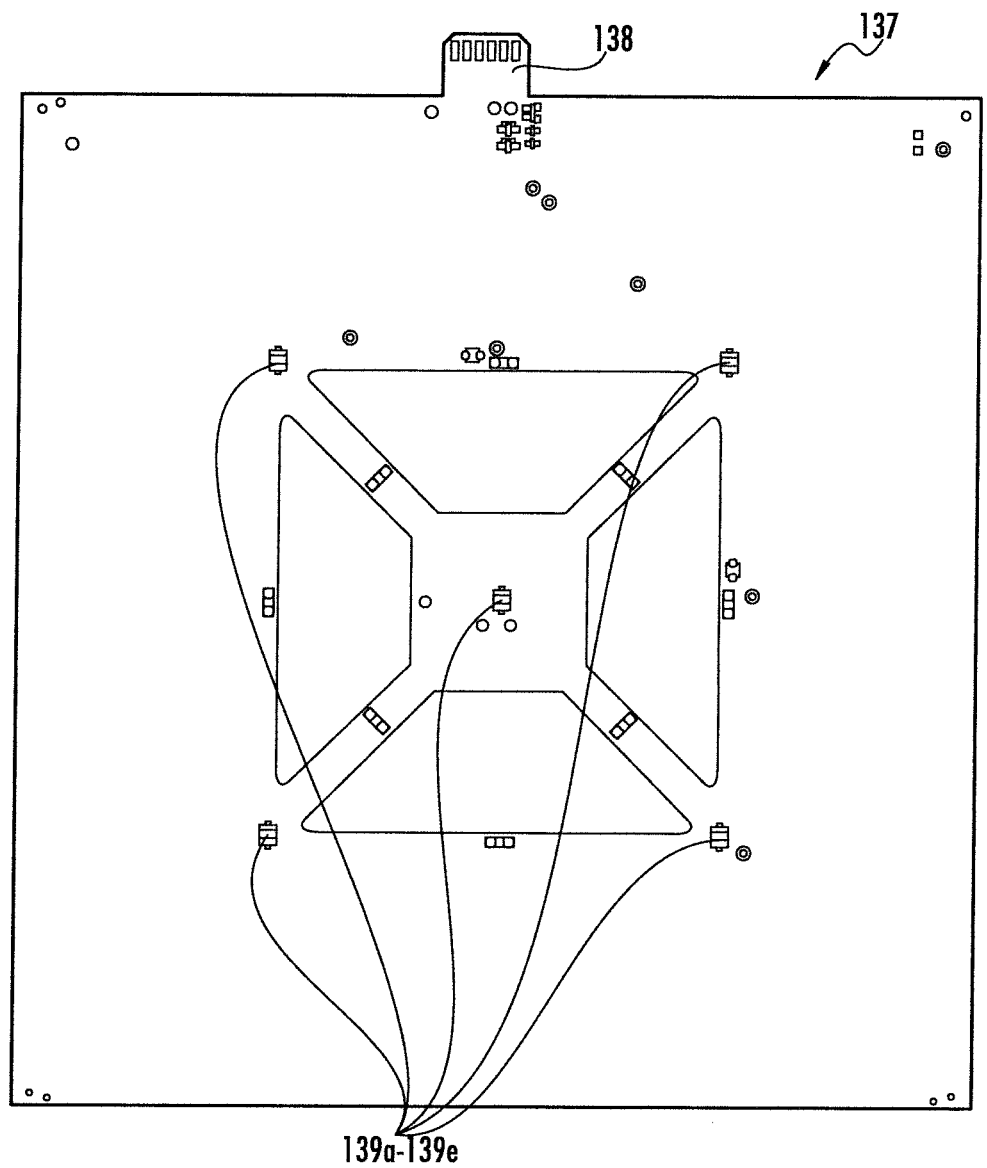
Figure 14:
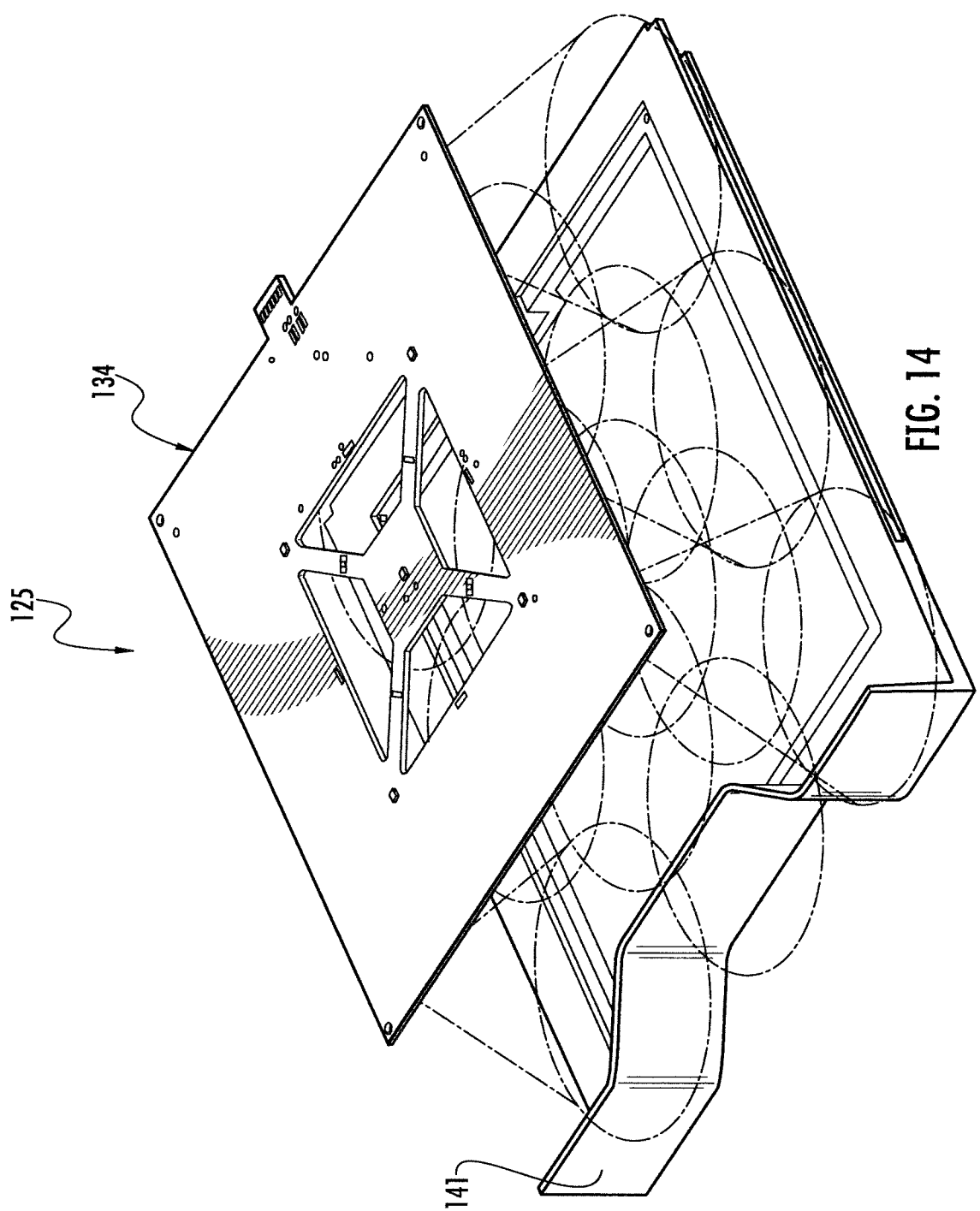
FIG. 14 is a perspective view of a UV CBA from the UV sterilization device of FIGS. 6-7.
Figure 15:
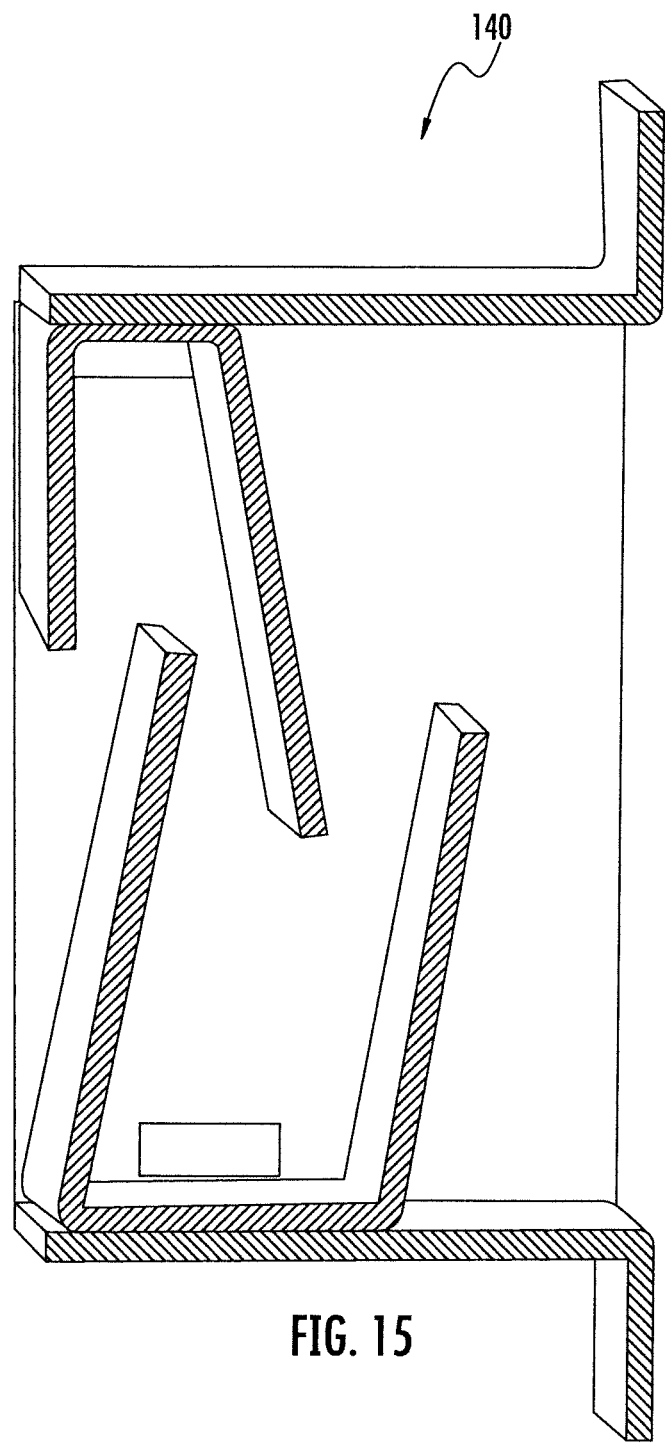
FIG. 15 is a section view of a light louver from the UV sterilization device of FIGS. 6-7.
Figure 16:
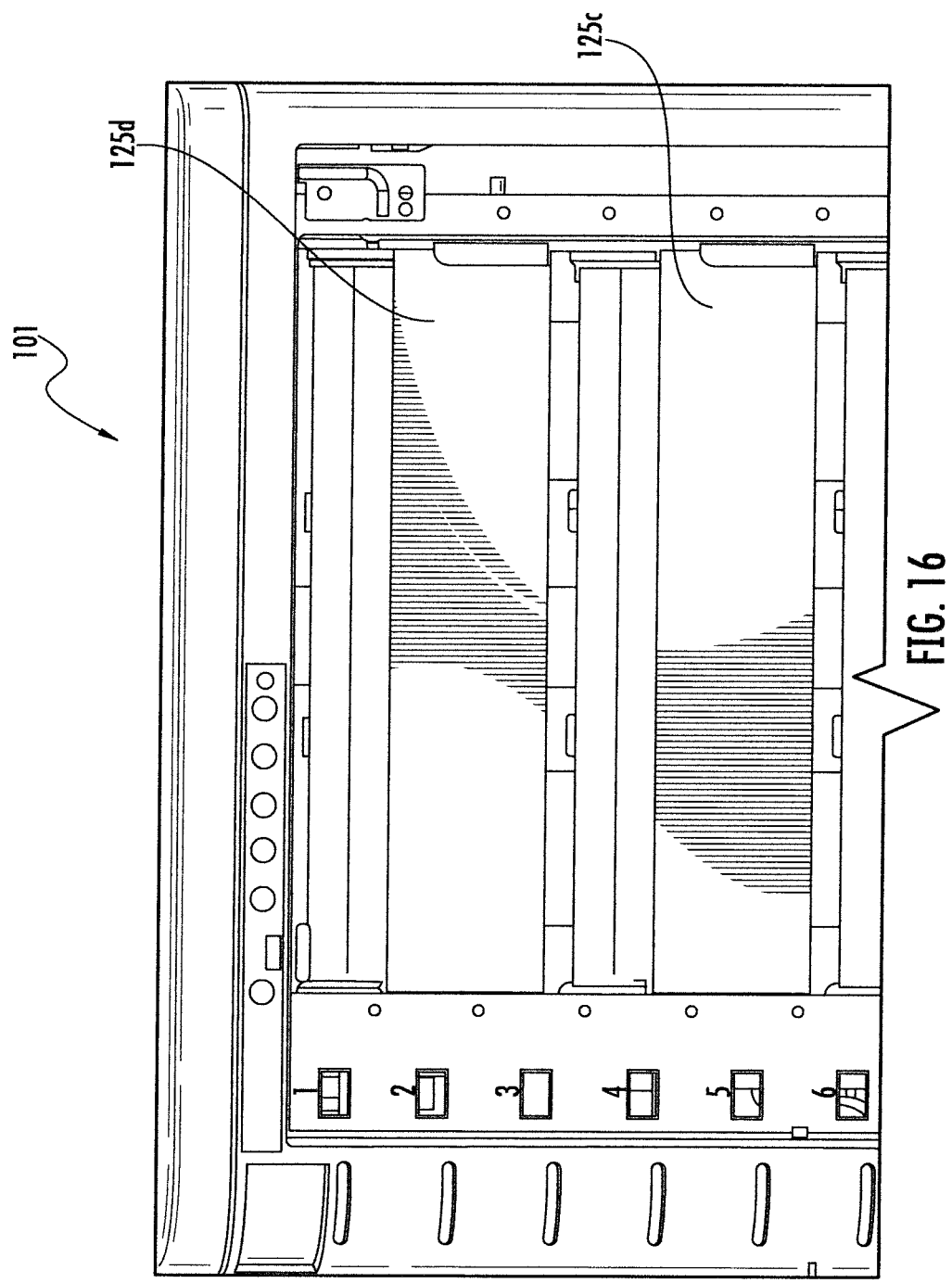
FIG. 16 is a partial front elevational view of the UV sterilization device of FIGS. 6-7.
Figure 17:
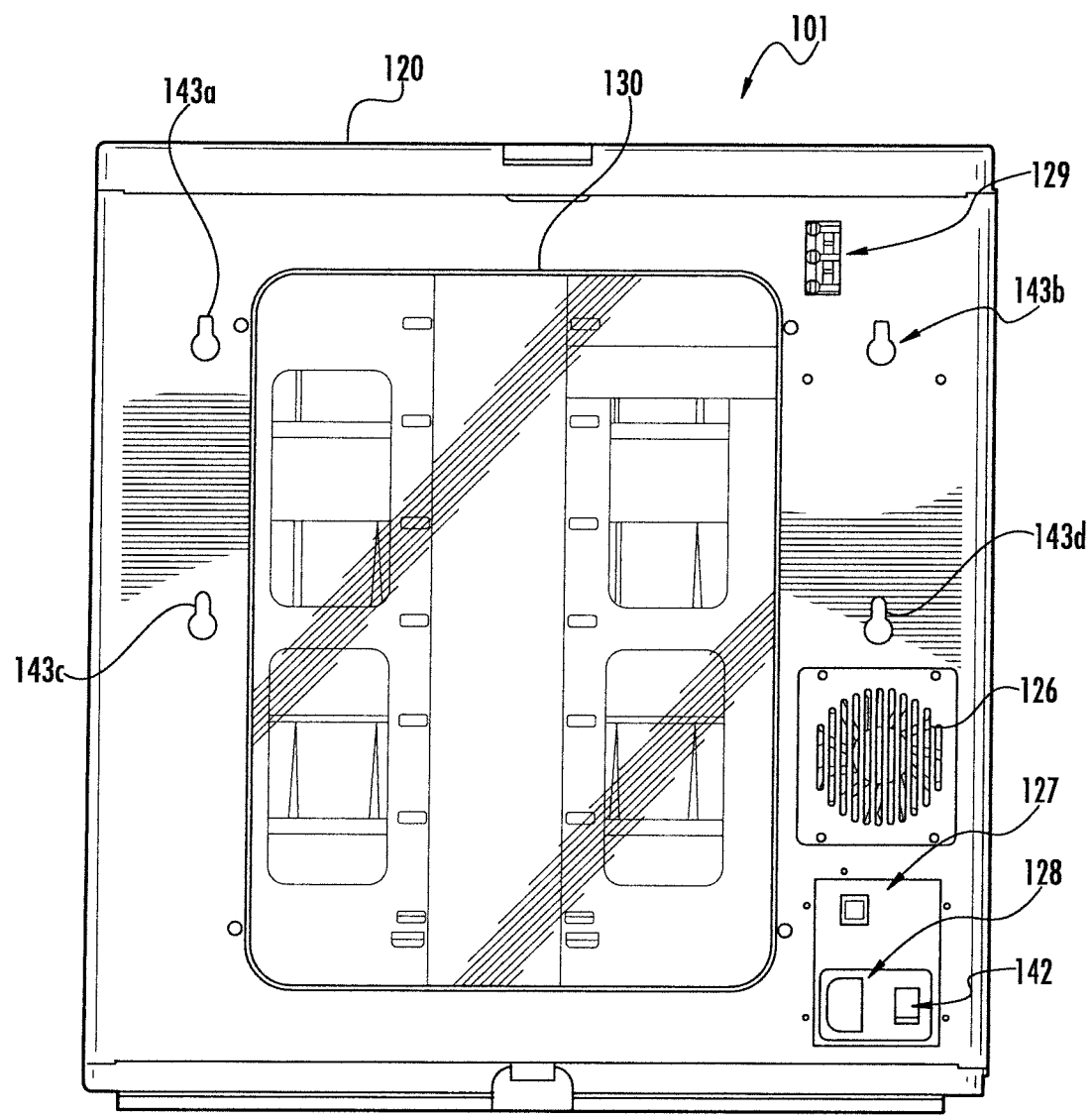
FIG. 17 is a back plant elevational view of the UV sterilization device of FIGS. 6-7.
Figure 18:
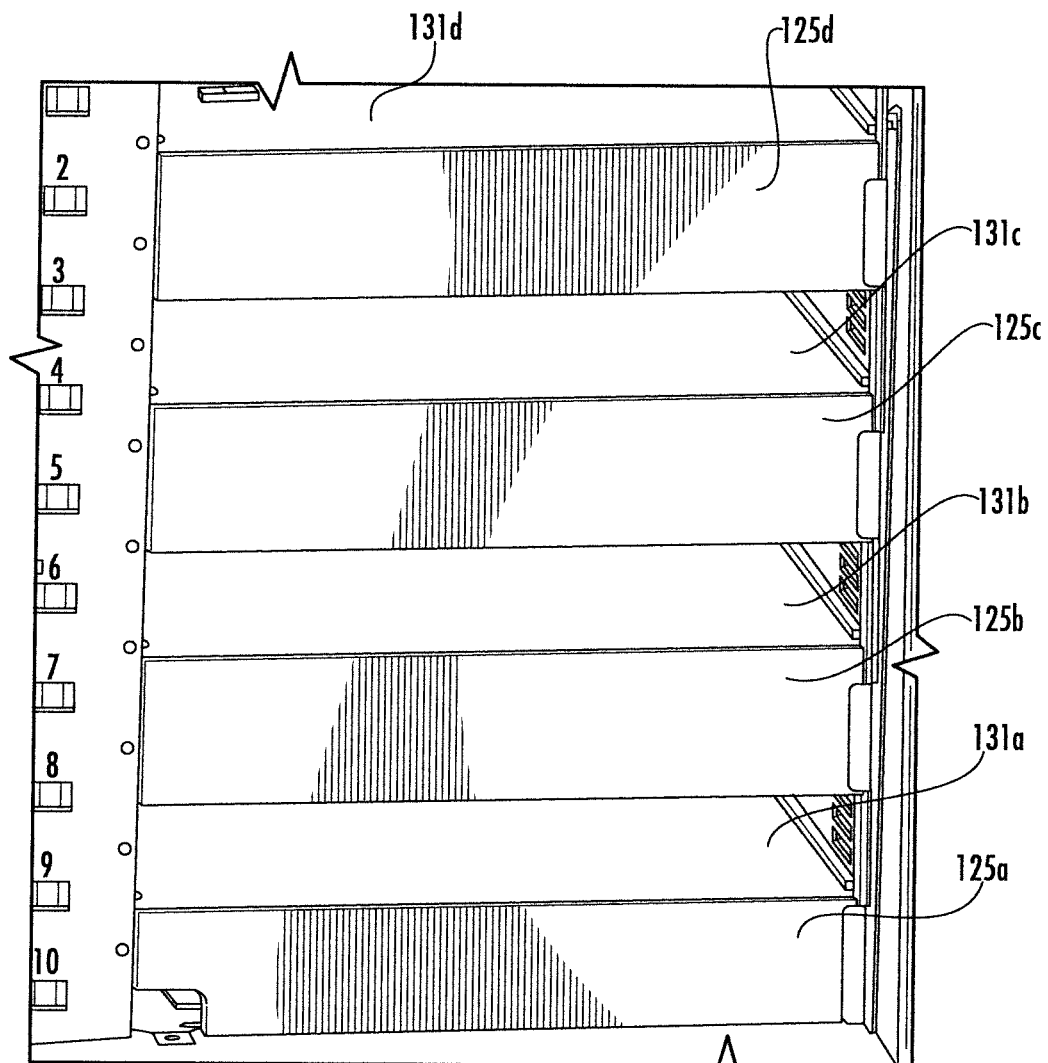
FIGS. 18-19 are partial front perspective views of the UV sterilization device of FIGS. 6-7.
Figure 19:
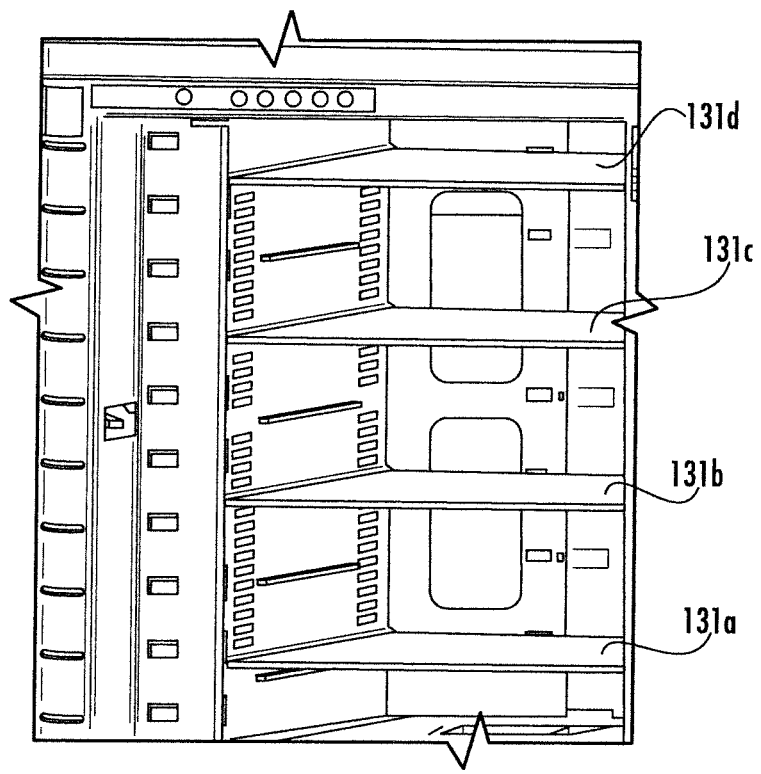
Figures 20A, 20B:
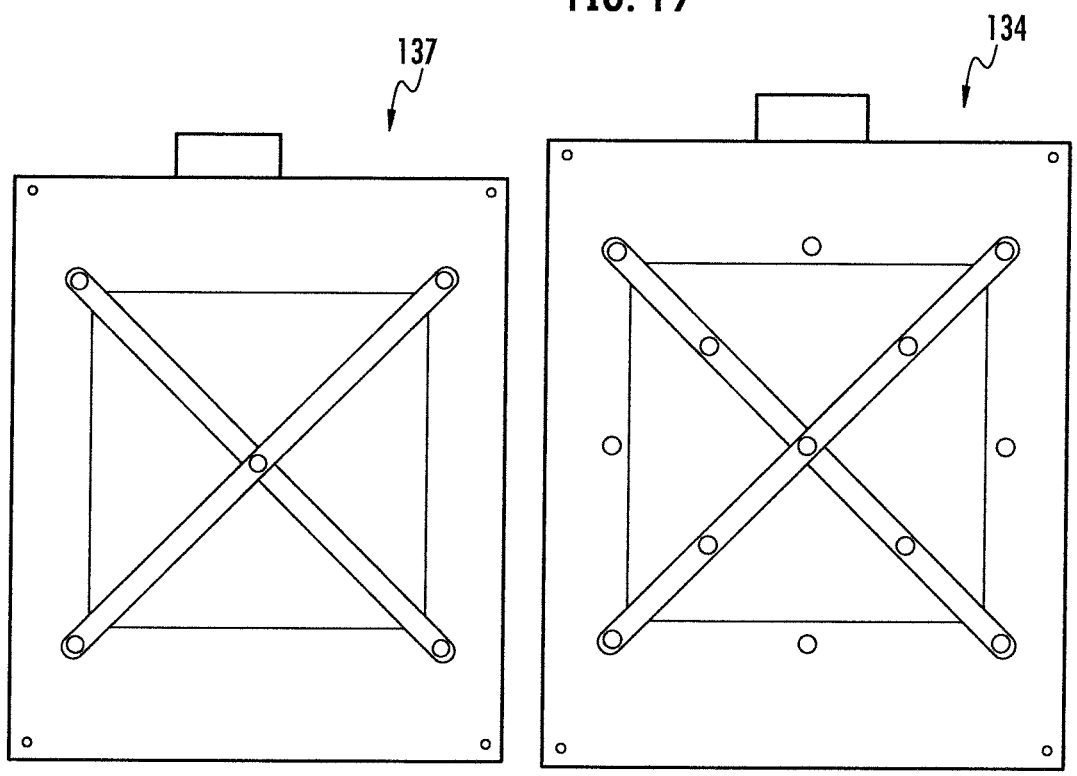
FIGS. 20A-20B are top plan elevational views of UB circuit boards from the UV sterilization device of FIGS. 6-7.
Figure 21:
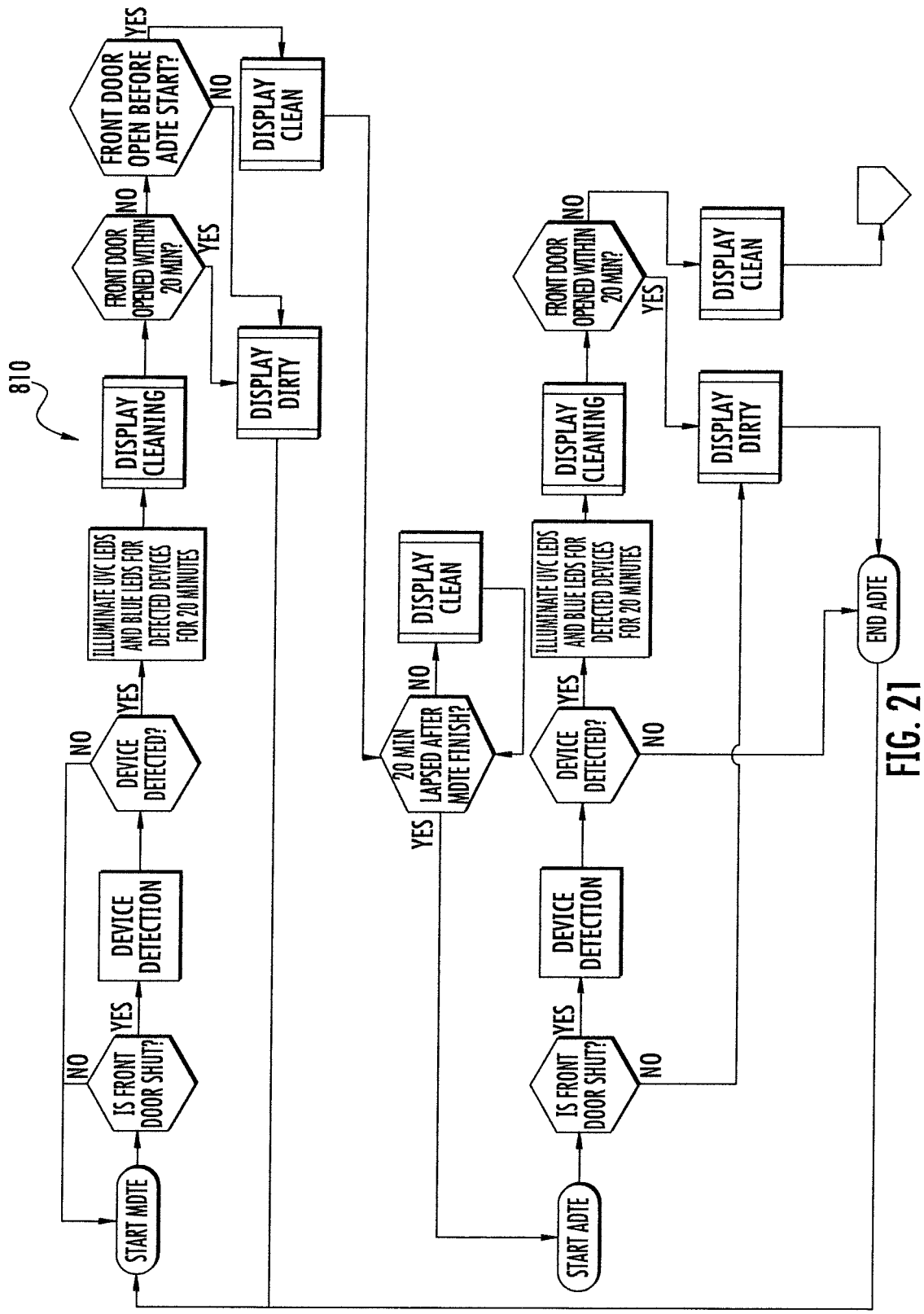
FIGS. 21-22 are a flowchart for operation of the UV sterilization device of FIGS. 6-7.
Figure 22:
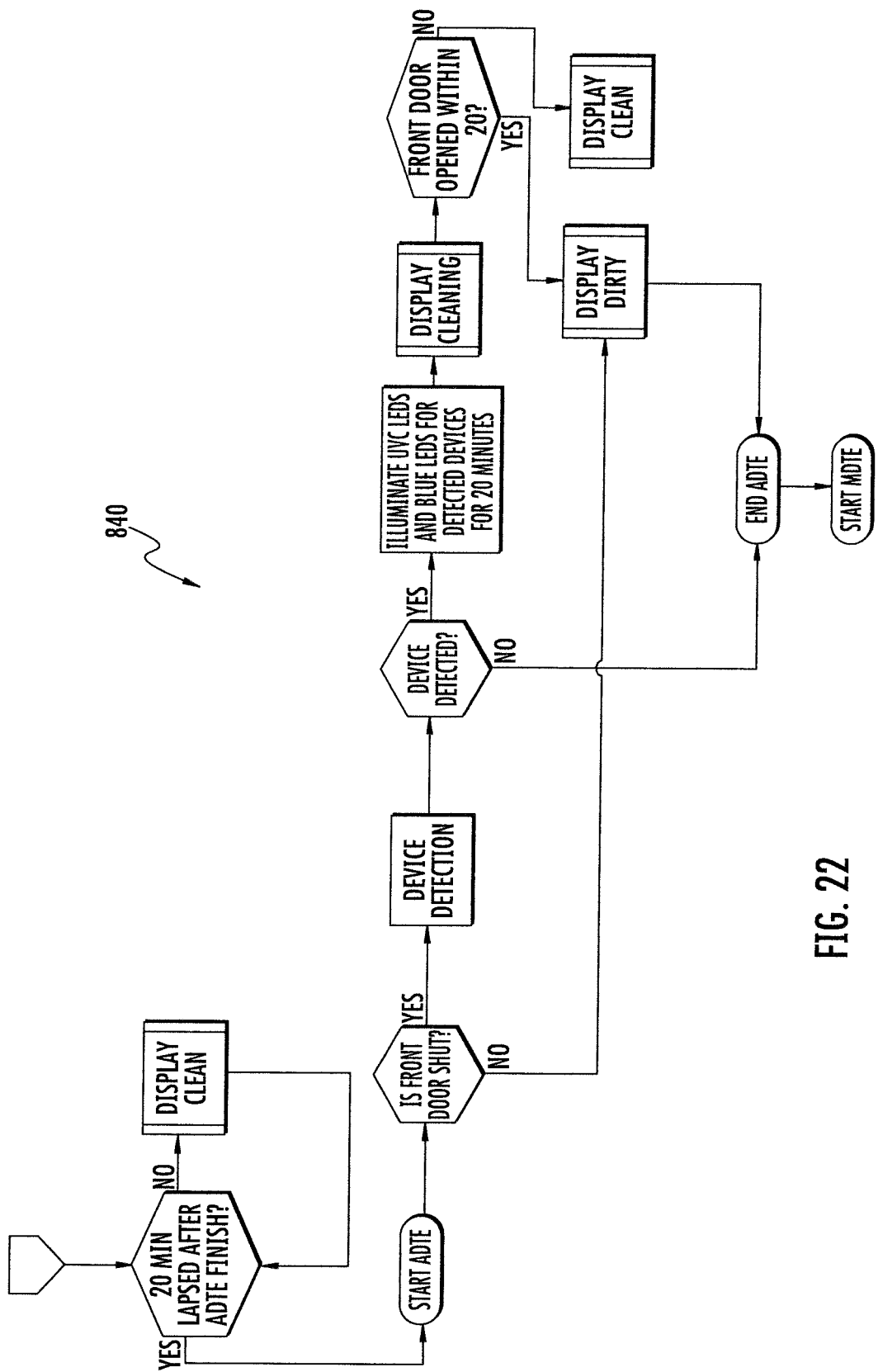
Figure 23:
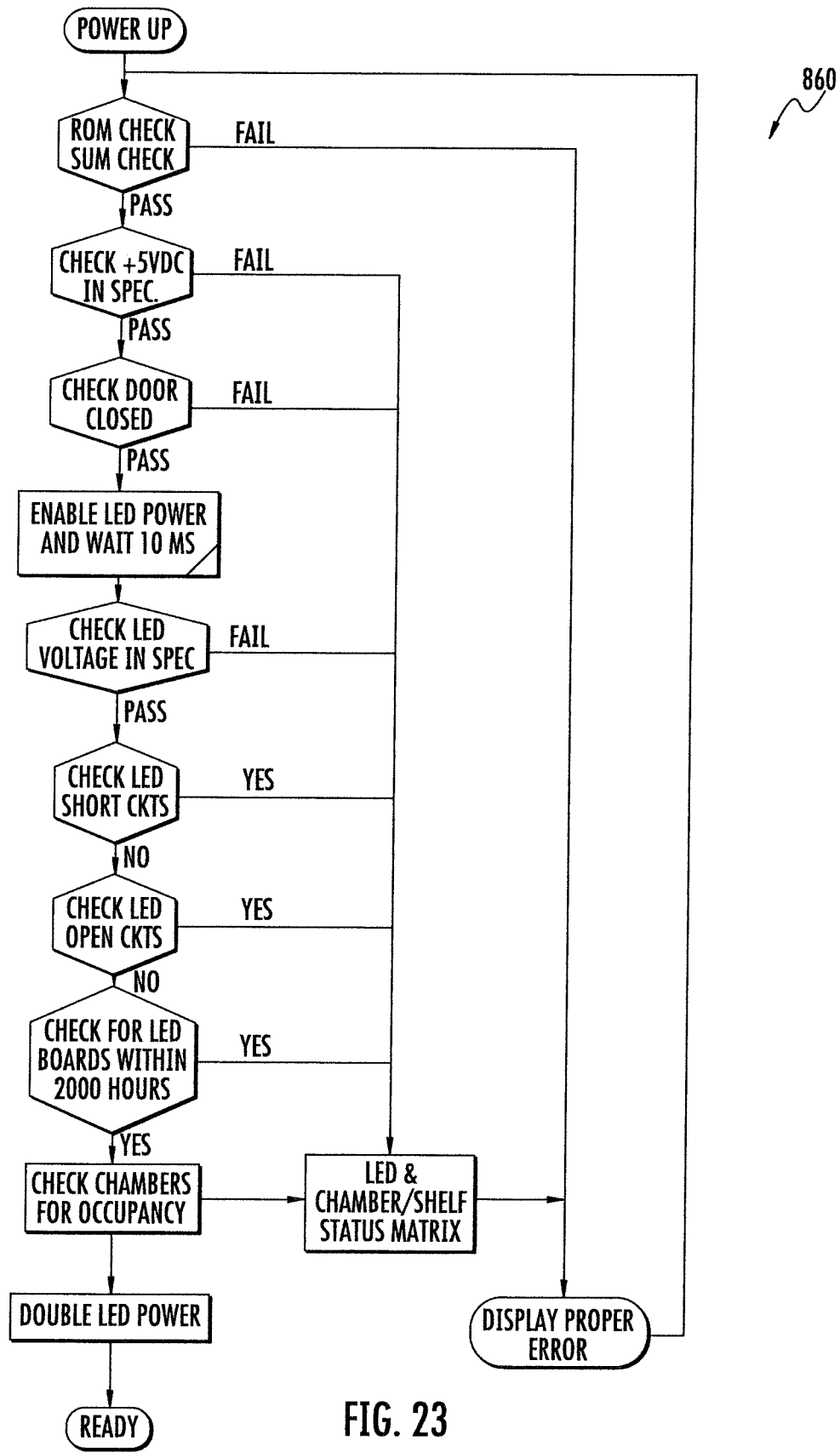
FIGS. 23-24 are flowcharts for operation of the UV sterilization device of FIGS. 6-7.
Figure 24:
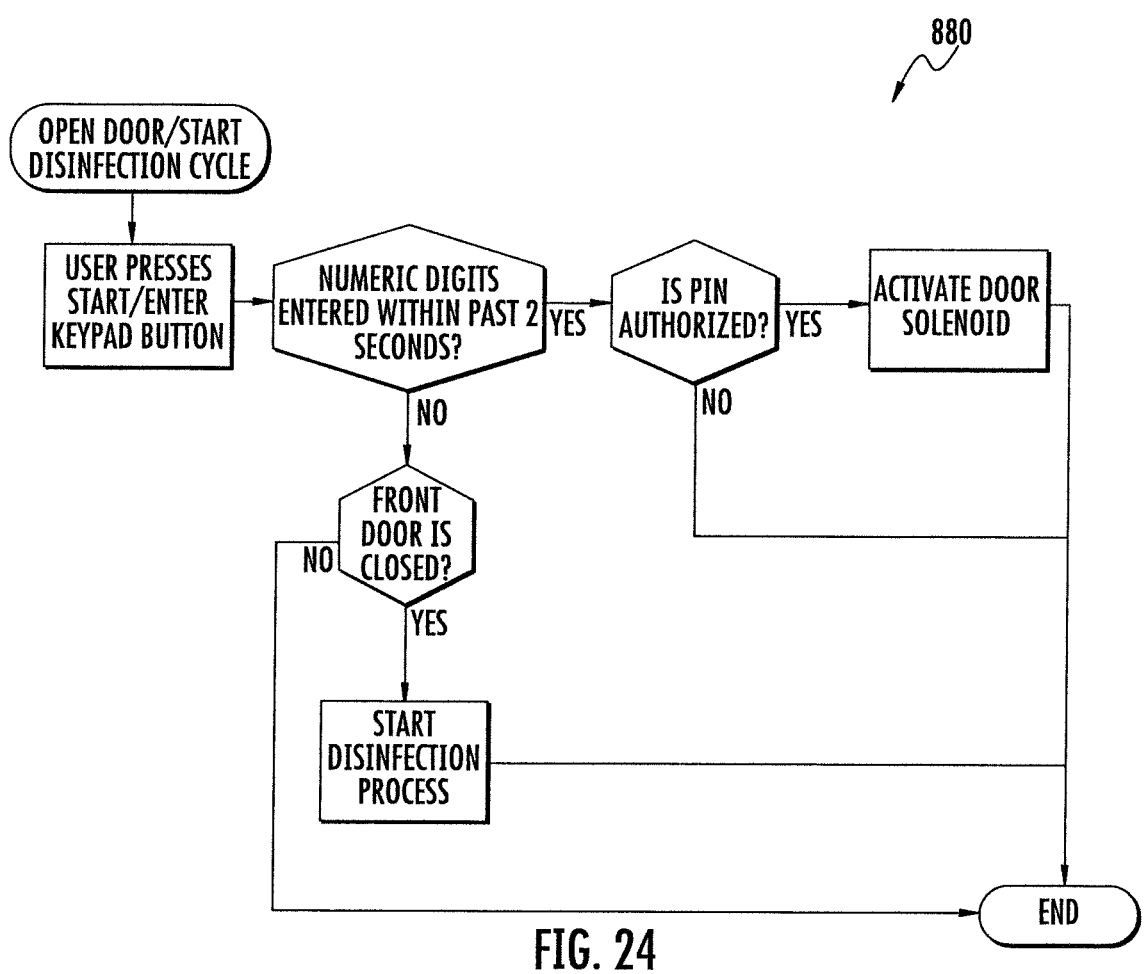

Referring now additionally to FIG. 3, another embodiment of the UV sterilization system 100 is now described. In this embodiment of the UV sterilization system 300, those elements already discussed above with respect to FIG. 1 are incremented by 200 and most require no further discussion herein. This embodiment differs from the previous embodiment in that this UV sterilization system 300 illustratively includes the server 311 as a virtual private cloud implementation. The server 311 illustratively includes a plurality of modules 315-318.

Referring now to FIGS. 4-5, 21-24, diagrams 800, 805 illustrate structure of example embodiments of the UV sterilization system 100. Flowcharts 810, 840, 860, 880 show the logic of the controller 144 of the operation of the UV sterilization device 101a-101d.

Figure 25:
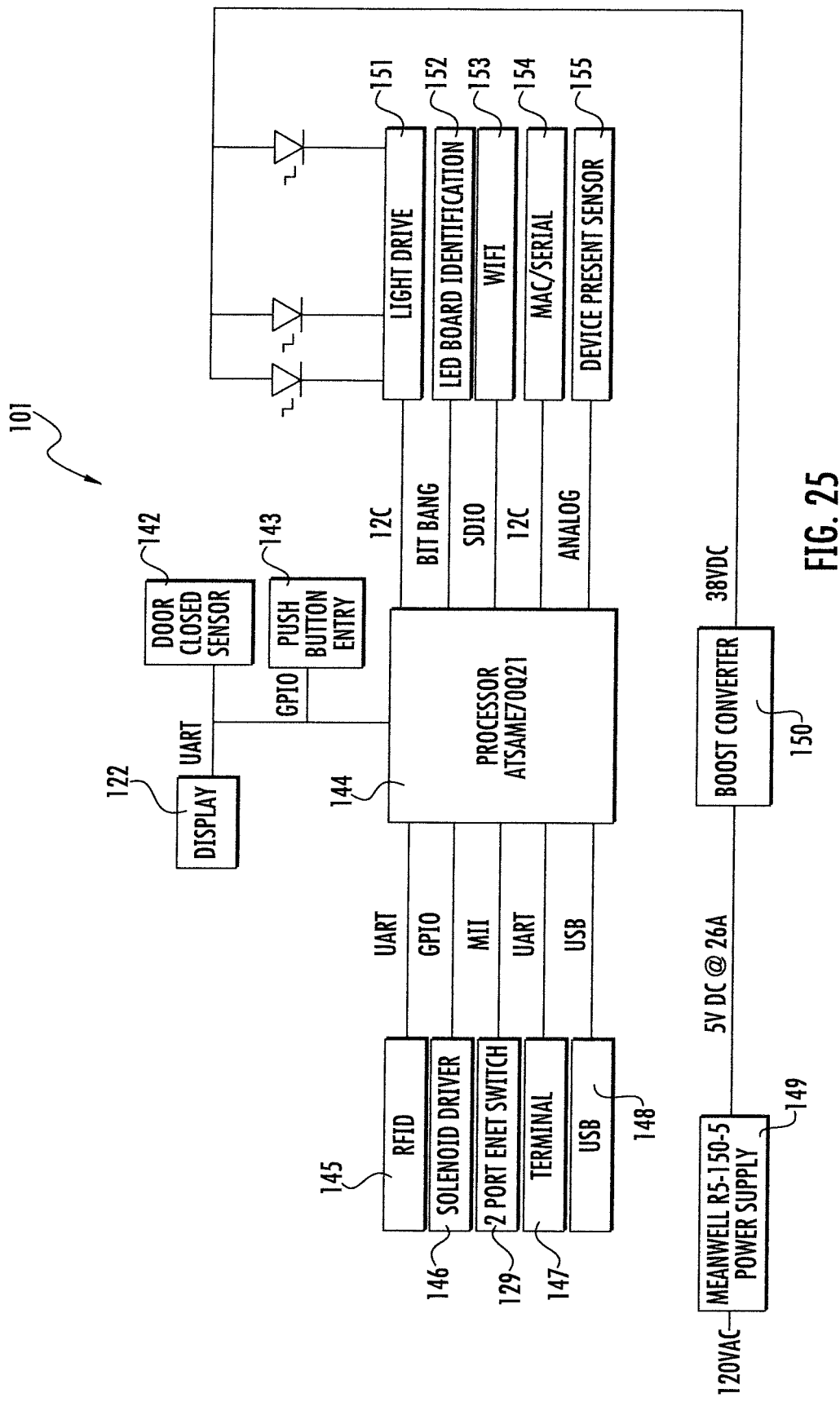
FIG. 25 is a schematic diagram of a UV sterilization device, according to the present disclosure.

Referring now to FIG. 25, the UV sterilization device 101 illustratively includes the RF transmitter 115 coupled to the controller 144, the solenoid driver circuit 146 coupled to the controller, the wired port 129 coupled to the controller, a terminal port 147 also coupled to the controller, a display 122 coupled to the controller, a door sensor 142 coupled to the controller, and a push button entry 143 coupled to the controller. The UV sterilization device 101 illustratively includes a light driver circuit 151 coupled to the controller 144, a LED board identification circuit 152 coupled to the controller, a wireless transceiver 153 coupled to the controller, a MAC/serial circuit 154 coupled to the controller, and a device present sensor (e.g. image sensor) coupled to the controller. The UV sterilization device 101 illustratively includes a power supply 149, and a boost converter circuit 150 coupled between the power supply and the light driver circuit 151.

Figure 26:
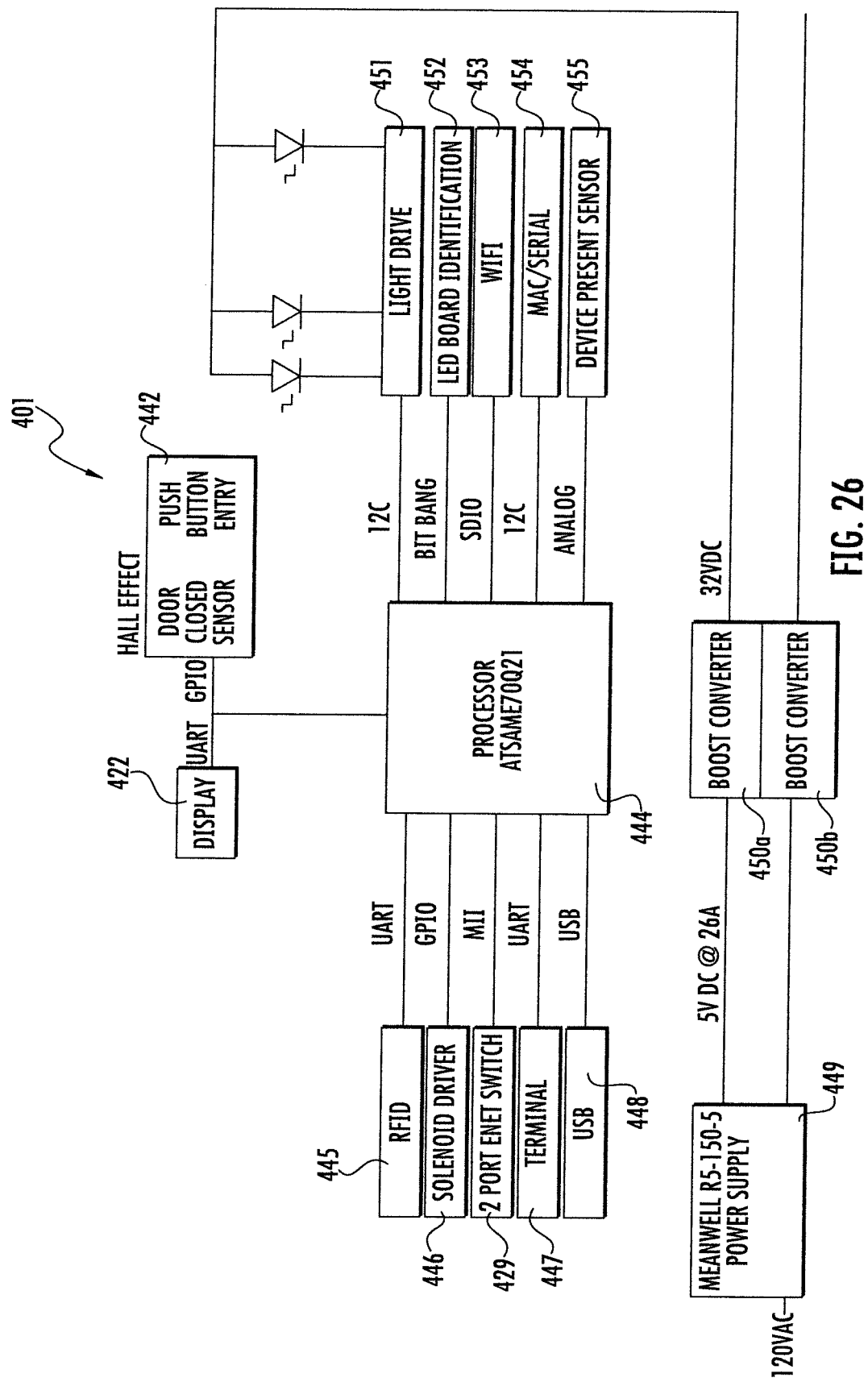
FIG. 26 is a schematic diagram of a UV sterilization device, according to the present disclosure.

Referring now additionally to FIG. 26, another embodiment of the UV sterilization device 101 is now described. In this embodiment of the UV sterilization device 401, those elements already discussed above with respect to FIG. 25 are incremented by 300 and most require no further discussion herein. This embodiment differs from the previous embodiment in that this UV sterilization device 401 illustratively includes first and second boost converters 450*a*-450*b*.

Figure 30A:
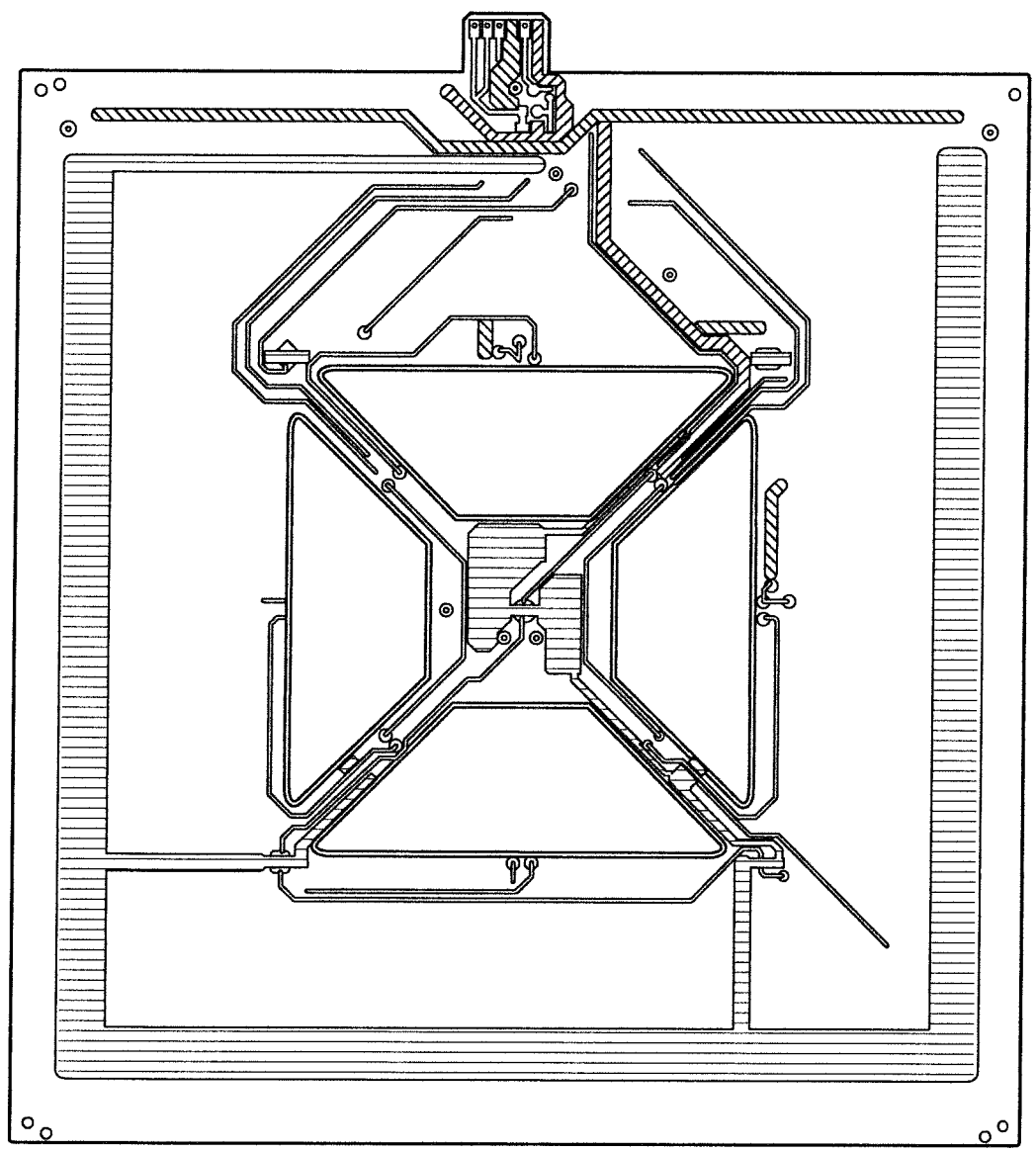
FIGS. 30A-30B are images of circuit board layers for the UV CBAs in the UV sterilization device of FIGS. 6-7.
Figure 30B:
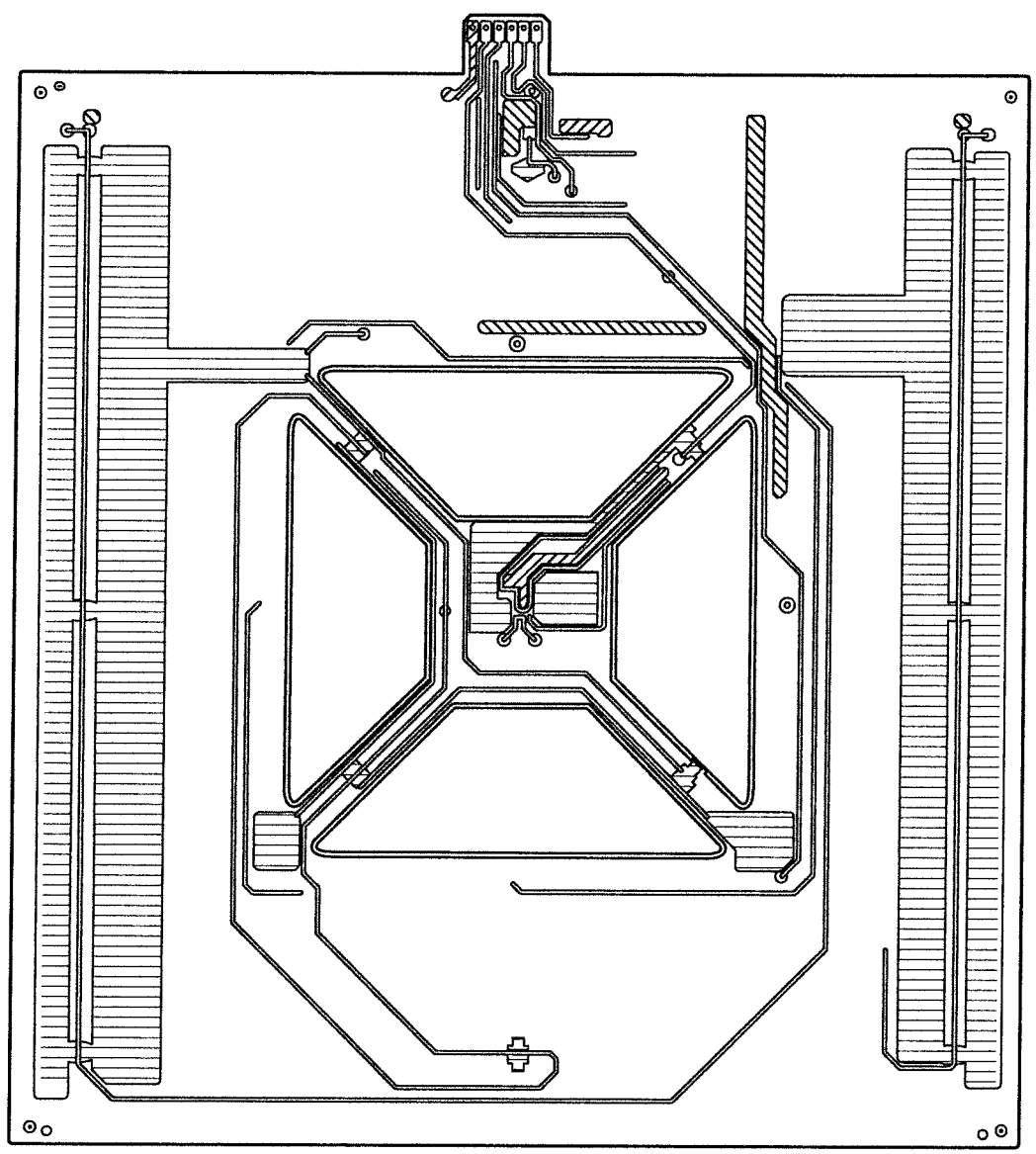
Figure 31:
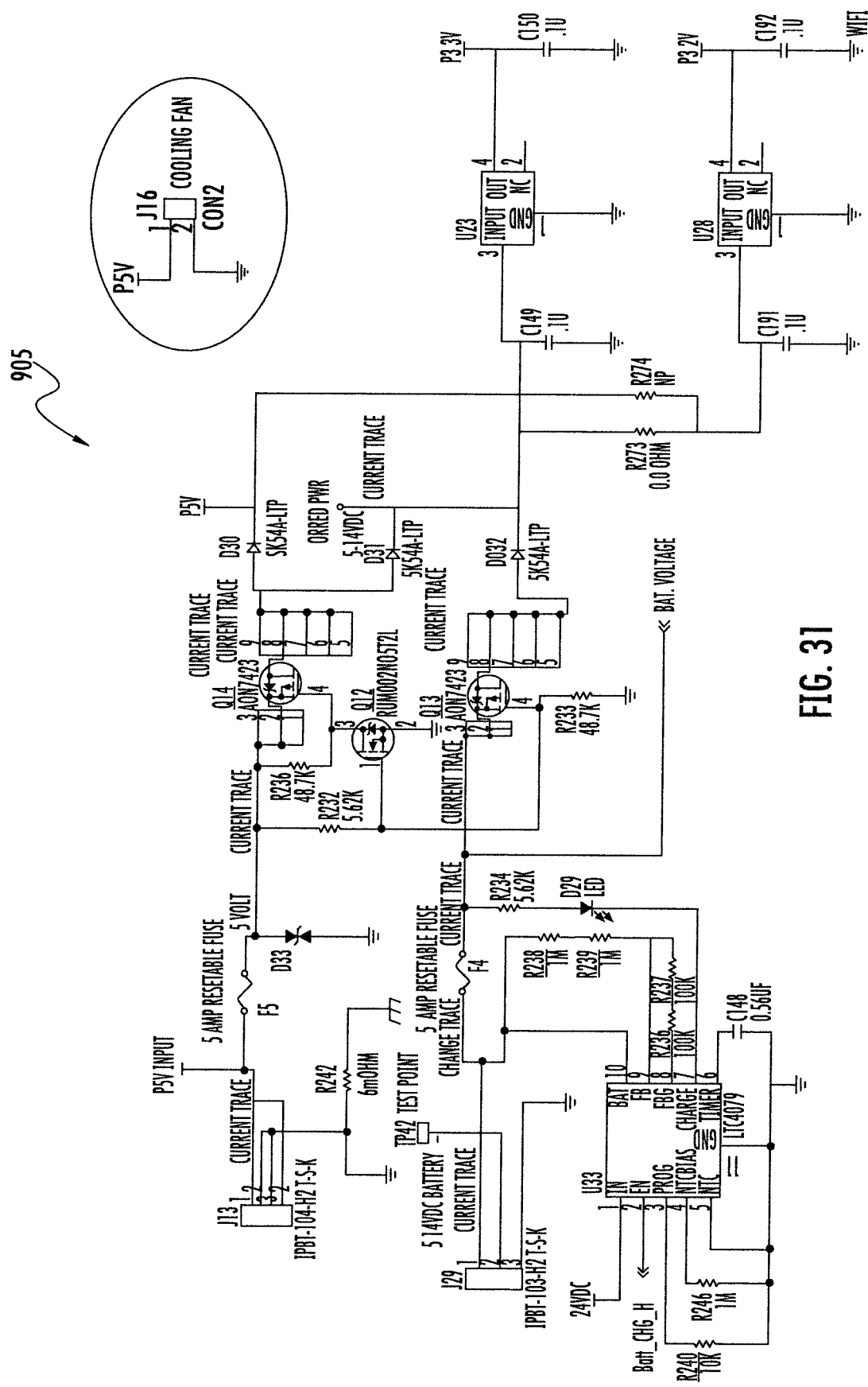
FIGS. 31-33F are circuit diagrams for the controller in an embodiment of the UV sterilization device, according to the present disclosure.
Figure 32A:
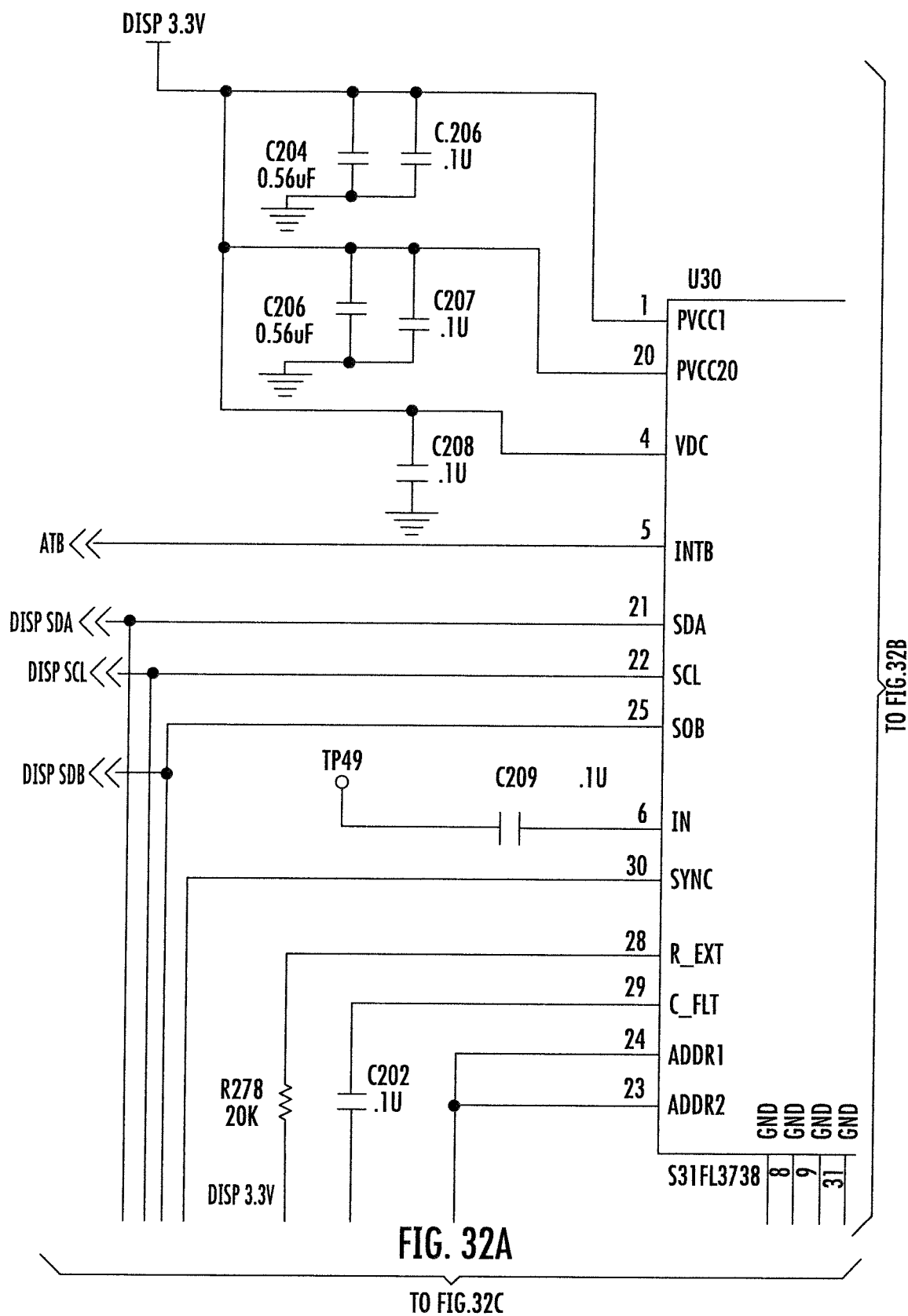
Figure 32B:
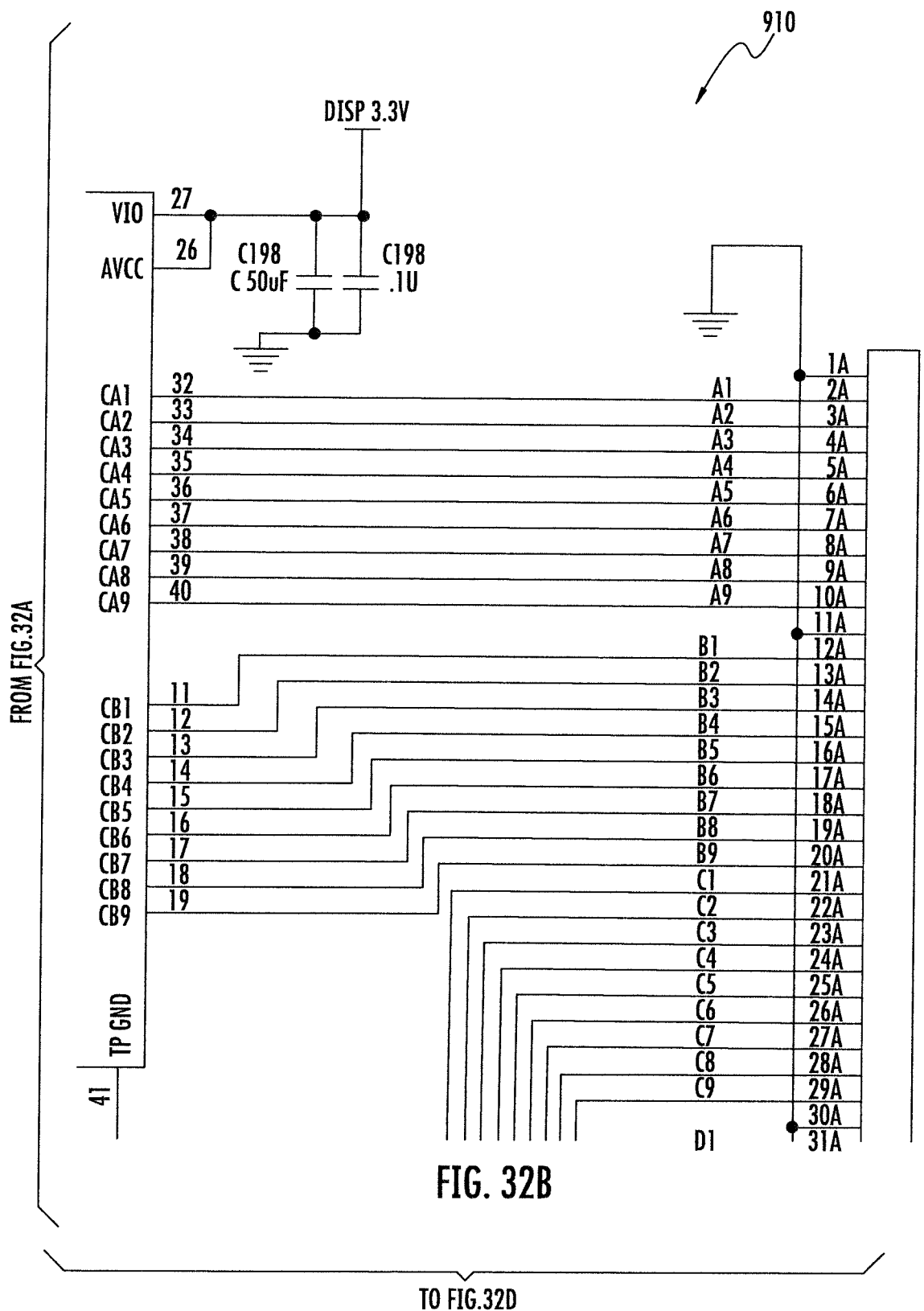
Figure 32C:
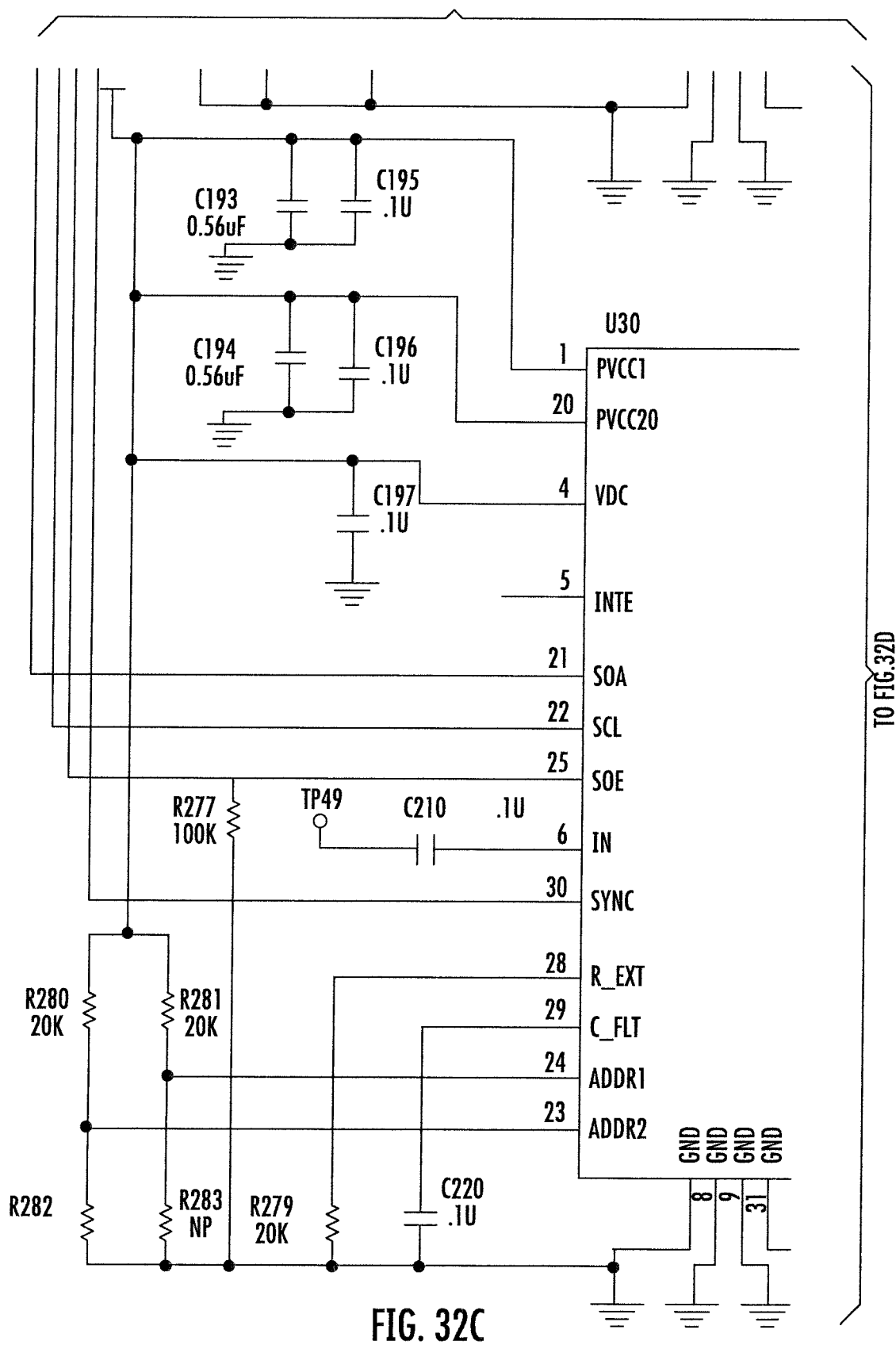
Figure 32D:
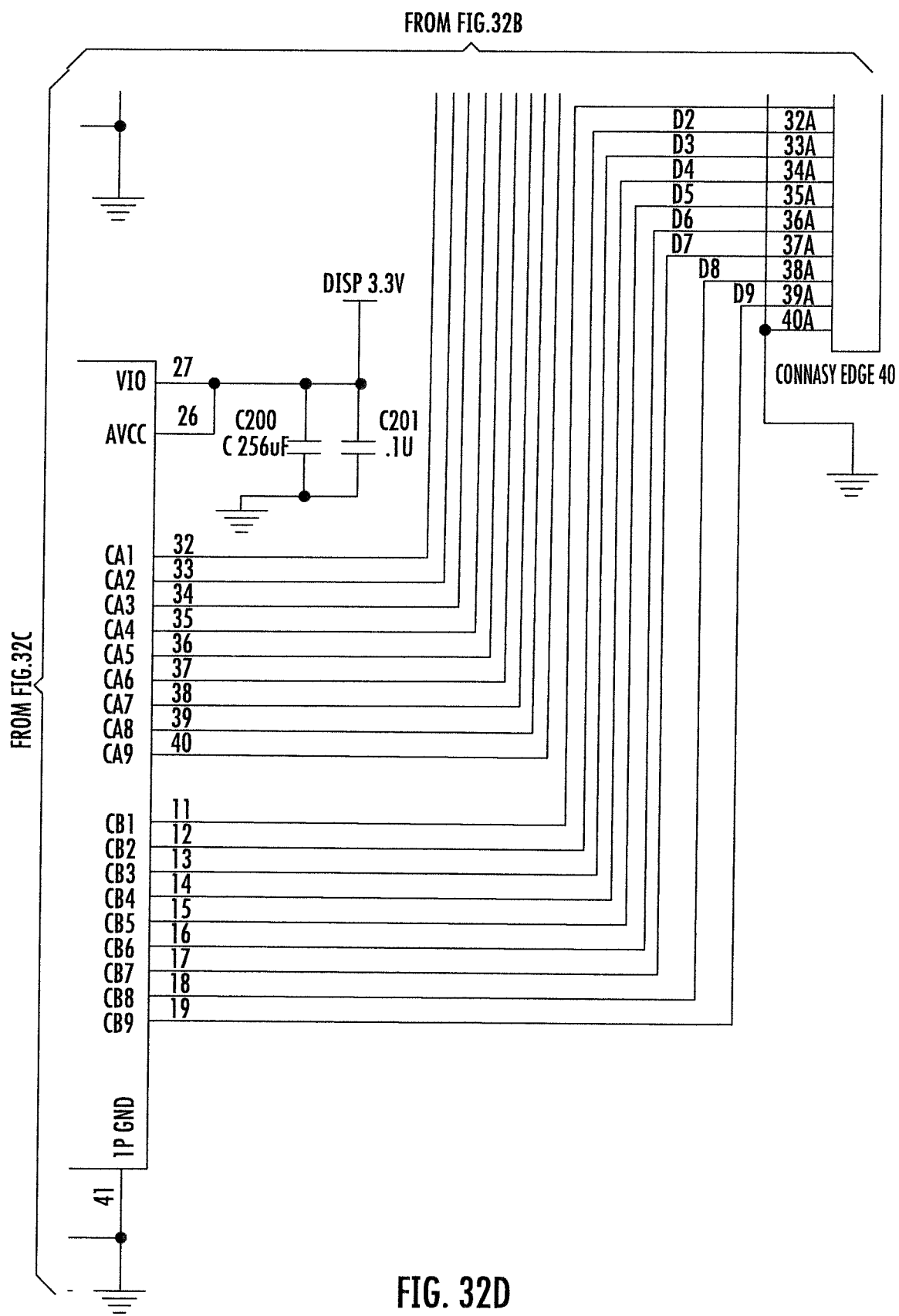
Figure 33A:
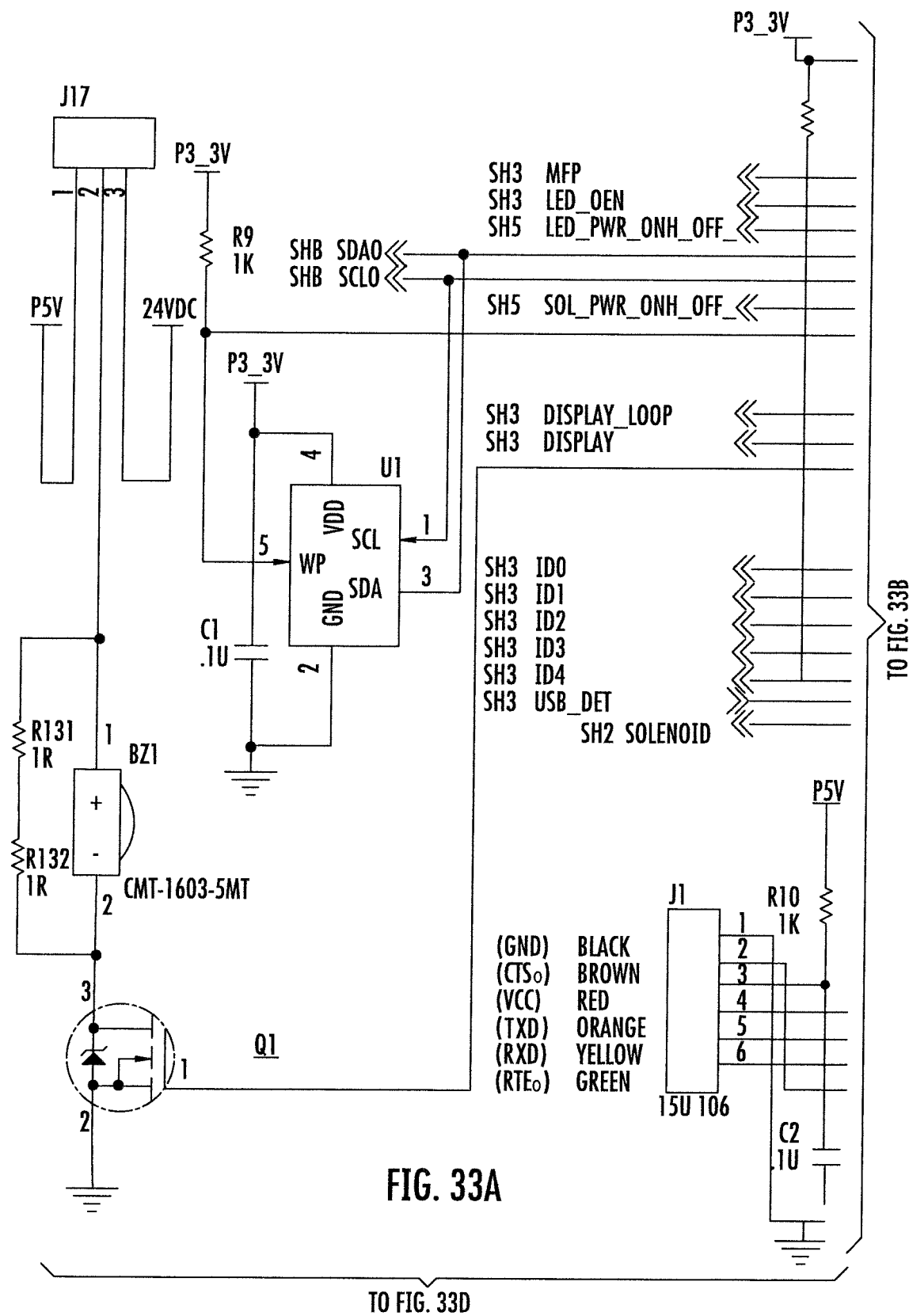
Figure 33B:
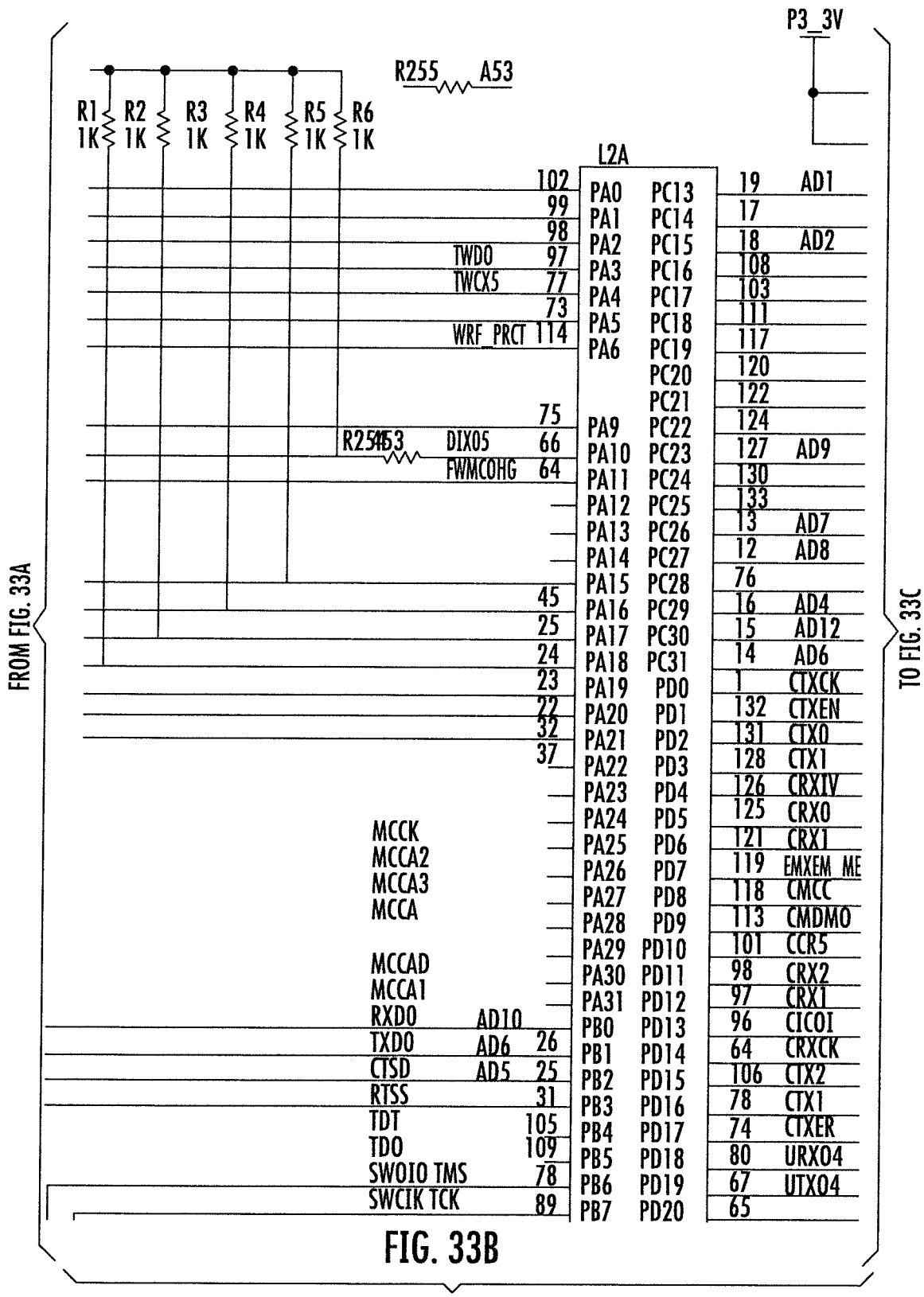
Figure 33C:
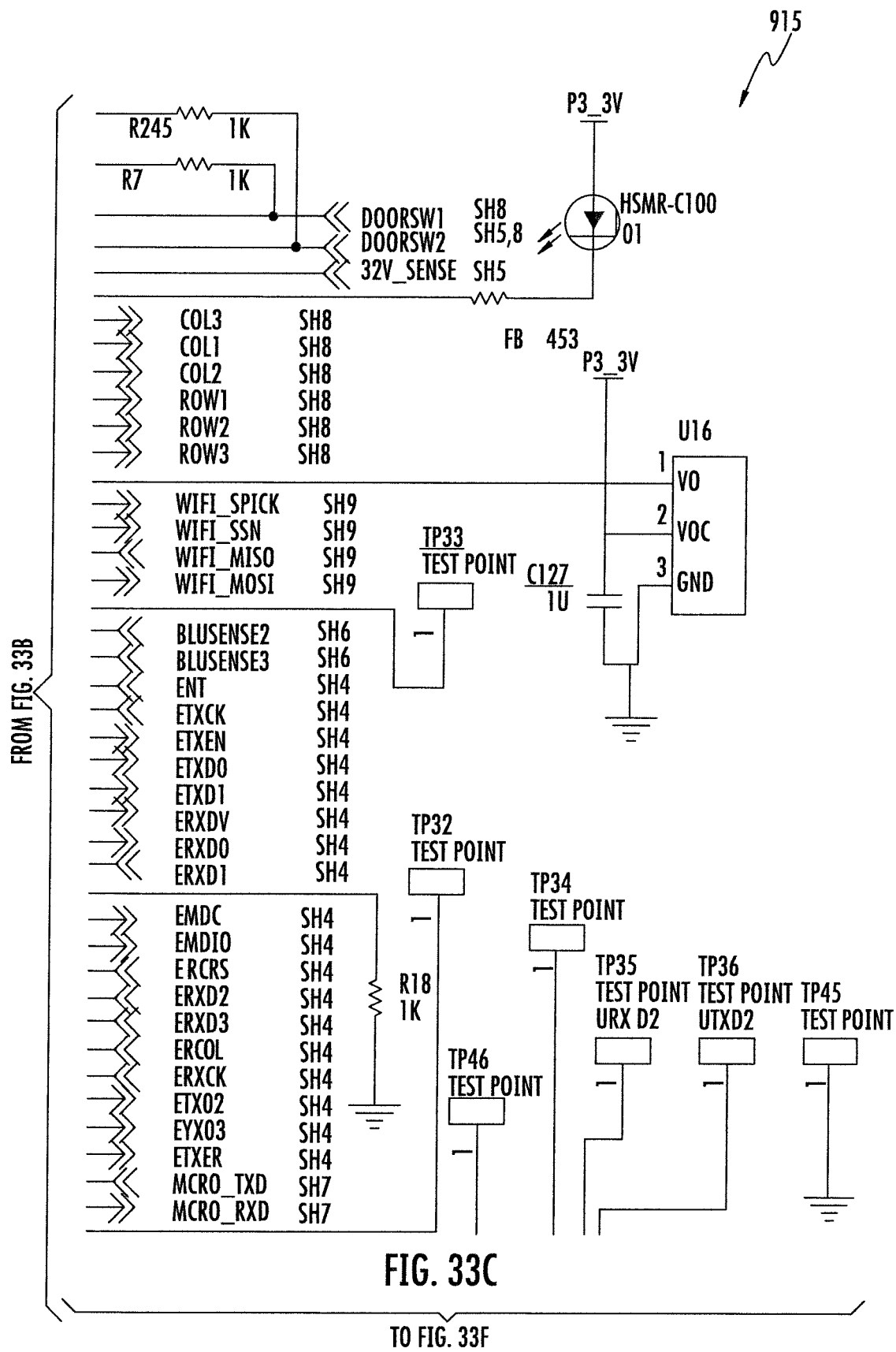
Figure 33D:
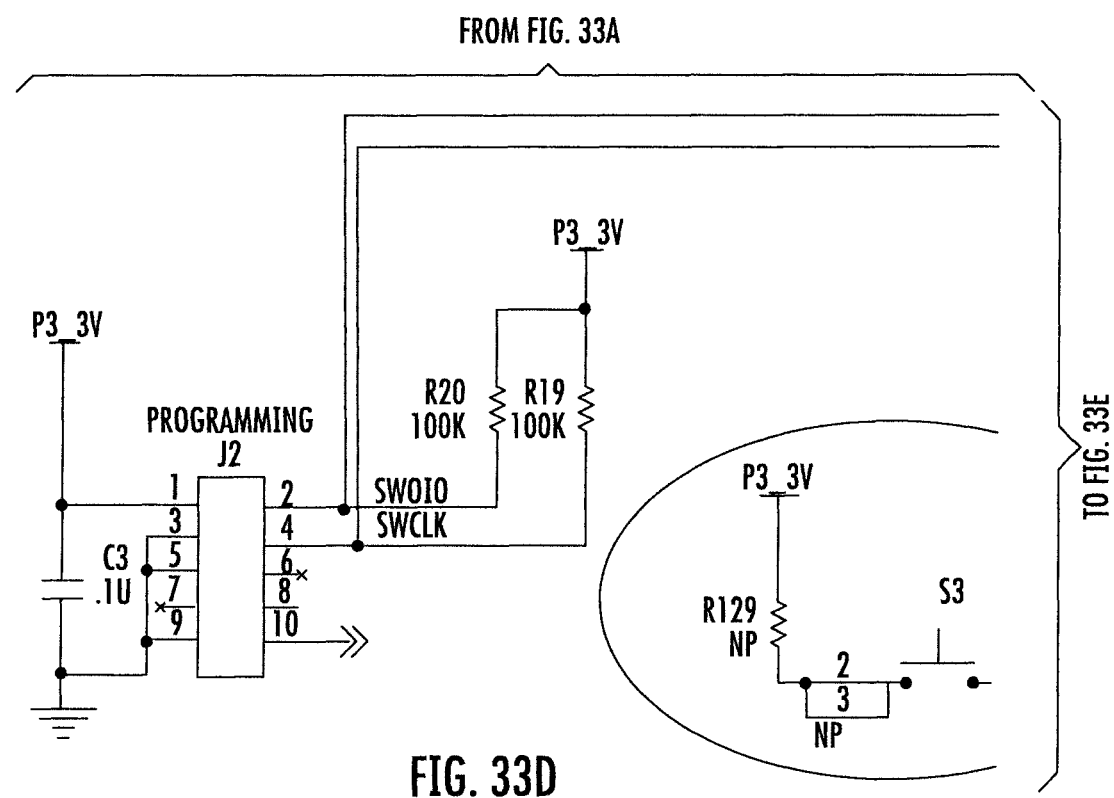
Figure 33E:
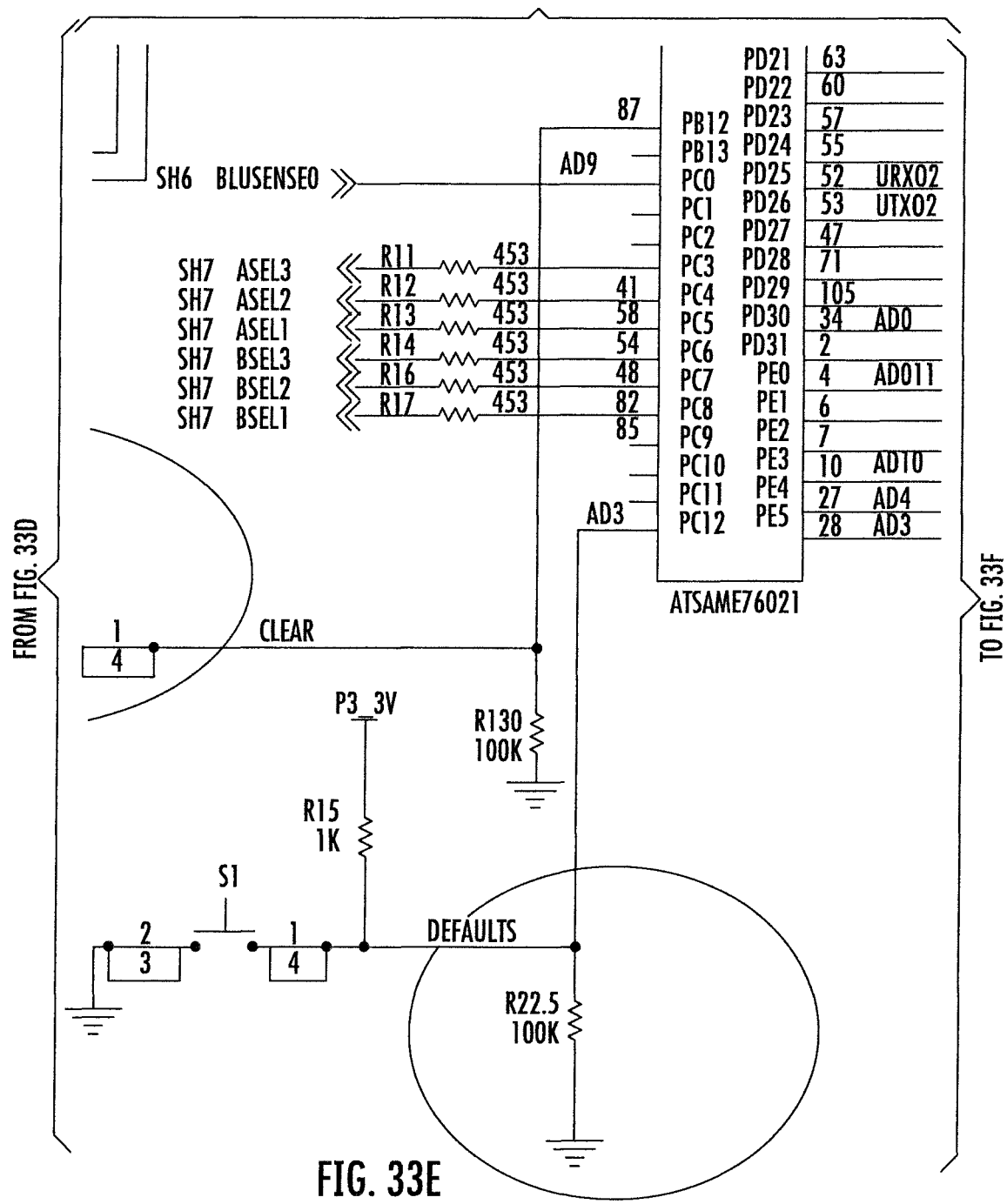
Figure 33F:
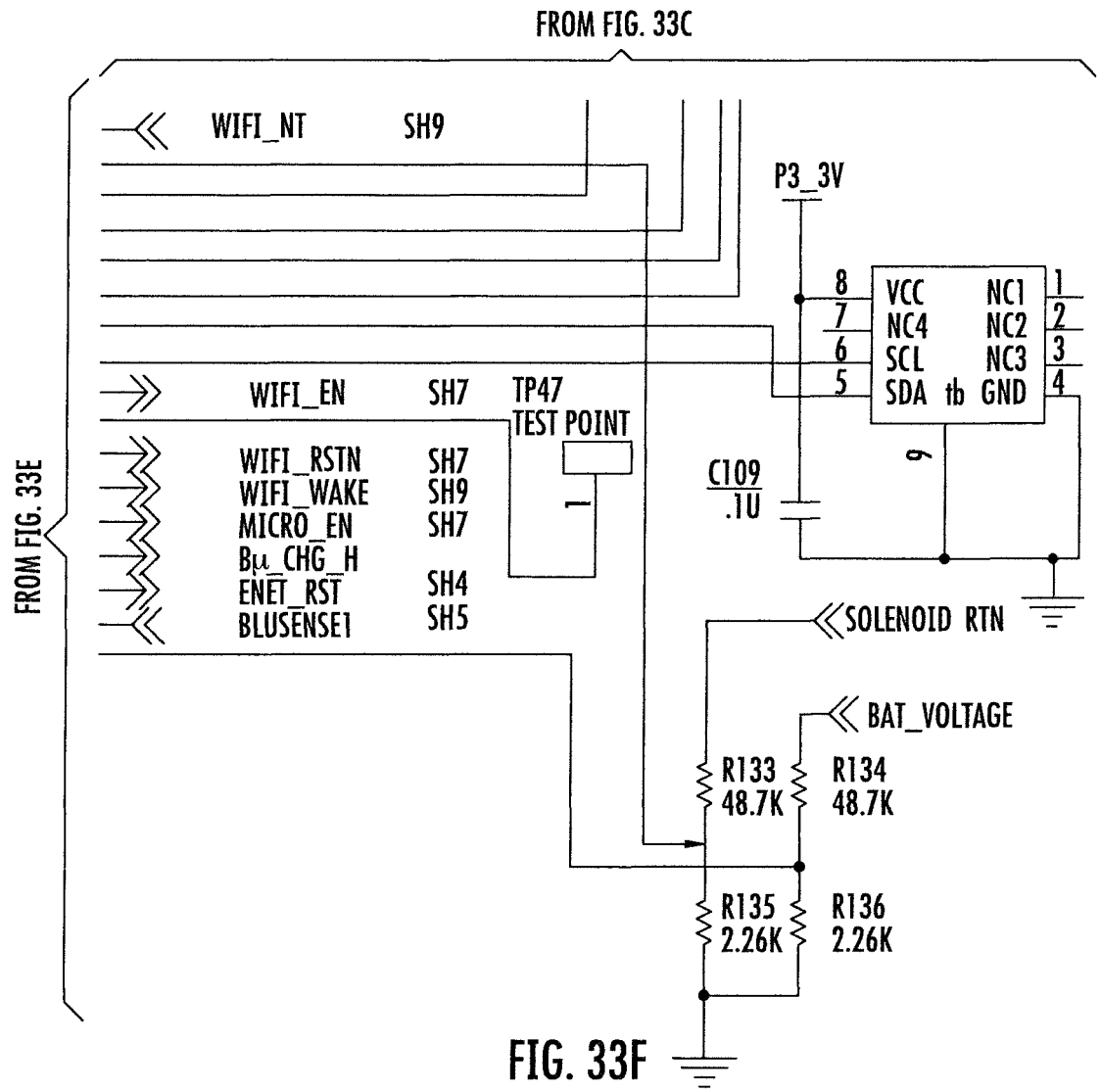
Figure 34A:
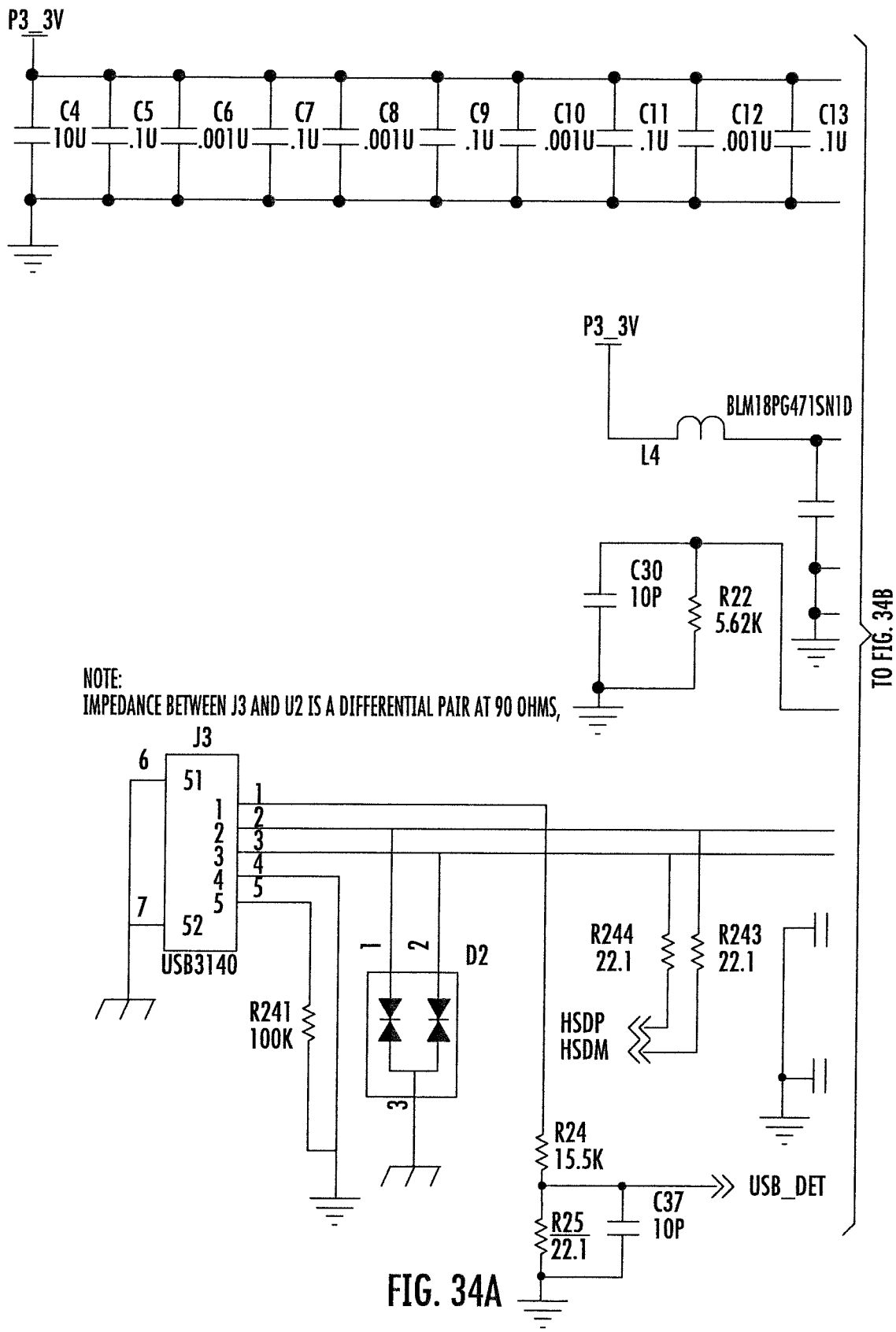
FIGS. 34A-34C are a circuit diagram for power for the controller in an embodiment of the UV sterilization device, according to the present disclosure.
Figure 34B:
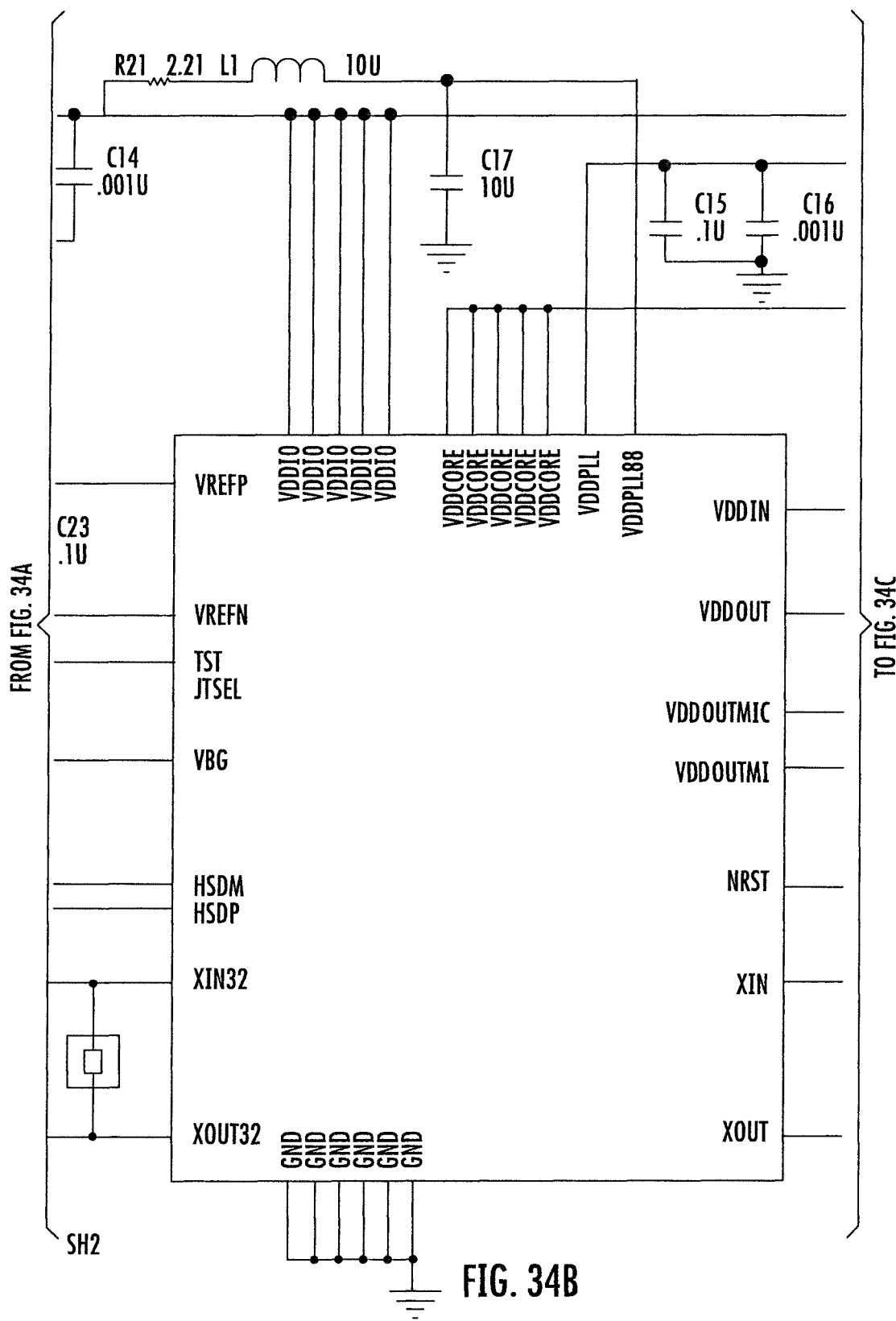
Figure 34C:
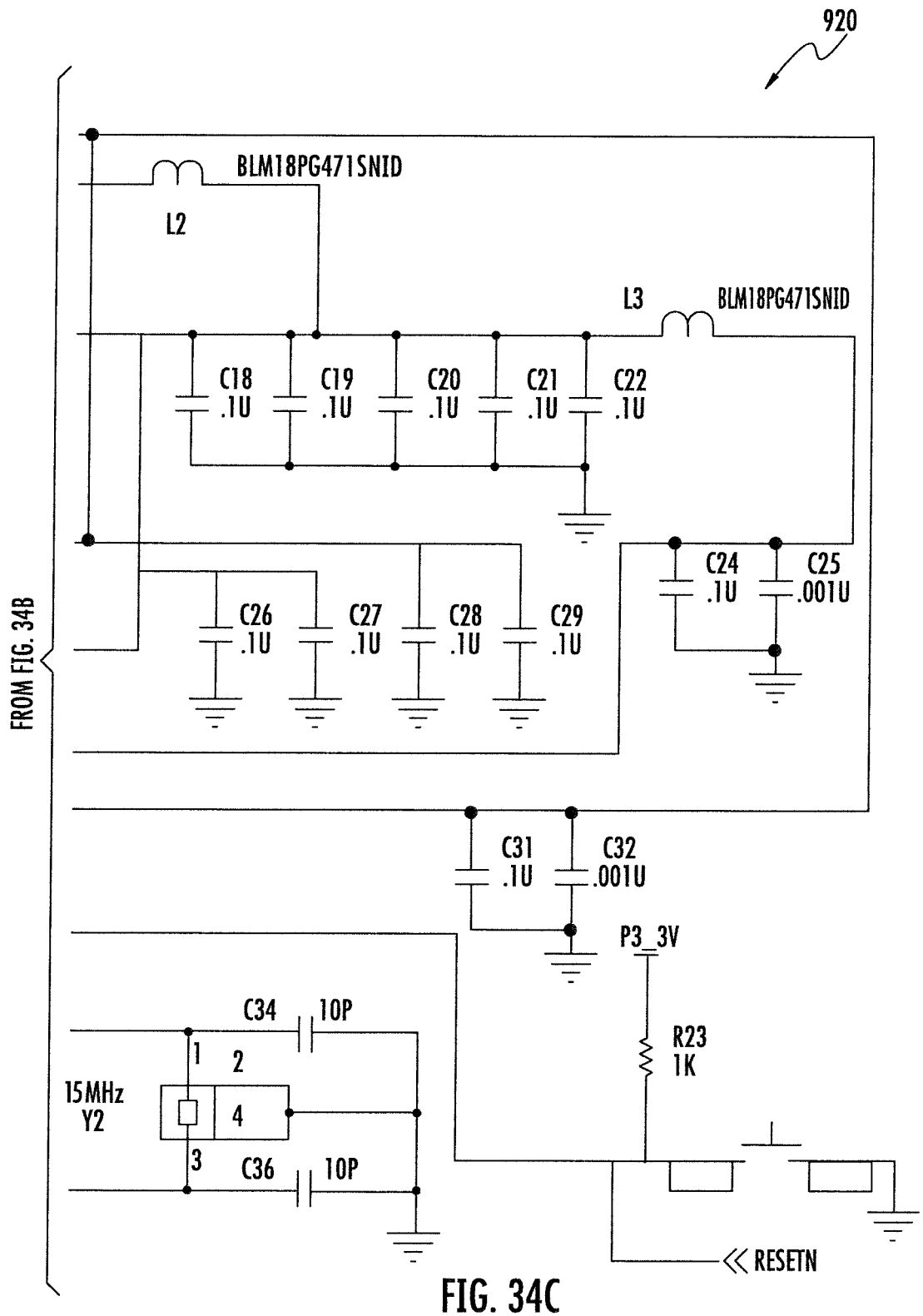
Figure 35A:
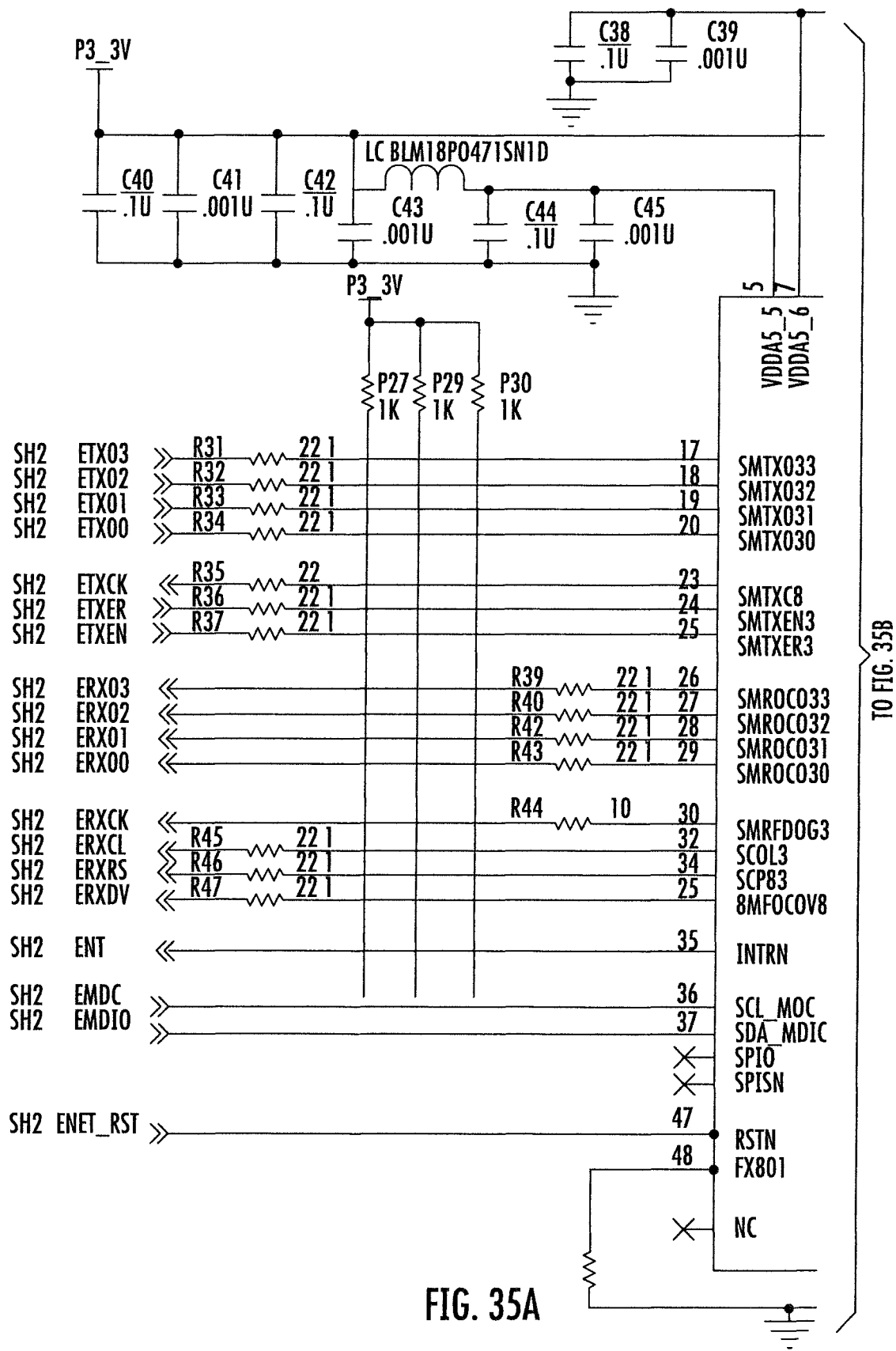
FIGS. 35A-35C are a circuit diagram for the Ethernet connection in an embodiment of the UV sterilization device, according to the present disclosure.
Figure 35B:
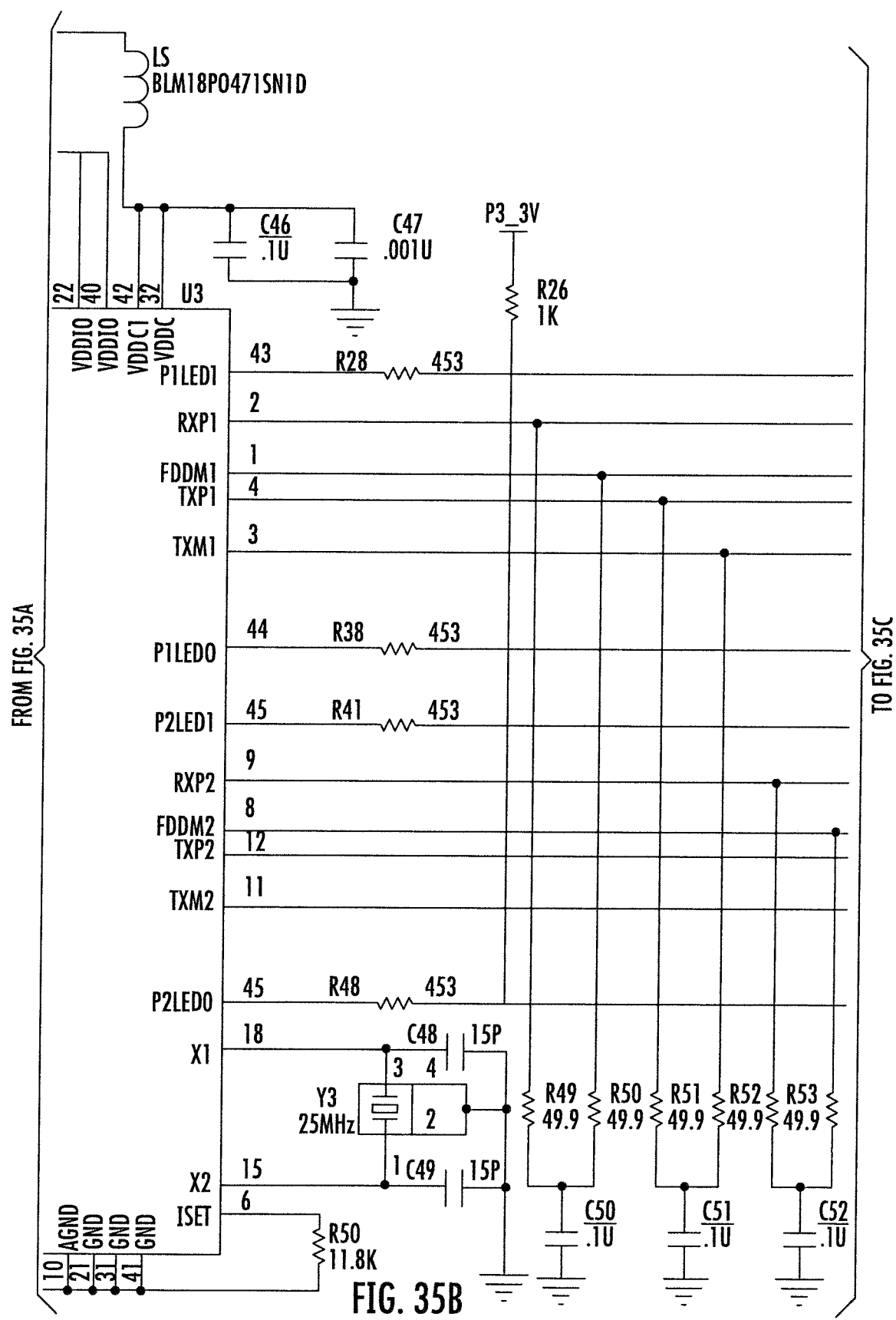
Figure 35C:
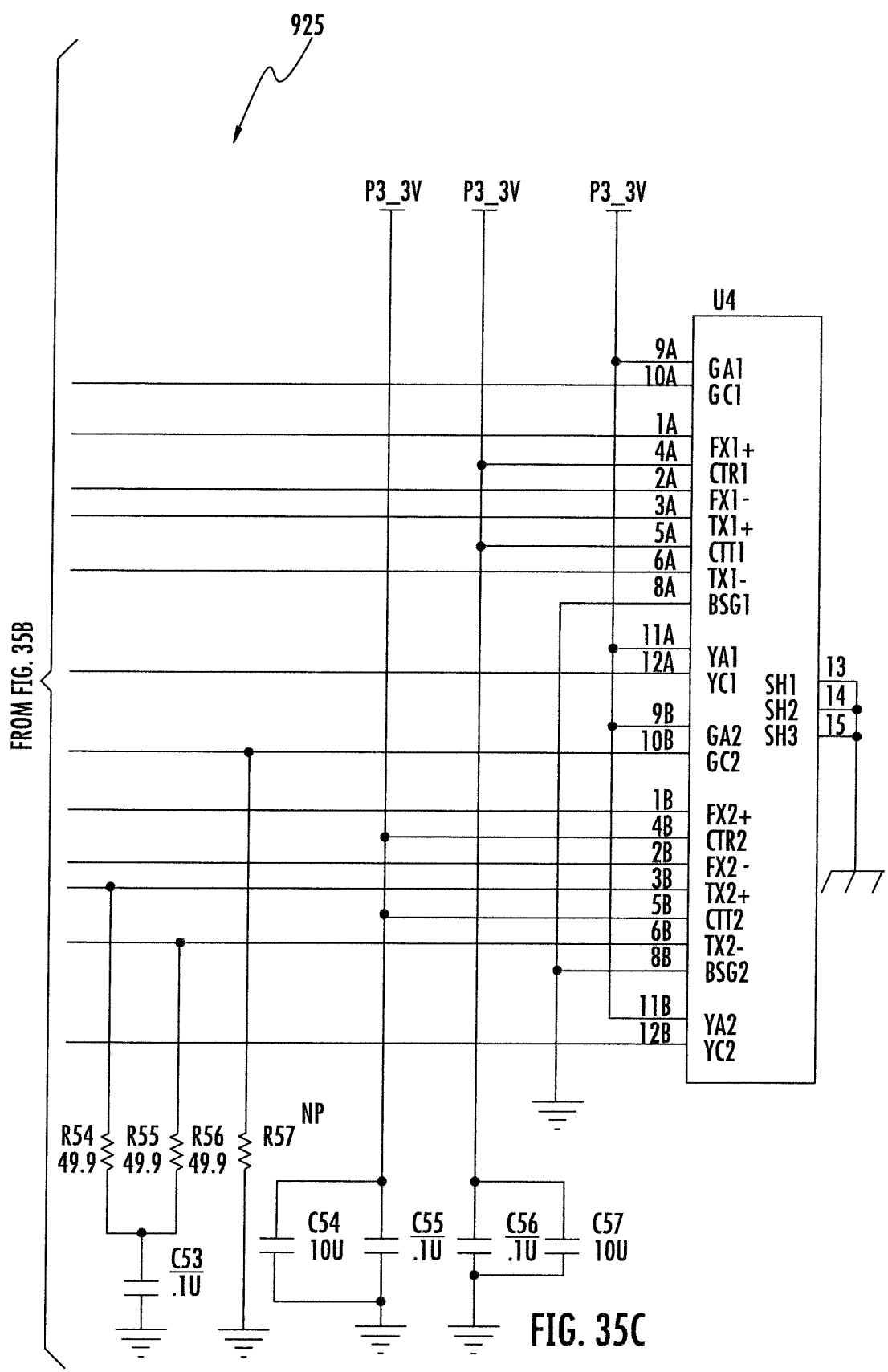
Figure 36A:
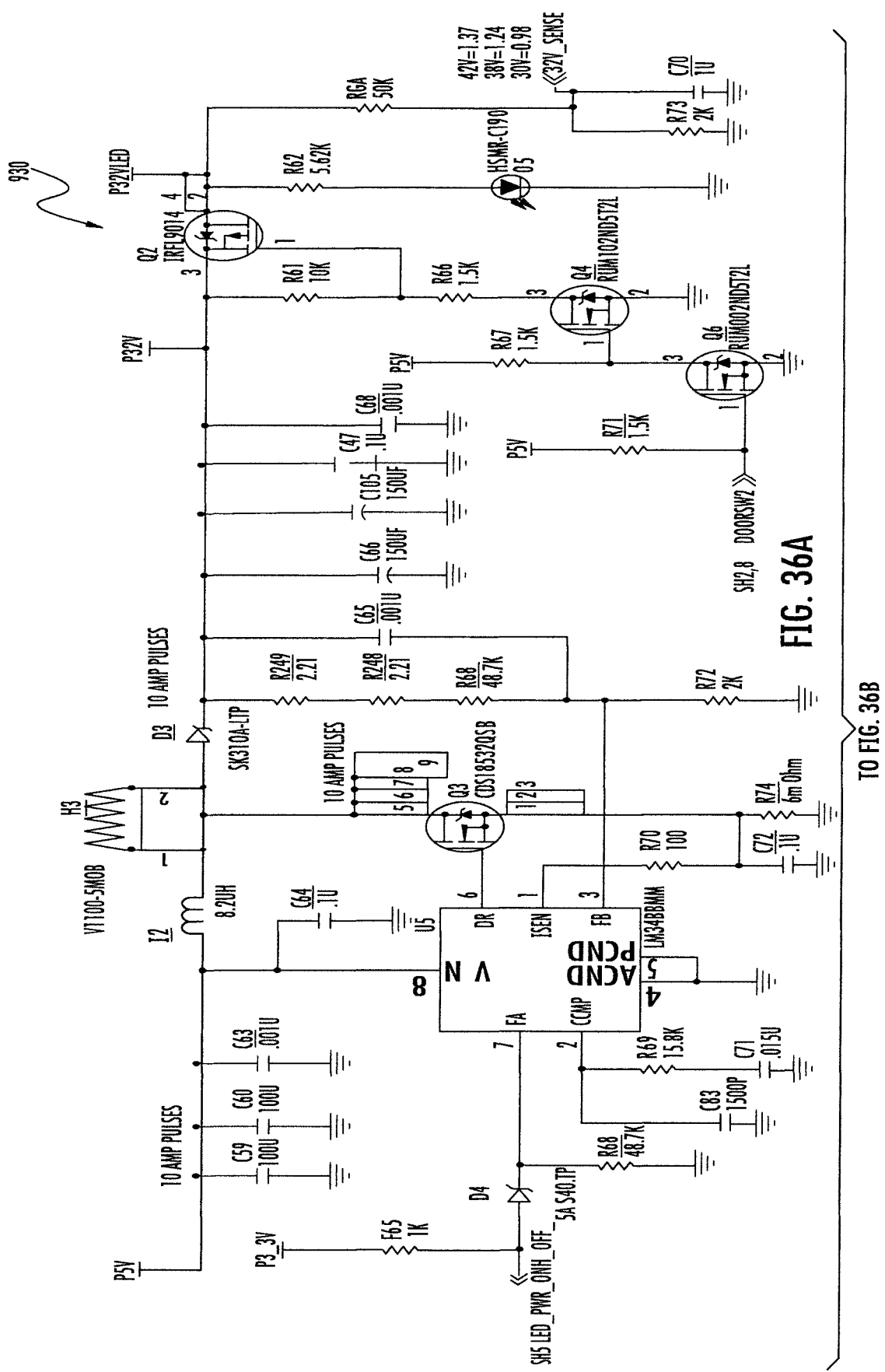
FIGS. 36A-36B are a circuit diagram for the power supplies in an embodiment of the UV sterilization device, according to the present disclosure.
Figure 36B:
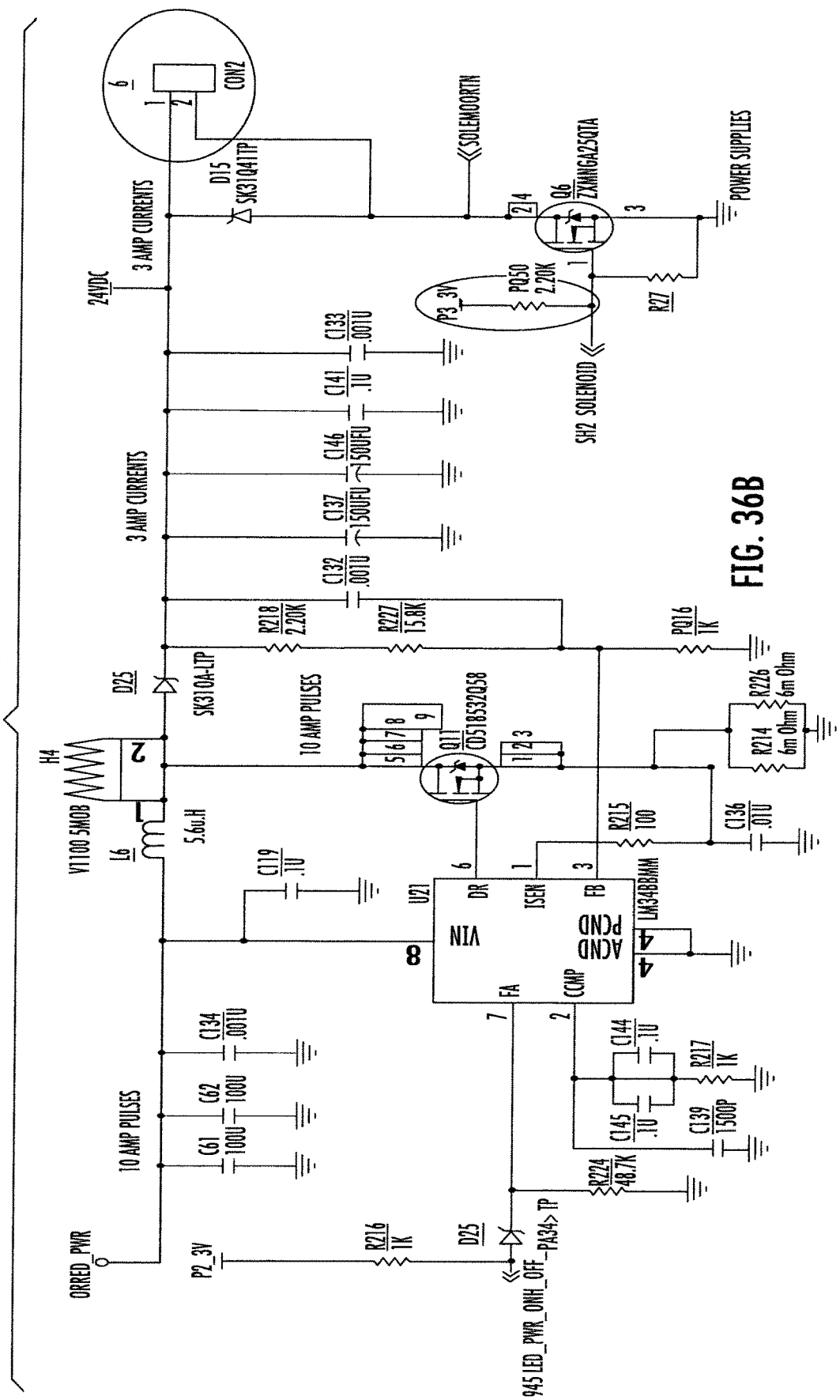
Figure 37:
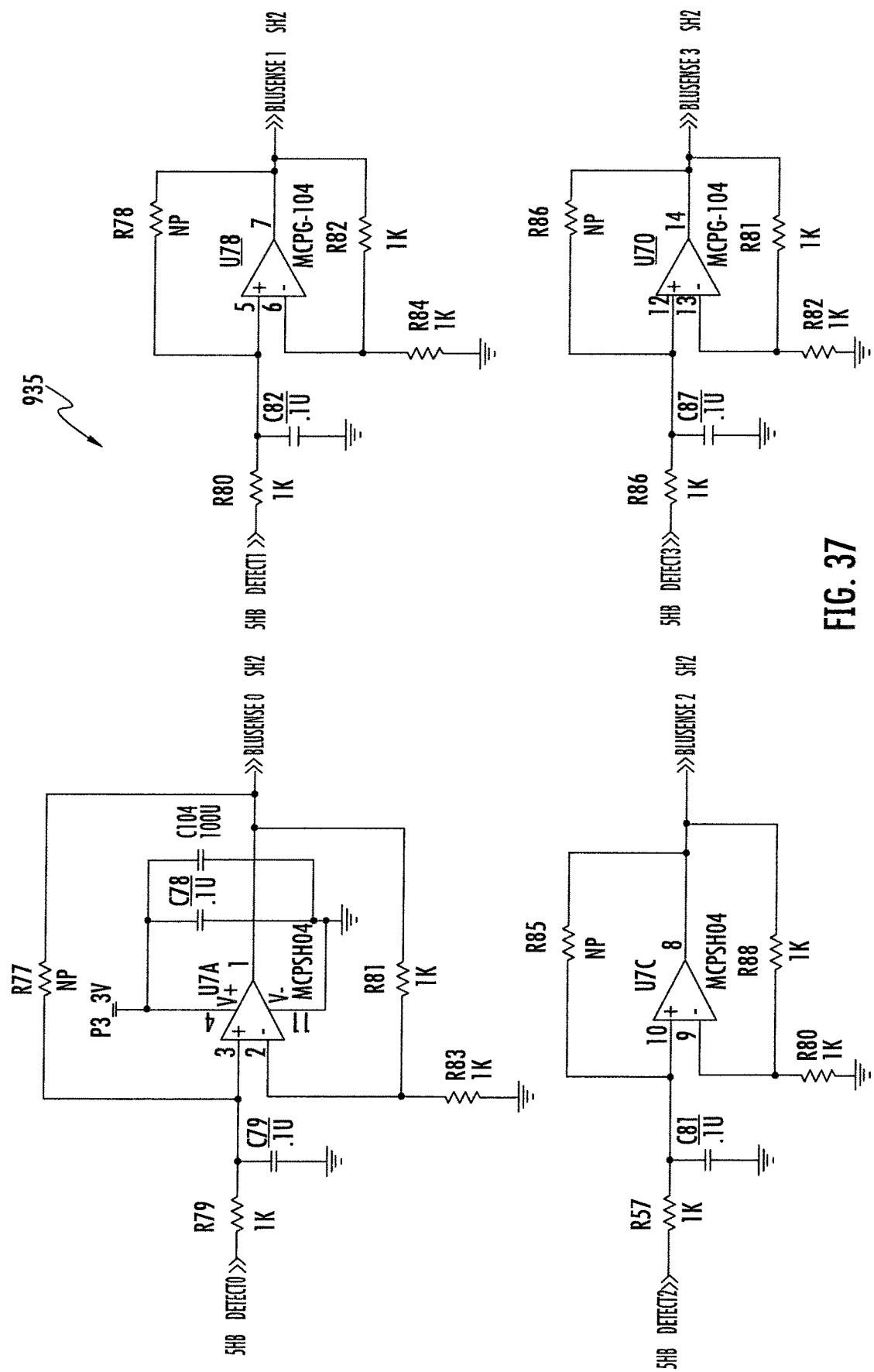
FIG. 37 is a circuit diagram for the detector circuits in an embodiment of the UV sterilization device, according to the present disclosure.
Figure 38A:
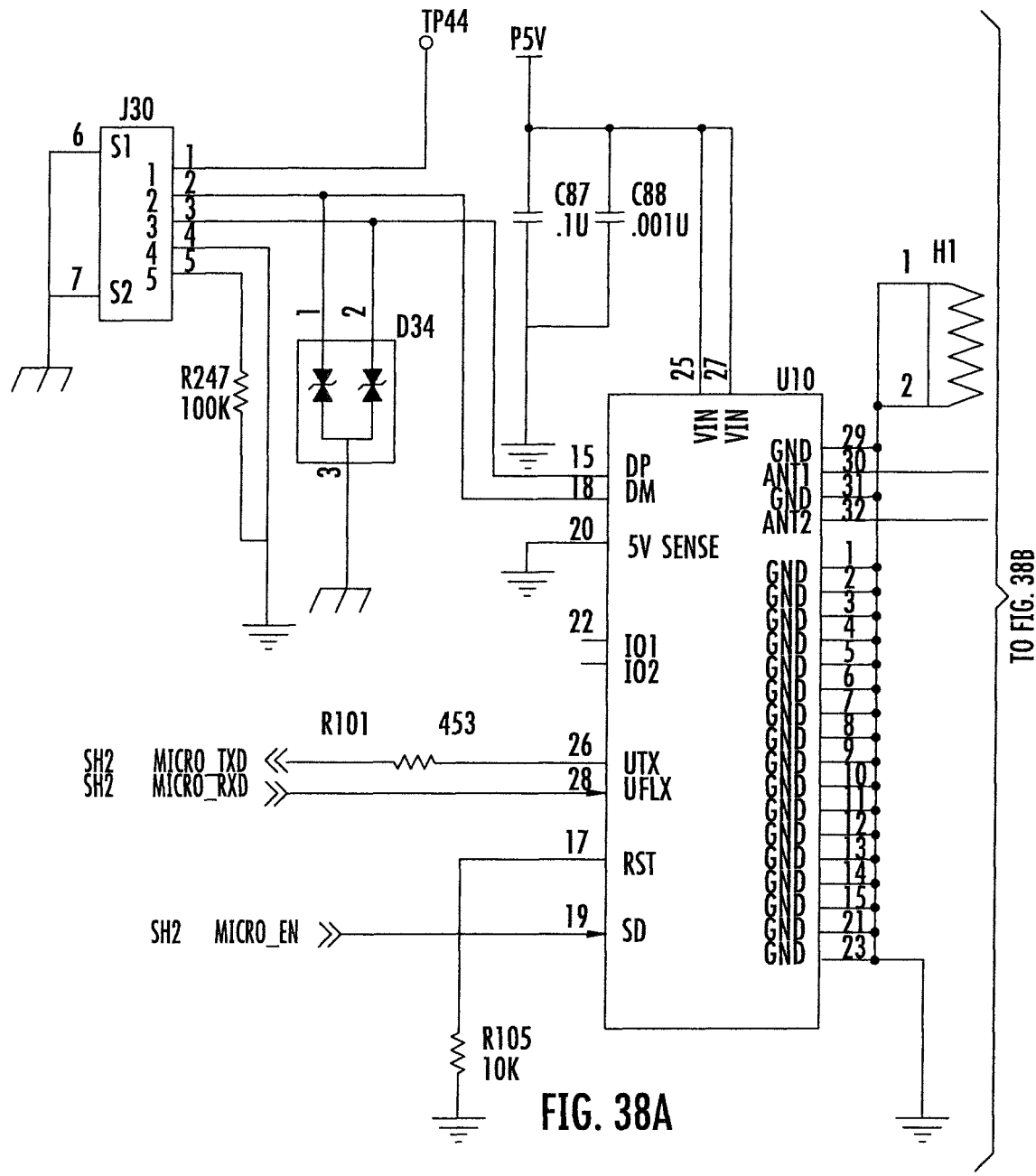
FIGS. 38A-38C are a circuit diagram for the RFID detection in an embodiment of the UV sterilization device, according to the present disclosure.
Figure 38B:
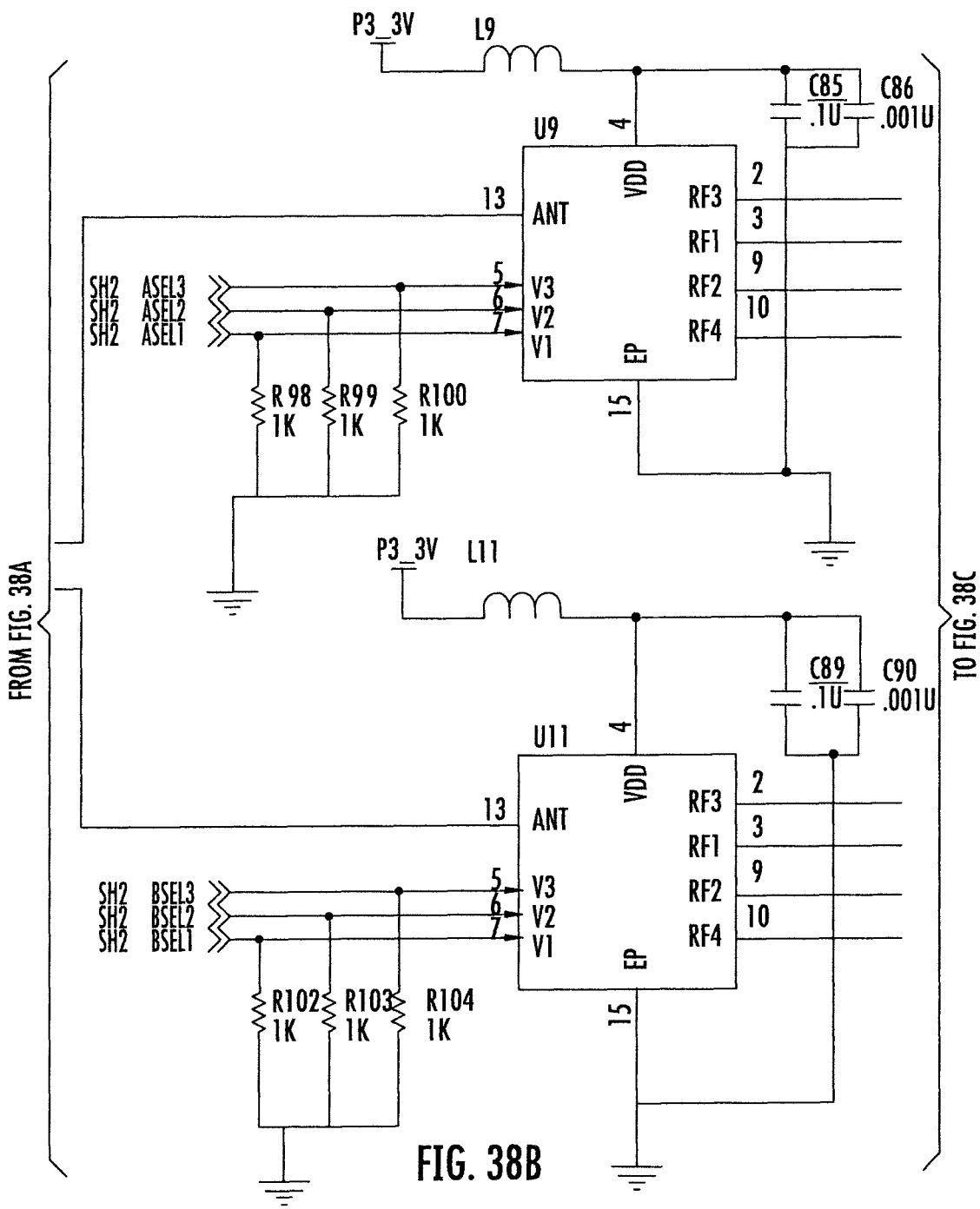
Figure 38C:
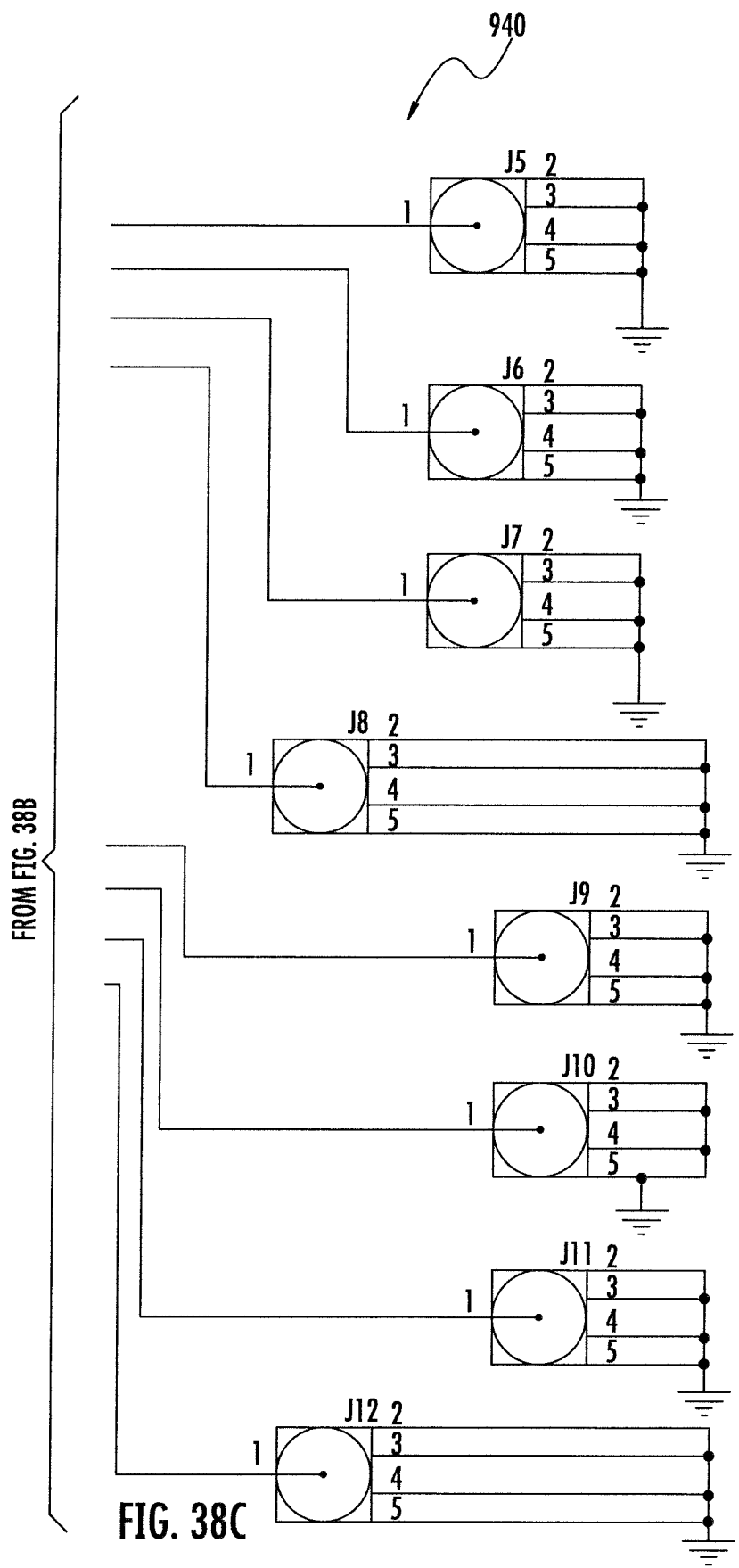
Figure 39A:
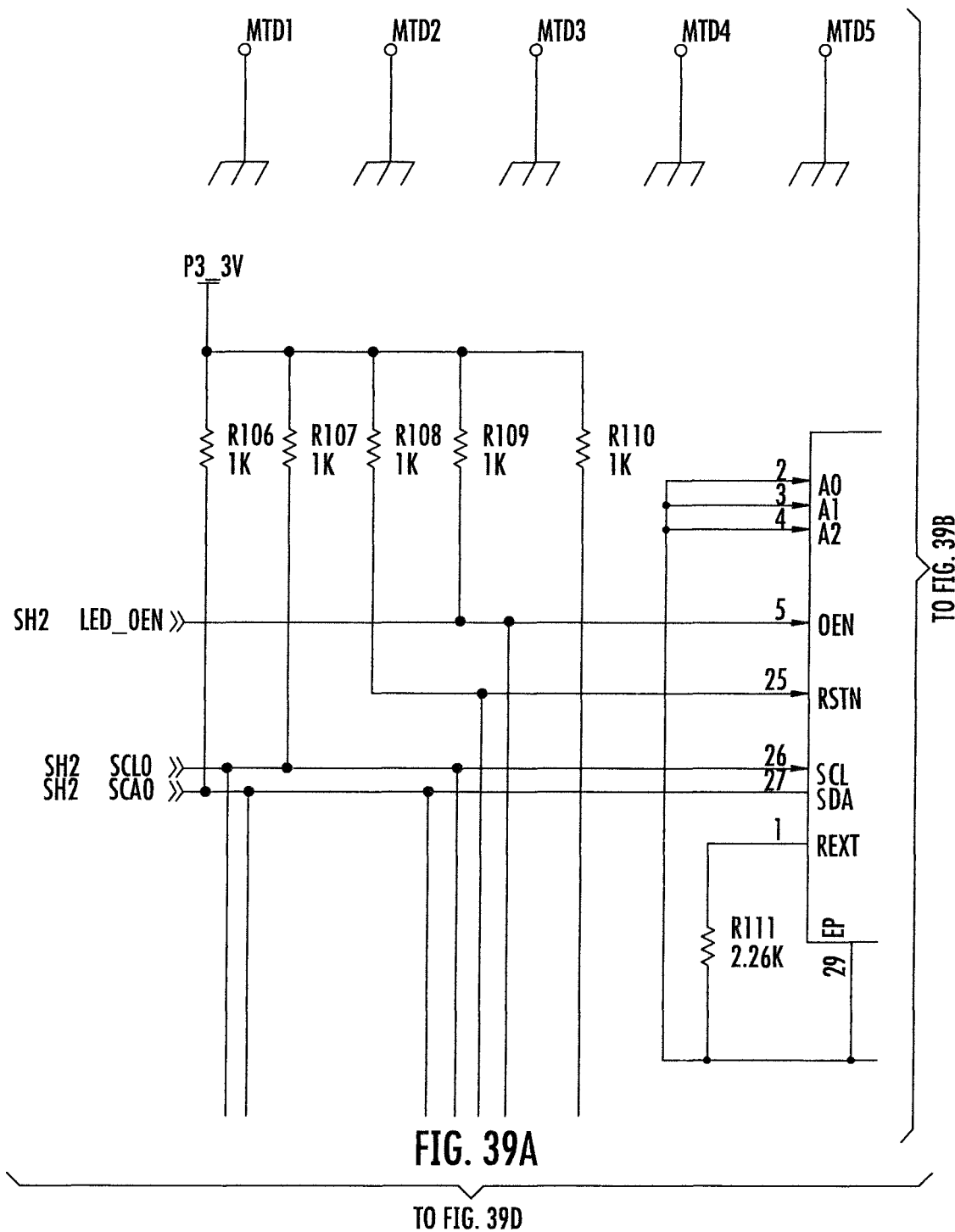
FIGS. 39A-39F are a circuit diagram for the UV LED drivers in an embodiment of the UV sterilization device, according to the present disclosure.
Figure 39B:
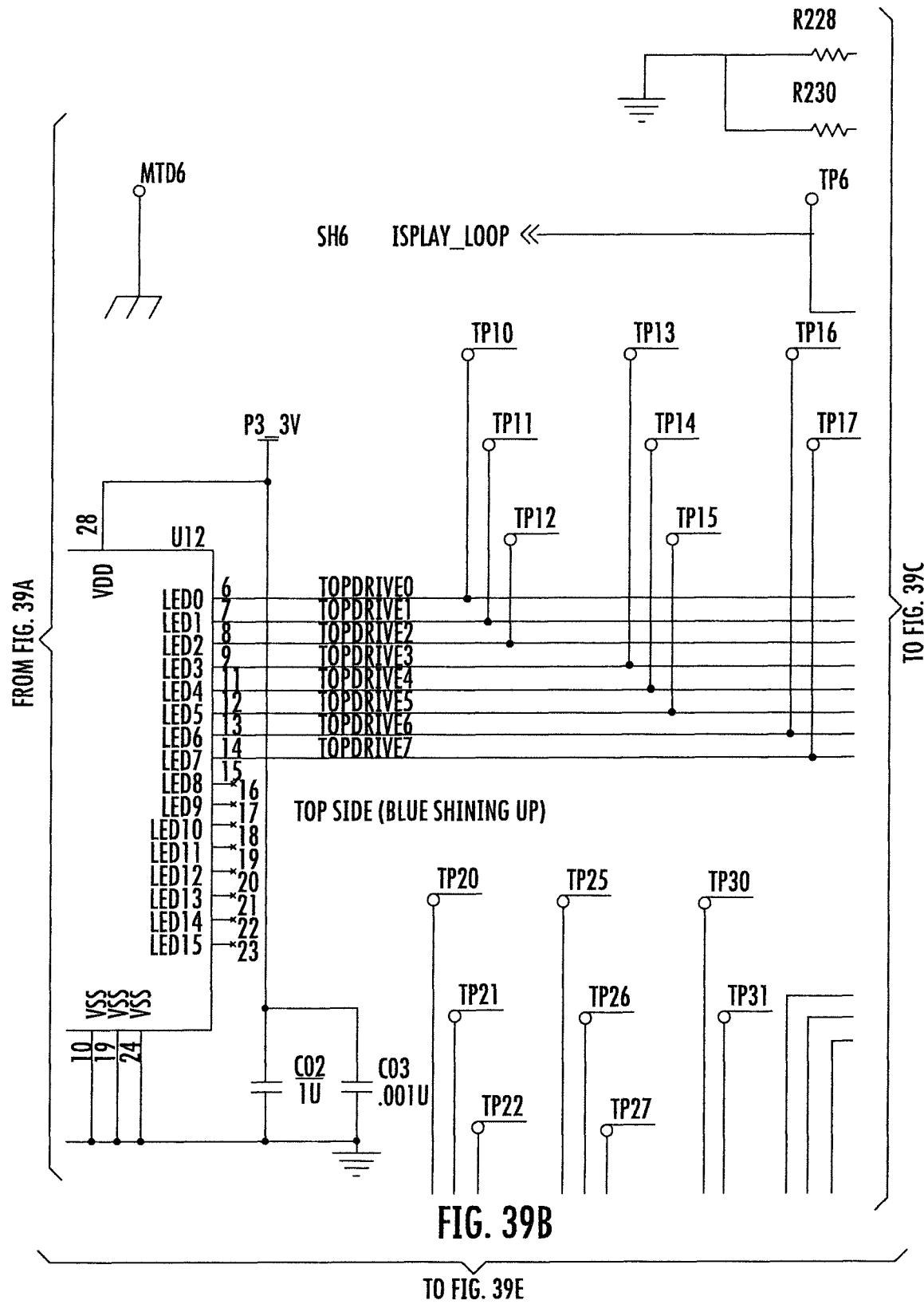
Figure 39C:
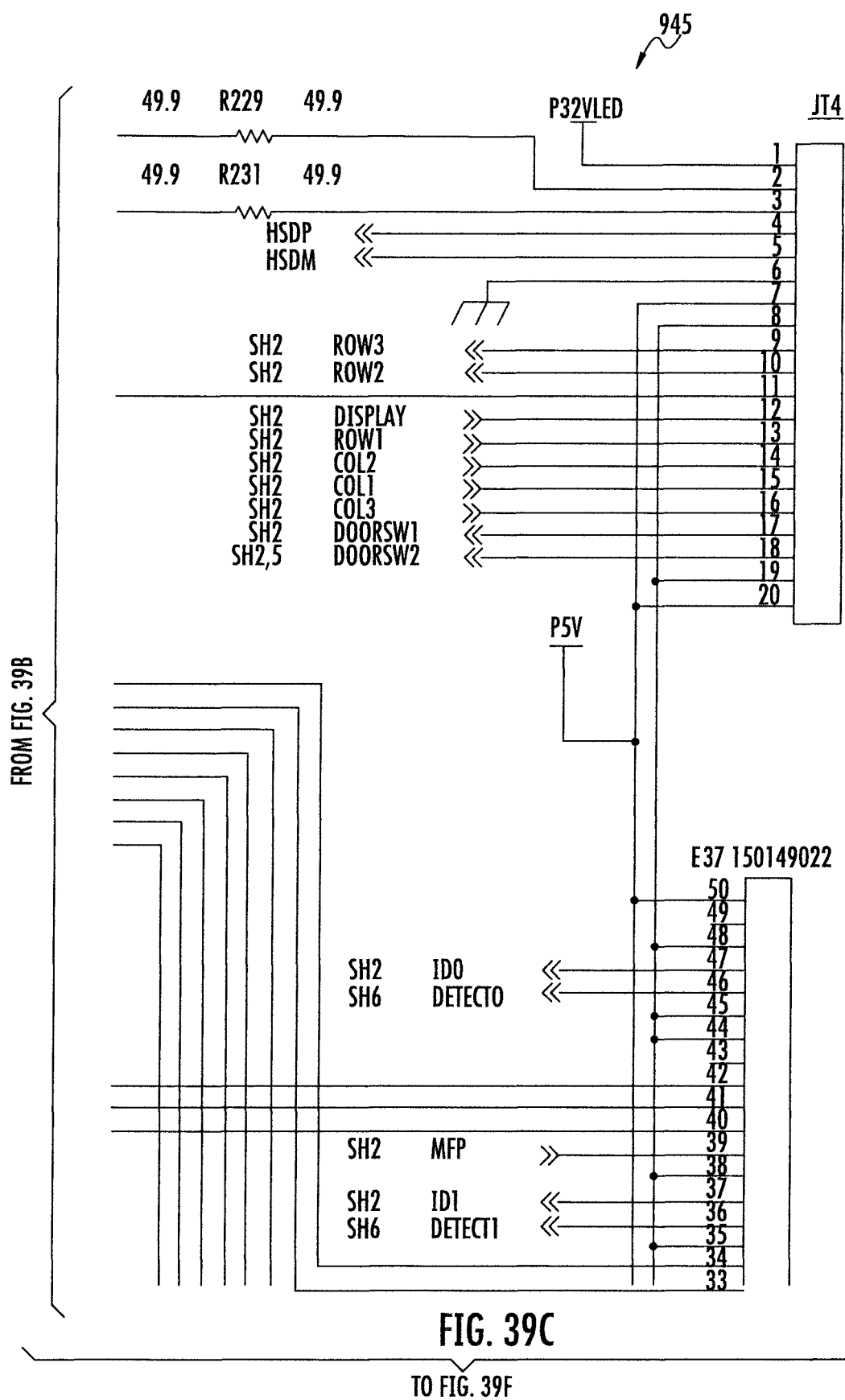
Figure 39D:
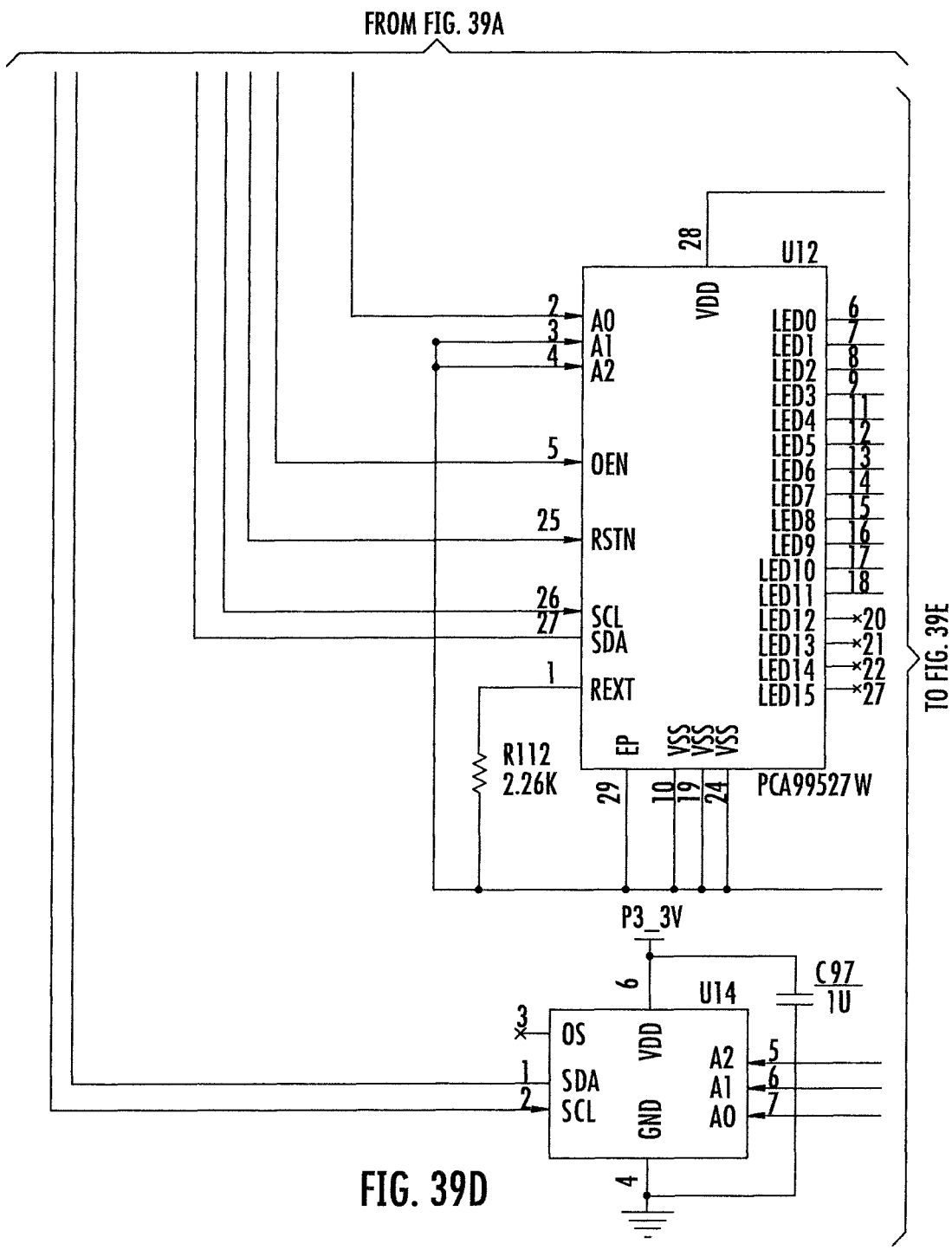
Figure 39E:
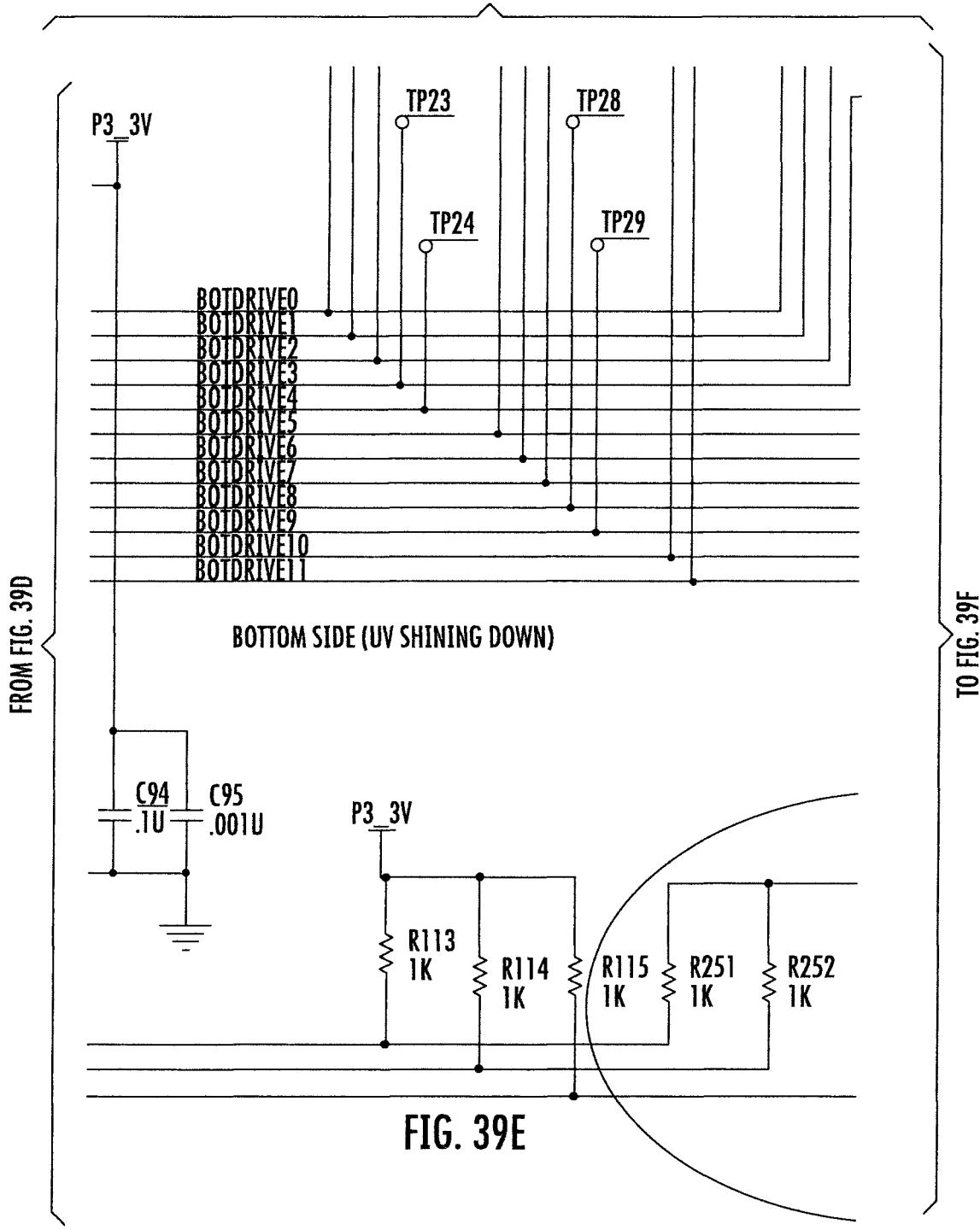
Figure 39F:
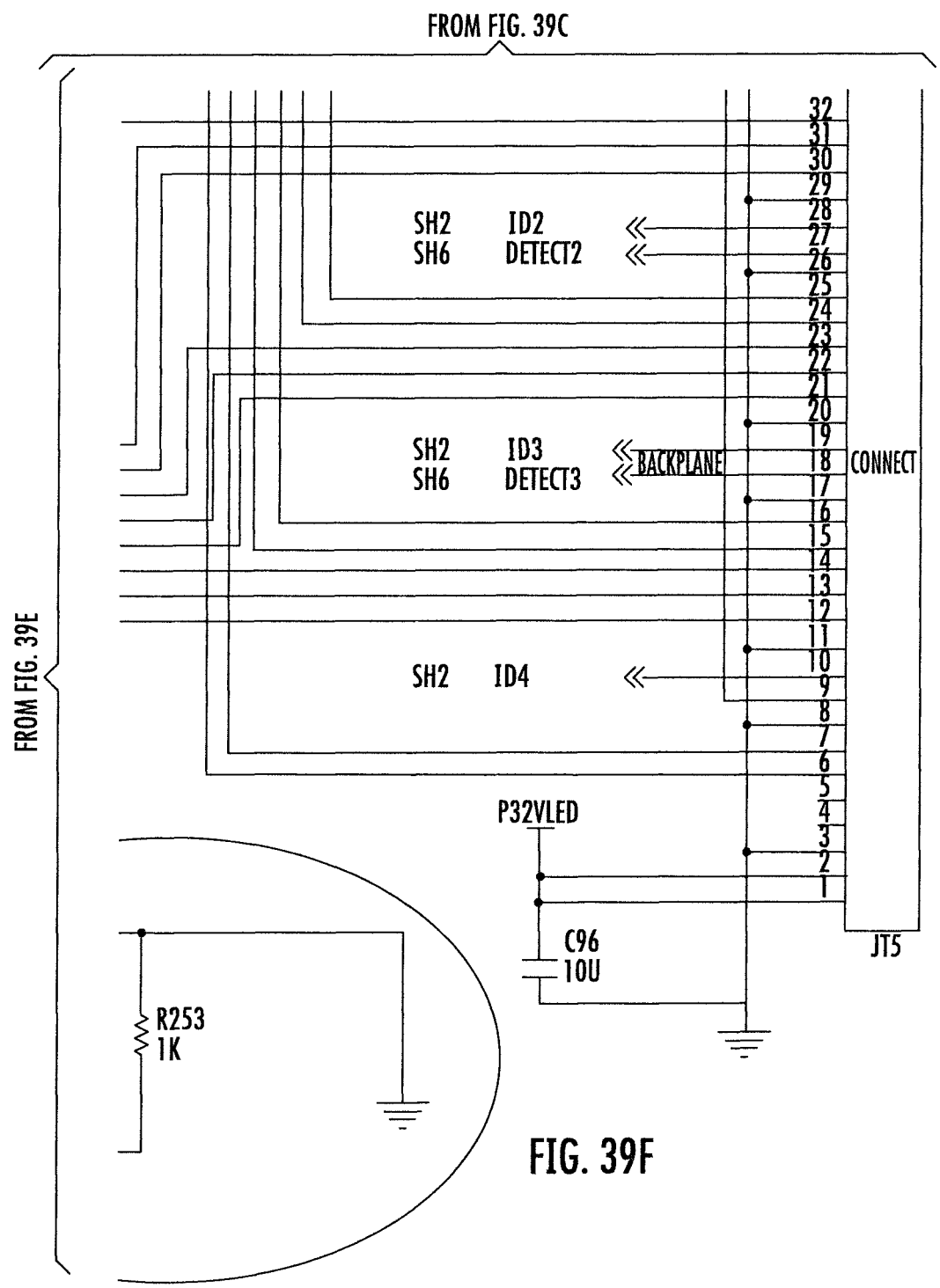
Figure 40:
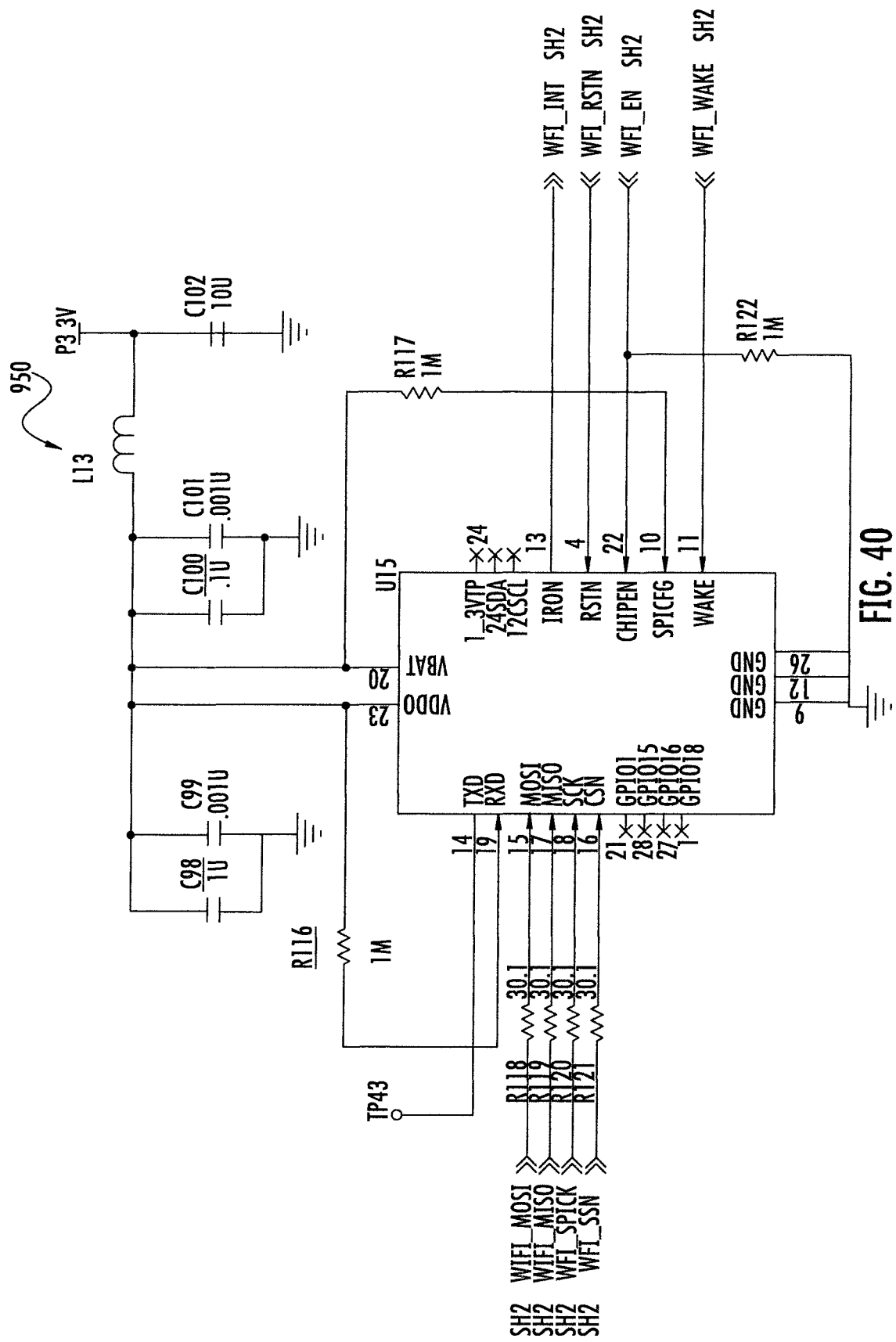
FIG. 40 is a circuit diagram for the wireless transceiver in an embodiment of the UV sterilization device, according to the present disclosure.
Figure 41:
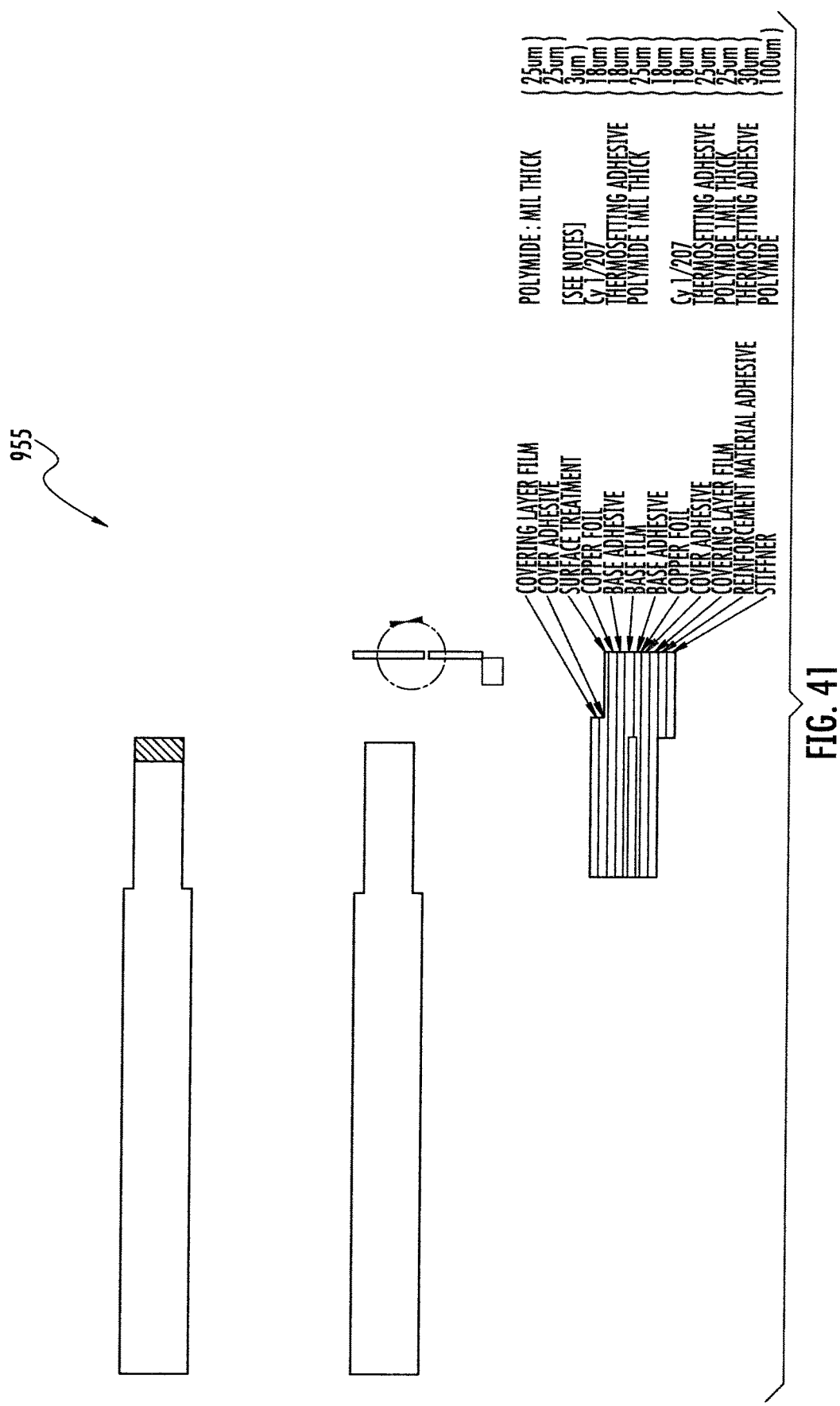
FIG. 41 is a schematic diagram for the flexible connector for the display in an embodiment of the UV sterilization device, according to the present disclosure.
Figure 42:
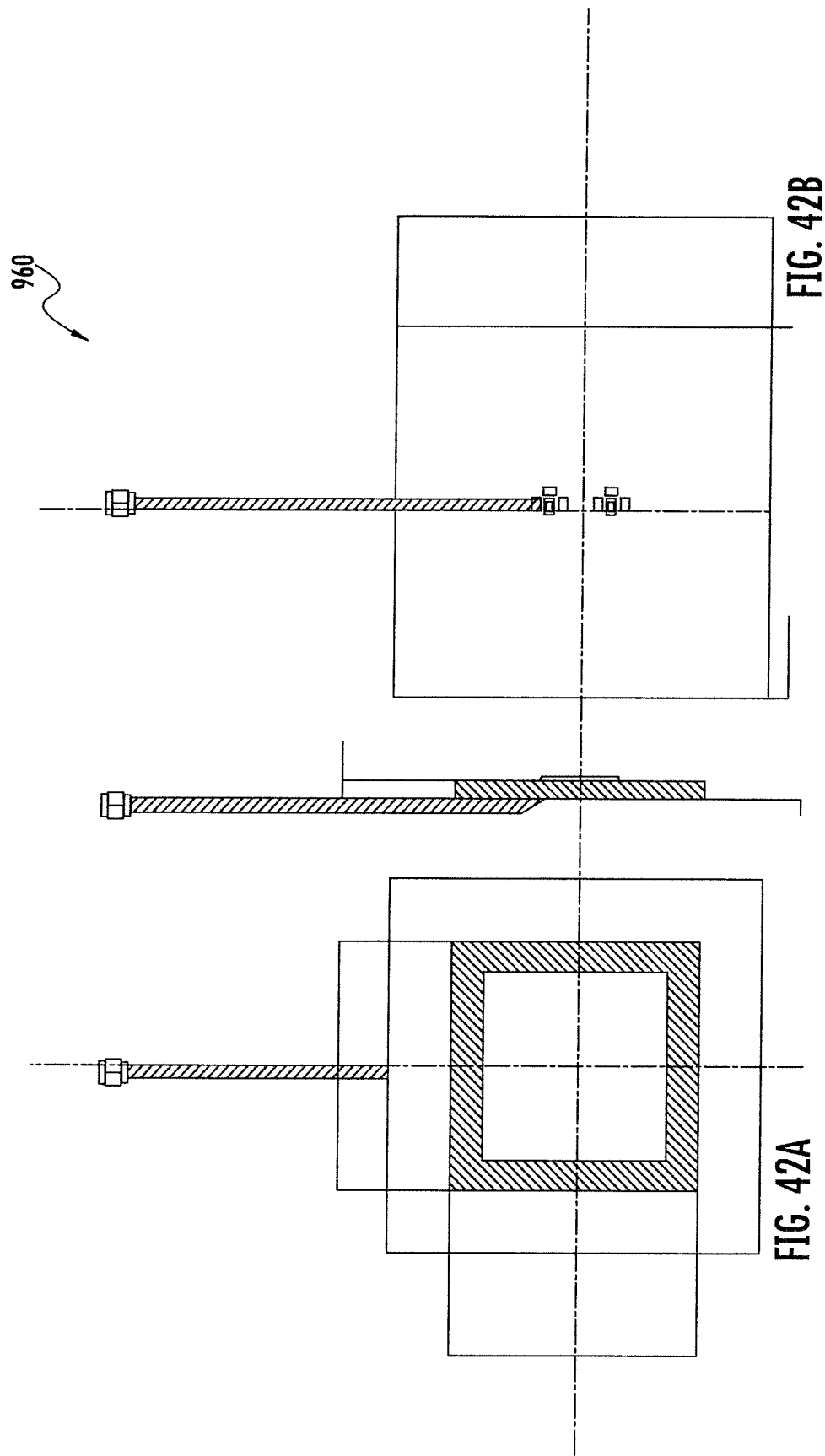
FIGS. 42A-42C are schematic diagrams for the antenna and coaxial connector in an embodiment of the UV sterilization device, according to the present disclosure.
Figure 43:
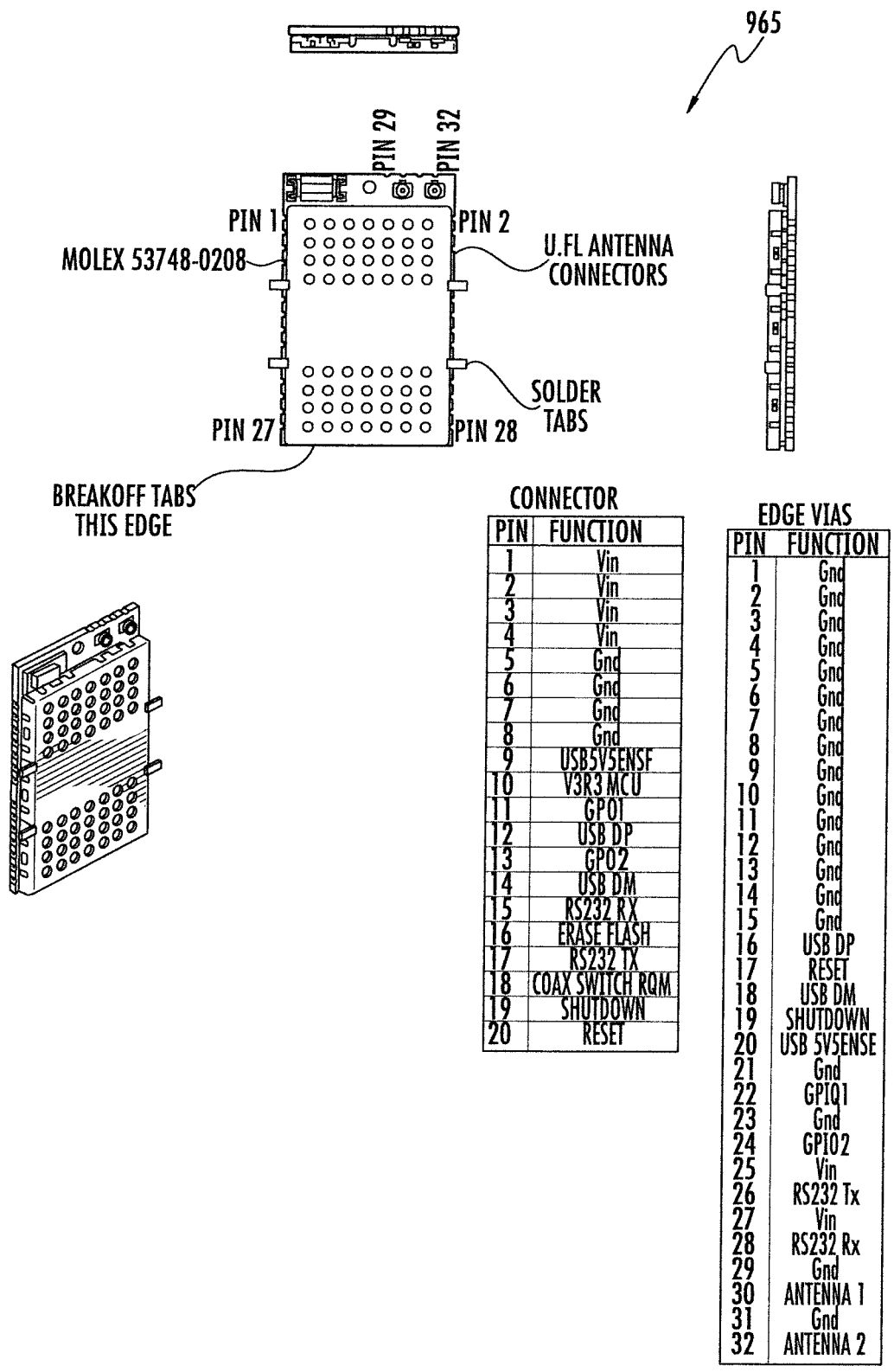
FIG. 43 is several views of the wireless transceiver in an embodiment of the UV sterilization device, according to the present disclosure.
Figure 44:
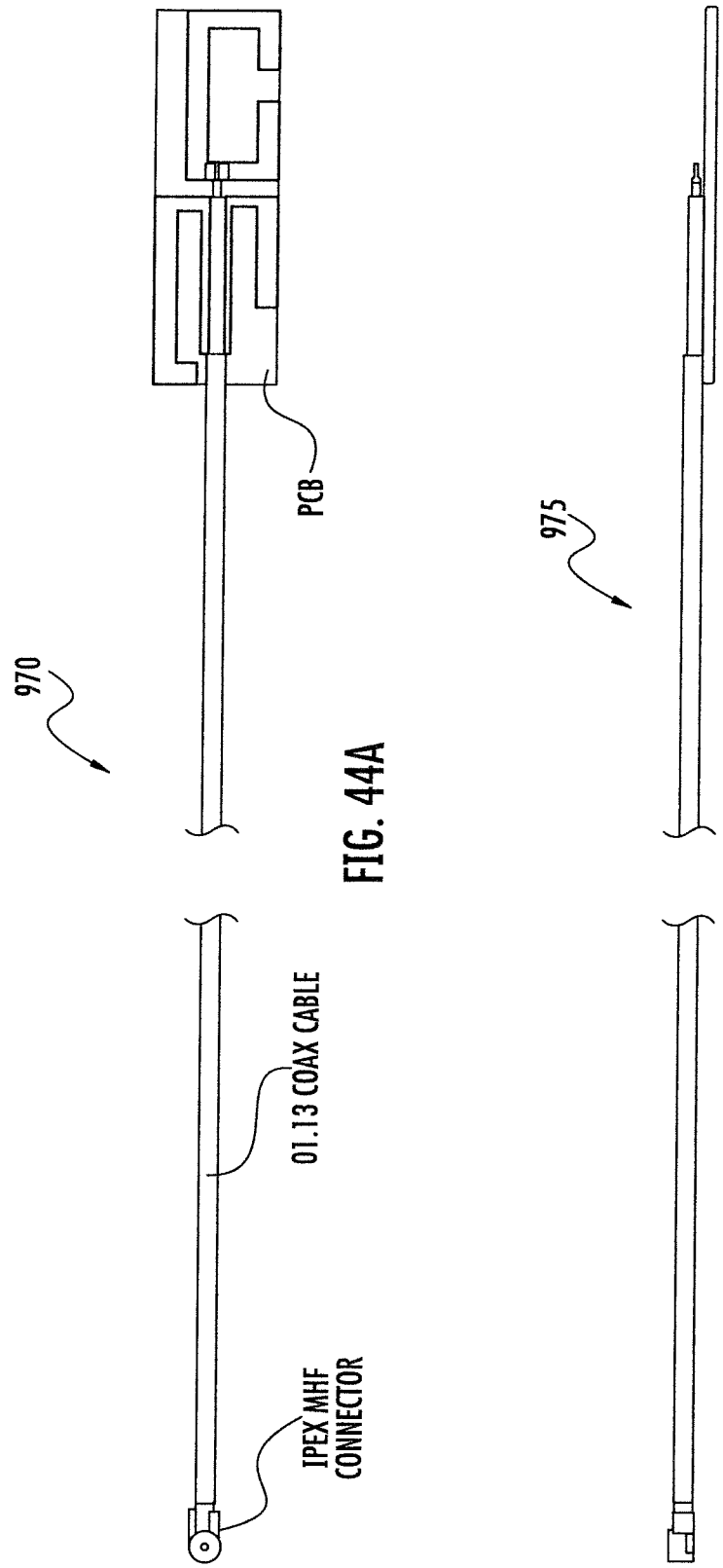
FIGS. 44A-44B are schematic diagrams for the antenna and coaxial connector in an embodiment of the UV sterilization device, according to the present disclosure.

Referring to FIGS. 28A-28M, patterns for circuit board layers for the backplane CBA 130 in the UV sterilization device 101*a*-101*d* are shown. Referring to FIGS. 29A-29I, patterns for circuit board layers for the display in the UV sterilization device 101*a*-101*d* are shown. Referring to FIGS. 30A-30B, patterns for circuit board layers for the UV CBAs 125*a*-125*d* in the UV sterilization device 101*a*-101*d* are shown.

Referring now to FIGS. 31-40, circuit diagrams 905, 910, 915, 920, 925, 930, 935, 940, 945, 950 illustrate several components from the UV sterilization device 101*a*-101*d*. Referring now to FIGS. 41-44B, diagrams 955, 960, 965, 970, 975 illustrate several components from the UV sterilization device 101*a*-101*d*.

Figure 45:
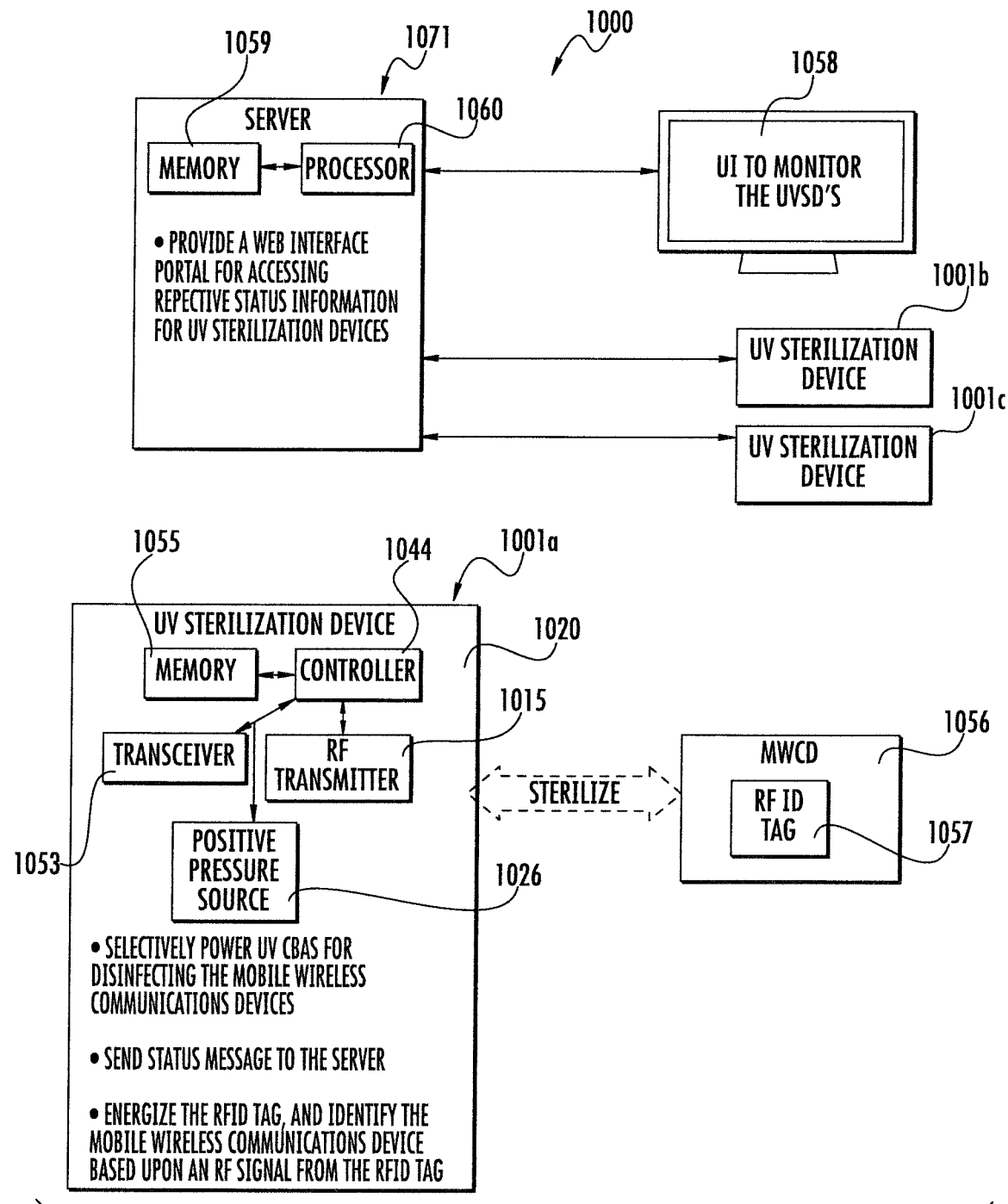
FIG. 45 is a schematic diagram of another embodiment of the UV sterilization system, according to the present disclosure.

Referring now additionally to FIG. 45, another embodiment of the UV sterilization system 100 is now described. In this embodiment of the UV sterilization system 1000, those elements already discussed above with respect to FIG. 1 are incremented by 900 and most require no further discussion herein. This embodiment differs from the previous embodiment in that this UV sterilization system 1000 illustratively includes the server 1011 having a memory 1059, and a processor 1060 coupled thereto, and the UV sterilization device 1001*a* having a controller 1044, and a memory 1055 coupled thereto. The UV sterilization system 1000 illustratively includes a mobile wireless communications device 1056 having an RF ID tag 1057 therein, and a remote terminal 1058 communication with the server 1011.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

That which is claimed is:

1. A method for operating an ultraviolet (UV) sterilization system comprising a server, and a plurality of UV sterilization devices, each UV sterilization device comprising a housing defining a cavity therein, and having a door configured to permit access to the cavity, at least one tray carried within the cavity configured to receive at least one device, the at least one device including a radio frequency (RF) identification (ID) tag, at least one UV circuit board assembly (CBA) carried within the cavity respectively adjacent the at least one tray and comprising a plurality of light emitting diode ultraviolet (LED UV) sources configured to irradiate the at least one device with UV radiation, each UV sterilization device comprising a transceiver configured to communicate with the server, and at least one RF transmitter coupled to a controller and configured to energize the RFID tag, the method comprising:
   operating the controller to identify the at least one device based upon an RF signal from the RFID tag, and determine a position and a number of the at least one device based upon the RF signal from the RFID tag;
   operating each UV sterilization device to selectively power the at least one UV CBA for disinfecting the at least one device based upon the identification of the at least one device and so that unused trays from the at least one tray are not irradiated, and send at least one status message to the server; and
   operating the server to provide a web interface portal for accessing respective status information for the plurality of UV sterilization devices.

2. The method of claim 1 wherein the at least one tray comprises a material transparent to UV radiation.

3. The method of claim 2 wherein the material comprises quartz.

4. The method of claim 1 further comprising operating each UV sterilization device to selectively power the at least one UV CBA when the at least one device is detected on a respective tray.

5. The method of claim 1 further comprising operating each UV sterilization device to unlock the door based upon a code received from a keypad.

6. The method of claim 1 further comprising operating each UV sterilization device to communicate with a wireless base station.

7. The method of claim 1 further comprising operating each UV sterilization device to create positive air pressure in the cavity when the door is open.

8. A method for operating a UV sterilization device including a housing defining a cavity therein, a door configured to permit access to the cavity, and at least one tray carried within the cavity and configured to receive at least one device, the at least one device including a radio frequency (RF) identification (ID) tag, the UV sterilization device including at least one UV circuit board assembly (CBA) carried within the cavity respectively adjacent the at least one tray and comprising a plurality of LED UV sources configured to irradiate the at least one device with UV radiation, the UV sterilization device including a controller and at least one RF transmitter coupled to the controller to energize the RFID tag, the method comprising:
   operating the controller to identify the at least one device based upon an RF signal from the RFID tag, and determine a position and a number of the at least one device based upon the RF signal from the RFID tag; and
   operating the controller to selectively power the at least one UV CBA for disinfecting the at least one device.

9. The method of claim 8 wherein the at least one tray comprises a material transparent to UV radiation.

10. The method of claim 9 wherein the material comprises quartz.

11. The method of claim 8 further comprising operating the controller to selectively power the at least one UV CBA when the at least one device is detected on a respective tray.

12. The method of claim 8 further comprising operating the controller to unlock the door based upon a code received from a keypad.

13. The method of claim 8 further comprising operating the controller to communicate with a wireless base station.

14. The method of claim 8 further comprising operating the controller to create positive air pressure in the cavity when the door is open.

15. A method for operating a UV sterilization device including a housing defining a cavity therein, a door configured to permit access to the cavity, and at least one tray carried within the cavity and configured to receive at least one device, the at least one tray comprising a material transparent to UV radiation, the at least one device including a radio frequency (RF) identification (ID) tag, the UV sterilization device including at least one UV circuit board assembly (CBA) carried within the cavity respectively adjacent the at least one tray and comprising a plurality of LED UV sources configured to irradiate the at least one device with UV radiation, the UV sterilization device including a controller and at least one RF transmitter coupled to the controller to energize the RFID tag, the method comprising:

operating the controller to selectively power the at least one UV CBA for disinfecting the at least one device;

operating the controller to identify the at least one device based upon an RF signal from the RFID tag, and determine a position and a number of the at least one device based upon the RF signal from the RFID tag;

operating each UV sterilization device to communicate with a wireless base station; and operating the controller to create positive air pressure in the cavity when the door is open.

16. The method of claim 15 wherein the material comprises quartz.

17. The method of claim 1 wherein each UV sterilization device comprises a light louver carried by the housing and configured to permit air to flow out of the cavity.

18. The method of claim 17 wherein the light louver comprises a plurality of interdigitated arms.

19. The method of claim 8 wherein each UV sterilization device comprises a light louver carried by the housing and configured to permit air to flow out of the cavity.

20. The method of claim 19 wherein the light louver comprises a plurality of interdigitated arms.

* * * * *